US008669091B2

(12) United States Patent
Gentschev et al.

(10) Patent No.: US 8,669,091 B2
(45) Date of Patent: Mar. 11, 2014

(54) MICROORGANISMS AS CARRIERS OF NUCLEOTIDE SEQUENCES CODING FOR ANTIGENS AND PROTEIN TOXINS, PROCESS OF MANUFACTURING AND USES THEREOF

(75) Inventors: Ivaylo Nikolov Gentschev, Wuerzburg (DE); Joachim Fensterle, Hoechberg (DE); Ulf R. Rapp, Wuerzburg (DE); Werner Goebel, Munich (DE)

(73) Assignee: Zentaris GmbH, Frankfurt am Main (DE)

( * ) Notice: Subject to any disclaimer, the term of this patent is extended or adjusted under 35 U.S.C. 154(b) by 1437 days.

(21) Appl. No.: 11/939,254

(22) Filed: Nov. 13, 2007

(65) Prior Publication Data
US 2011/0287037 A1 Nov. 24, 2011

Related U.S. Application Data

(60) Provisional application No. 60/939,140, filed on May 21, 2007, provisional application No. 60/865,484, filed on Nov. 13, 2006.

(30) Foreign Application Priority Data

Nov. 13, 2006 (EP) ..................................... 06123974

(51) Int. Cl.
*A01N 63/00* (2006.01)
*A61K 48/00* (2006.01)
*C12N 1/20* (2006.01)

(52) U.S. Cl.
USPC .................. 435/252.3; 424/93.2; 424/93.4

(58) Field of Classification Search
None
See application file for complete search history.

(56) References Cited

U.S. PATENT DOCUMENTS

| 5,366,858 A * | 11/1994 | Koizumi et al. .................. 435/5 |
| 2003/0235594 A1 * | 12/2003 | Humphreys et al. ....... 424/192.1 |
| 2006/0105423 A1 | 5/2006 | Rapp et al. |

FOREIGN PATENT DOCUMENTS

| WO | 98/23763 | * | 6/1998 |
| WO | 02/47727 | | 6/2002 |

OTHER PUBLICATIONS

Zhu et al (Vaccine vol. 24, pp. 3821-3831, 2006).*
Liljeqvist et al (Applied and Environmental Microbiology vol. 63, No. 7, pp. 2481-2488, Jul. 1997).*
Klauser et al (EMBO Journal vol. 9, No. 6, pp. 1991-1999, 1990).*
Edward Ryan, et al. "Protective Immunity against *Clostridium difficile* Toxin A Induced by Oral Immunization with a Live, Attenuated *Vibrio cholerae* Vector Strain", Infection and Immunity, vol. 65, No. 7, Jul. 1997, pp. 2941-2949.
Edward Ryan, et al. "Oral Immunization with Attenuated Vaccine Strains of *Vibrio cholerae* Expressing a Dodecapeptide Repeat of the Serine-Rich *Entamoeba histolytica* Protein Fused to the Cholera Toxin B Subunit Induces Systemic and Mucosal Antiamebic and Anti-V. *cholerae* Antibody Responses in Mice", Infection and Immunity, vol. 65, No. 8, Aug. 1997, pp. 3118-3125.
Chengru Zhu, et al. "Delivery of heterologous protein antigens via hemolysin or auto transporter systems by an attenuated *ler* mutant of rabbit enteropathogenic *Escherichia coli*", Vaccine, vol. 24, No. 18, May 2006, pp. 3821-3831.
Barbara Tzschaschel, et al. "Towards a vaccine candidate against *Shigella dysenteriae* 1: expression of the Shiga toxin B-subunit in an attenuated *Shigella flexneri* aroD carrier strain", Microbial Pathogenesis, vol. 21, No. 4, 1996, pp. 277-288.
Barbara Tzschaschel, et al. "An *Escherichia coli* hemolysin transport system-based vector for the export of polypeptides: Export of Shiga-like toxin IIeB subunit by *Salmonella typhimurium* aroA". Nature Biotechnology, vol. 14, No. 6, 1996, pp. 765-769.
Guido Dietrich, et al. "Haemolysin A and listeriolysin—two vaccine delivery tools for the induction of cell-mediated immunity", Int. J. for Parasitology vol. 33, No. 5-6, May 2003, pp. 495-505.
Joachim Fensterle, et al. "B-Raf specific antibody responses in melanoma patients", Cancer Gene Therapy, vol. 15, No. 2, 2008, pp. 85-93.
Ivaylo Gentschev, et al. "The *E. coli* α-hemolysin secretion system and its use in vaccine development", Trends in Microbiology, vol. 10, No. 1, Jan. 2002, pp. 39-45.
Ivaylo Gentschev, et al. "Use of a recombinant *Salmonella enterica* serovar *Typhimurium* strain expressing C-Raf for protection against C-Raf induced lung adenoma in mice", BMC Cancer, Biomed Central, vol. 5, No. 1, Feb. 2005, pp. 1-9.
Ivaylo Gentschev, et al. "Use of the α-hemolysin secretion system of *Escherichia coli* for antigen delivery in the *Salmonella typhi* Ty21a vaccine strain", Int. J. of Medical Microbiology, vol. 294, No. 6, Nov. 2004, pp. 363-371.
Daniela Loeffler, et al. "Comparison of Different Live Vaccine Strategies in Vivo for Delivery of Protein Antigen or Antigen-Encoding DNA and mRNA by Virulence-Attenuated *Listeria monocytogenes*", Infection and Immunity, vol. 74, No. 7, Jul. 2006, pp. 3946-3957.
Shi Cheng-Hua et al, "Gene Fusion of cholera toxin B subunit and HBV PreS2 epitope and the antigenicity of fusion protein". Vaccine, vol. 13, No. 10, Jul. 1995, pp. 933-937.
Alba Sanchez et al. "Cholera Toxin B-Subunit Gene Enhances Mucosal Immunoglobulin A, Th1-Type, and CD8+ Cytotoxic Responses When Coadministered Intradermally with a DNA Vaccine", Clinical and Diagnostic Laboratory Immunology, vol. 11, No. 4, Jul. 2004, pp. 711-719.
International Search Report issued Apr. 3, 2008 in PCT/EP2007/062237.
Office Action mailed Jul. 27, 2010, in New Zealand Patent Application No. 576947.

* cited by examiner

*Primary Examiner* — Albert Navarro

(74) *Attorney, Agent, or Firm* — Oblon, Spivak, McClelland, Maier & Neustadt, L.L.P.

(57) ABSTRACT

A *Escherichia, Salmonella, Yersinia, Vibrio, Listeria, Shigella*, or *Pseudomonas* bacterium that has the following components: (I) a polynucleotide encoding a heterologous antigenic determinant that induces a CTL response against a tumor cell; (II) a polynucleotide encoding a heterologous protein toxin or toxin subunit; and (III) (a) a polynucleotide encoding a transport system that expresses the products of (I) and (II) on the outer surface of the bacterium or that secretes products of (I) and (II) from the bacterium; and (IV) a polynucleotide that activates the expression of one or more of (I). (II), and/Or (III) in the bacterium wherein polynucleotides (I), (II), (III) and (IV) are different from each other and polynucleotides (I), (II) and (III) encode proteins that are different from each other.

24 Claims, 22 Drawing Sheets

Figure 1 hlyA:

ATGCCAACAATAACCACTGCACAAATTAAAAGCACACTGCAGTCTGCAAAGCAATCCGCT
GCAAATAAATTGCACTCAGCAGGACAAAGCACGAAAGATGCATTAGCCTATGGAAGTCAG
GGTGATCTTAATCCATTAATTAATGAAATCAGCAAAATCATTTCAGCTGCAGGTAGCTTC
GATGTTAAAGAGGAAAGAACTGCAGCTTCTTTATTGCAGTTGTCCGGTAATGCCAGTGAT
TTTTCATATGGACGGAACTCAATAACCCTGACCACATCAGCATAA

Figure 2 hlyB:

ATGGATTCTTGTCATAAAATTGATTATGGGTTATACGCCCTGGAGATTTTAGCCCAATAC
CATAACGTCTCTGTTAACCCGGAAGAAATTAAACATAGATTTGATACAGACGGGACAGGT
CTGGGATTAACGTCATGGTTGCTTGCTGCGAAATCTTTAGAACTAAAGGTAAAACAGGTA
AAAAAAACAATTGATCGATTAAACTTTATTTTTCTGCCCGCATTAGTCTGGAGAGAGGAT
GGACGTCATTTTATTCTGACTAAAATCAGCAAAGAAGTAAACAGATATCTTATTTTTGAT
TTGGAGCAGCGAAATCCCCGTGTTCTCGAACAGTCTGAGTTTGAGGCGTTATATCAGGGG
CATATTATTCTTATTACTTCCCGTTCTTCTGTTACCGGGAAACTGGCAAAATTTGACTTT
ACCTGGTTTATTCCTGCCATTATAAAATACAGGAGAATATTTATTGAAACCCTTGTTGTA
TCTGTTTTTTTACAATTATTTGCATTAATAACCCCCCTTTTTTTTCAGGTGGTTATGGAC
AAAGTATTAGTGCACAGGGGGTTTTCAACCCTTAATGTTATTACTGTTGCCTTATCTGTT
GTAGTGGTGTTTGAGATTATACTCAGCGGTTTAAGAACTTACATTTTTGCACATAGTACA
AGTCGGATTGATGTTGAGTTGGGTGCCAAACTCTTCCGGCATTTACTGGCGCTACCGATC
TCTTATTTTGAGAGTCGTCGTGTTGGTGATACTGTTGCGAGGGTAAGAGAATTAGACCAG
ATCCGTAATTTTCTGACAGGACAGGCATTAACATCTGTTTTGGACTTATTATTTTCACTC
ATATTTTTTGCGGTAATGTGGTATTACAGCCCAAAGCTTACTCTGGTGATCTTATTTTCG
CTGCCTTGTTATGCTGCATGGTCTGTTTTTATTAGCCCCATTTTGCGACGTCGCCTTGAT
GATAAGTTTTCACGGAATGCGGATAATCAATCTTTCCTGGTGGAATCAGTAACGGCGATT
AACACTATAAAAGCTATGGCAGTCTCACCTCAGATGACGAACATATGGGACAAACAATTG
GCAGGATATGTTGCTGCAGGCTTTAAAGTGACAGTATTAGCAACCATTGGTCAACAAGGA
ATACAGTTAATACAAAAGACTGTTATGATCATCAACCTATGGTTGGGAGCACACCTGGTT
ATTTCCGGGGATTTAAGTATTGGTCAGTTAATTGCTTTTAATATGCTTGCTGGTCAGATT
GTTGCACCGGTTATTCGCCTTGCACAAATCTGGCAGGATTTCCAGCAGGTTGGTATATCA
GTTACCCGCCTTGGTGATGTGCTTAACTCTCCAACTGAAAGTTATCATGGGAAACTGACA
TTGCCGGAAATTAATGGTGATATCACTTTTCGTAATATCCGGTTTCGCTATAAACCTGAT
TCTCCGGTTATTTTGGACAATATCAATCTTAGTATTAAGCAGGGGGAGGTTATTGGTATT
GTCGGACGTTCTGGTTCAGGAAAAAGCACATTAACTAAATTAATTCAACGTTTTTATATT
CCTGAAAATGGCCAGGTATTAATTGATGGACATGATCTTGCGTTGGCCGATCCTAACTGG
TTACGTCGTCAGGTGGGGGTTGTGTTGCAGGACAATGTGCTGCTTAATCGCAGTATTATT
GATAATATTTCACTGGCTAATCCTGGCATGTCCGTCGAAAAAGTTATTTATGCAGCGAAA
TTAGCAGGTGCTCATGATTTTATTTCTGAATTGCGTGAGGGGTATAACACCATTGTCGGG
GAACAGGGGGCAGGATTATCCGGAGGTCAACGTCAACGCATCGCAATTGCAAGGGCGCTG
GTGAACAACCCTAAAATACTCATTTTTGATGAAGCAACCAGTGCTCTGGATTATGAGTCG
GAGCATGTCATCATGCGCAATATGCACAAAATATGTAAGGGCAGAACGGTTATAATCATT
GCTCATCGTCTGTCTACAGTAAAAAATGCAGACCGCATTATTGTCATGGAAAAAGGGAAA
ATTGTTGAACAGGGTAAACATAAGGAGCTGCTTTCTGAACCGGAAAGTTTATACAGTTAC
TTATATCAGTTACAGTCAGACTAA

Figure 3 hlyD:
ATGAAAACATGGTTAATGGGGTTCAGCGAGTTCCTGTTGCGCTATAAACTTGTCTGGAGT
GAAACATGGAAAATCCGGAAGCAATTAGATACTCCGGTACGTGAAAAGGACGAAAATGAA
TTCTTACCCGCTCATCTGGAATTAATTGAAACGCCAGTATCCAGACGGCCGCGTCTGGTT
GCTTATTTTATTATGGGGTTTCTGGTTATTGCTTTTATTTTATCTGTTTTAGGCCAAGTG
GAAATTGTTGCCACTGCAAATGGGAAATTAACACACAGTGGGCGTAGTAAAGAAATTAAA
CCTATTGAAAACTCAATAGTTAAAGAAATTATCGTAAAAGAAGGAGAGTCAGTCCGGAAA
GGGGATGTGTTATTAAAGCTTACAGCACTGGGAGCTGAAGCTGATACGTTAAAAACACAG
TCATCACTGTTACAGGCCAGGCTGGAACAAACTCGGTATCAAATTCTGAGCAGGTCAATT
GAATTAAATAAACTACCTGAACTAAAGCTTCCTGATGAGCCTTATTTTCAGAATGTATCT
GAAGAGGAAGTACTGCGTTTAACTTCTTTGATAAAAGAACAGTTTTCCACATGGCAAAAT
CAGAAGTATCAAAAAGAACTGAATTTGGATAAGAAAAGAGCAGAGCGATTAACAGTACTT
GCCCGTATAAACCGTTATGAAAATTTATCAAGGGTTGAAAAAGCCGTCTGGATGATTTC
AGTAGTTTATTGCATAAACAGGCAATTGCAAAACATGCTGTACTTGAGCAGGAGAATAAA
TATGTCGAAGCAGTAAATGAATTACGAGTTTATAAATCACAACTGGAGCAAATTGAGAGT
GAGATATTGTCTGCAAAAGAAGAATATCAGCTTGTTACGCAGCTTTTTAAAAATGAAATT
TTAGATAAGCTAAGACAAACCACAGACAACATTGGGTTATTAACTCTGGAATTAGCGAAA
AATGAAGAGCGTCAACAGGCTTCAGTAATCAGGGCCCCAGTTTCGGTAAAAGTTCAGCAA
CTGAAGGTTCATACTGAAGGTGGGGTTGTTACAACAGCGGAAACACTGATGGTCATCGTT
CCGGAAGATGACACGCTGGAGGTTACTGCTCTGGTACAAAATAAAGATATTGGTTTTATT
AACGTCGGGCAGAATGCCATCATTAAAGTGGAGGCATTTCCTTATACACGATATGGTTAT
CTGGTGGGTAAGGTGAAAAATATAAATTTAGATGCAATAGAAGACCAGAGACTGGGACTT
GTTTTTAATGTTATTATTTCTATTGAAGAGAATTGTTTGTCAACCGGAAATAAAAACATT
CCATTAAGCTCGGGTATGGCAGTCACTGCAGAAATAAAGACAGGTATGCGAAGTGTAATC
AGTTATCTTCTTAGTCCTTTAGAAGAGTCAGTAACAGAAAGTTTACGTGAGCGTTAA

Figure 4

PSA:

GTGGGAGGCTGGGAGTGCGAGAAGCATTCCCAACCCTGGCAGGTGCTTGTGGCCTCTCGT
GGCAGGGCAGTCTGCGGCGGTGTTCTGGTGCACCCCAGTGGGTCCTCACAGCTGCCCAC
TGCATCAGGAACAAAAGCGTGATCTTGCTGGGTCGGCACAGCCTGTTTCATCCTGAAGAC
ACAGGCCAGGTATTTCAGGTCAGCCACAGCTTCCCACACCCGCTCTACGATATGAGCCTC
CTGAAGAATCGATTCCTCAGGCCAGGTGATGACTCCAGCCACGACCTCATGCTGCTCCGC
CTGTCAGAGCCTGCCGAGCTCACGGATGCTGTGAAGGTCATGGACCTGCCCACCCAGGAG
CCAGCACTGGGGACCACCTGCTACGCCTCAGGCTGGGGCAGCATTGAACCAGAGGAGTTC
TTGACCCCAAAGAAACTTCAGTGTGTGGACCTCCATGTTATTTCCAATGACGTGTGTGCG
CAAGTTCACCCTCAGAAGGTGACCAAGTTCATGCTGTGTGCTGGACGCTGGACAGGGGGC
AAAAGCACCTGCTCGGGTGATTCTGGGGGCCCACTTGTCTGTAATGGTGTGCTTCAAGGT
ATCACGTCATGGGGCAGTGAACCATGTGCCCTGCCCGAAAGGCCTTCCCTGTACACCAAG
GTGGTGCATTACCGGAAGTGGATCAAGGACACCATCGTGGCCAACCCC

Figure 5

CtxB:

CCTCAAAATATTACTGATTTGTGTGCAGAATACCACAACACACAAATATATACGCTAAAT

GATAAGATATTTTCGTATACAGAATCTCTAGCTGGAAAAAGAGAGATGGCTATCATTACT

TTTAAGAATGGTGCAATTTTTCAAGTAGAAGTACCAGGTAGTCAACATATAGATTCACAA

AAAAAAGCGATTGAAAGGATGAAGGATACCCTGAGGATTGCATATCTTACTGAAGCTAAA

GTCGAAAAGTTATGTGTATGGAATAATAAAACGCCTCATGCGATTGCCGCA

Figure 6

B-Raf KD:

GATGATTGGGAGATTCCTGATGGGCAGATTACAGTGGGACAAAGAAAGGGAAAGTGGCAT
GGTGATGTGGCAGTGAAAATGTTGAATGTGACAGCACCTACACCTCAGCAGTTACAAGCC
TTCAAAAATGAAGTAGGAGTACTCAGGAAAACACGACATGTGAATATCCTACTCTTCATG
GGCTATTCCACAAAGCCACAACTGGCTATTGTTACCCAGTGGTGTGAGGGCTCCAGCTTG
TATCACCATCTCCATATCATTGAGACCAAATTTGAGATGATCAAACTTATAGATATTGCA
CGACAGACTGCACAGGGCATGGATTACTTACACGCCAAGTCAATCATCCACAGAGACCTC
AAGAGTAATAATATATTTCTTCATGAAGACCTCACAGTAAAAATAGGTGATTTTGGTCTA
GCTACAGAGAAATCTCGATGGAGTGGGTCCCATCAGTTTGAACAGTTGTCTGGATCCATT
TTGTGGATGGCACCAGAAGTCATCAGAATGCAAGATAAAAATCCATACAGCTTTCAGTCA
GATGTATATGCATTTGGGATTGTTCTGTATGAATTGATGACTGGACAGTTACCTTATTCA
AACATCAACAACAGGGACCAGATAATTTTTATGGTGGGACGAGGATACCTGTCTCCAGAT
CTCAGTAAGGTACGGAGTAACTGTCCAAAAGCCATGAAGAGATTAATGGCAGAGTGCCTC
AAAAAGAAAAGAGATGAGAGACCACTCTTTCCCCAAATTCTCGCCTCTATTGAGCTGCTG
GCCCGCTCATTGCCAAAAATTCACCGCAGTGCATCAGAACCCTCCTTGAATCGGGCTGGT
TTCCAAACAGAGGATTTTAGTCTATATGCTTGTGCTTCTCCAAAAACACCCATCCAGGCA
GGGGGATATGGTGCGTTTCCTGTCCAC

Figure 7

```
B-Raf V600E:
CGATTTTGGCCTGGCGACCGAAAAAGCGGGCGATTTTGGCCTGGCGACCGAAAAAGCGGGC
GATTTTGGCCTGGCGACCGAAAAAGCGGGGC
```

Figure 8

Ctx - PSA - HlyA:

ATGCCAACAATAACCACTGCACAAATTAAAAGCACACTGCAGTCTGCAAAGCAATCCGCT
GCAAATAAATTGCACTCAGCAGGACAAAGCACGAAAGATGCATCACCTCAAAATATTACT
GATTTGTGTGCAGAATACCACAACACACAAATATATACGCTAAATGATAAGATATTTTCG
TATACAGAATCTCTAGCTGGAAAAAGAGAGATGGCTATCATTACTTTTAAGAATGGTGCA
ATTTTTCAAGTAGAAGTACCAGGTAGTCAACATATAGATTCACAAAAAAAAGCGATTGAA
AGGATGAAGGATACCCTGAGGATTGCATATCTTACTGAAGCTAAAGTCGAAAAGTTATGT
GTATGGAATAATAAAACGCCTCATGCGATTGCCGCAATGCCCGTGGGAGGCTGGGAGTGC
GAGAAGCATTCCCAACCCTGGCAGGTGCTTGTGGCCTCTCGTGGCAGGGCAGTCTGCGGC
GGTGTTCTGGTGCACCCCCAGTGGGTCCTCACAGCTGCCCACTGCATCAGGAACAAAAGC
GTGATCTTGCTGGGTCGGCACAGCCTGTTTCATCCTGAAGACACAGGCCAGGTATTTCAG
GTCAGCCACAGCTTCCCACACCCGCTCTACGATATGAGCCTCCTGAAGAATCGATTCCTC
AGGCCAGGTGATGACTCCAGCCACGACCTCATGCTGCTCCGCCTGTCAGAGCCTGCCGAG
CTCACGGATGCTGTGAAGGTCATGGACCTGCCCACCCAGGAGCCAGCACTGGGGACCACC
TGCTACGCCTCAGGCTGGGGCAGCATTGAACCAGAGGAGTTCTTGACCCCAAAGAAACTT
CAGTGTGTGGACCTCCATGTTATTTCCAATGACGTGTGTGCGCAAGTTCACCCTCAGAAG
GTGACCAAGTTCATGCTGTGTGCTGGACGCTGGACAGGGGGCAAAAGCACCTGCTCGGGT
GATTCTGGGGGCCCACTTGTCTGTAATGGTGTGCTTCAAGGTATCACGTCATGGGGCAGT
GAACCATGTGCCCTGCCCGAAAGGCCTTCCCTGTACACCAAGGTGGTGCATTACCGGAAG
TGGATCAAGGACACCATCGTGGCCAACCCCGGGCATGCATTAGCCTATGGAAGTCAGGGT
GATCTTAATCCATTAATTAATGAAATCAGCAAAATCATTTCAGCTGCAGGTAGCTTCGAT
GTTAAAGAGGAAAGAACTGCAGCTTCTTTATTGCAGTTGTCCGGTAATGCCAGTGATTTT
TCATATGGACGGAACTCAATAACCCTGACCACATCAGCATAA

Figure 9

```
Ctx - B-Raf V600E epitope - HlyA:
ATGACAACAATAACCACTGCACAAATTAAAAGCACACTGCAGTCTGCAAAGCAATCCGCT
GCAAATAAATTGCACTCAGCAGGACAAAGCACGAAAGATGCATCACCTCAAAATATTACT
GATTTGTGTGCAGAATACCACAACACACAAATACATACGCTAAATGATAAGATATTTTCG
TATACAGAATCTCTAGCTGGAAAAAGAGAGATGGCTATCATTACTTTTAAGAATGGTGCA
ACTTTTCAAGTAGAAGTACCAGGTAGTCAACATATAGATTCACAAAAAAAAGCGATTGAA
AGGATGAAGGATACCCTGAGGATTGCATATCTTACTGAAGCTAAAGTCGAAAAGTTATGT
GTATGGAATAATAAAACGCCTCATGCGATTGCCGCAATGCCCGGCGATTTTGGCCTGGCG
ACCGAAAAAGCGGGCGATTTTGGCCTGGCGACCGAAAAAGCGGGCGATTTTGGCCTGGCG
ACCGAAAAAGCGGGGCATGCATTAGCCTATGGAAGTCAGGGTGATCTTAATCCATTAATT
AATGAAATCAGCAAAATCATTTCAGCTGCAGGTAGCTTCGATGTTAAAGAGGAAAGAACT
GCAGCTTCTTTATTGCAGTTGTCCGGTAATGCCAGTGATTTTTCATATGGACGGAACTCA
ATAACCCTGACCACATCAGCATAA
```

Figure 10

Ctx - BRAF KD - HlyA:
ATGCCAACAATAACCACTGCACAAATTAAAAGCACACTGCAGTCTGCAAAGCAATCCGCT
GCAAATAAATTGCACTCAGCAGGACAAAGCACGAAAGATGCATCACCTCAAAATATTACT
GATTTGTGTGCAGAATACCACAACACACAAATATATACGCTAAATGATAAGATATTTTCG
TATACAGAATCTCTAGCTGGAAAAGAGAGATGGCTATCATTACTTTTAAGAATGGTGCA
ATTTTTCAAGTAGAAGTACCAGGTAGTCAACATATAGATTCACAAAAAAAGCGATTGAA
AGGATGAAGGATACCCTGAGGATTGCATATCTTACTGAAGCTAAAGTCGAAAAGTTATGT
GTATGGAATAATAAAACGCCTCATGCGATTGCCGCAATGCCCGATGATTGGGAGATTCCT
GATGGGCAGATTACAGTGGGACAAAGAAAGGGAAAGTGGCATGGTGATGTGGCAGTGAAA
ATGTTGAATGTGACAGCACCTACACCTCAGCAGTTACAAGCCTTCAAAAATGAAGTAGGA
GTACTCAGGAAAACACGACATGTGAATATCCTACTCTTCATGGGCTATTCCACAAAGCCA
CAACTGGCTATTGTTACCCAGTGGTGTGAGGGCTCCAGCTTGTATCACCATCTCCATATC
ATTGAGACCAAATTTGAGATGATCAAACTTATAGATATTGCACGACAGACTGCACAGGGC
ATGGATTACTTACACGCCAAGTCAATCATCCACAGAGACCTCAAGAGTAATAATATATTT
CTTCATGAAGACCTCACAGTAAAAATAGGTGATTTTGGTCTAGCTACAGAGAAATCTCGA
TGGAGTGGGTCCCATCAGTTTGAACAGTTGTCTGGATCCATTTTGTGGATGGCACCAGAA
GTCATCAGAATGCAAGATAAAAATCCATACAGCTTTCAGTCAGATGTATATGCATTTGGG
ATTGTTCTGTATGAATTGATGACTGGACAGTTACCTTATTCAAACATCAACAACAGGGAC
CAGATAATTTTTATGGTGGGACGAGGATACCTGTCTCCAGATCTCAGTAAGGTACGGAGT
AACTGTCCAAAAGCCATGAAGAGATTAATGGCAGAGTGCCTCAAAAAGAAAAGAGATGAG
AGACCACTCTTTCCCCAAATTCTCGCCTCTATTGAGCTGCTGGCCCGCTCATTGCCAAAA
ATTCACCGCAGTGCATCAGAACCCTCCTTGAATCGGGCTGGTTTCCAAACAGAGGATTTT
AGTCTATATGCTTGTGCTTCTCCAAAAACACCCATCCAGGCAGGGGGATATGGTGCGTTT
CCTGTCCACGGGCATGCATTAGCCTATGGAAGTCAGGGTGATCTTAATCCATTAATTAAT
GAAATCAGCAAAATCATTTCAGCTGCAGGTAGCTTCGATGTTAAAGAGGAAAGAACTGCA
GCTTCTTTATTGCAGTTGTCCGGTAATGCCAGTGATTTTTCATATGGACGGAACTCAATA
ACCCTGACCACATCAGCATAA

Figure 16

CtxB-HA12c-HlyA:

ATGACAACAATAACCACTGCACAAATTAAAAGCACACTGCAGTCTGCAAAGCAATCCGCT
GCAAATAAATTGCACTCAGCAGGACAAAGCACGAAAGATGCATCACCTCAAAATATTACT
GATTTGTGTGCAGAATACCACAACACACAAATACATACGCTAAATGATAAGATATTTTCG
TATACAGAATCTCTAGCTGGAAAAGAGAGATGGCTATCATTACTTTTAAGAATGGTGCA
ACTTTTCAAGTAGAAGTACCAGGTAGTCAACATATAGATTCACAAAAAAAAGCGATTGAA
AGGATGAAGGATACCCTGAGGATTGCATATCTTACTGAAGCTAAAGTCGAAAAGTTATGT
GTATGGAATAATAAAACGCCTCATGCGATTGCCGCAATGCCCATCTGTCAAATGGAGAAA
ATAGTGCTTCTTTTTGCAATAGTCAGTCTTGTTAAAAGTGATCAGATTTGCATTGGTTAC
CATGCAAACAACTCGACAGAGCAGGTTGACACAATAATGGAAAAGAACGTTACTGTTACA
CATGCCCAAGACATACTGGAAAAGACACACAACGGGAAGCTCTGCGATCTAGATGGAGTG
AAGCCTCTAATTTTGAGAGATTGTAGTGTAGCTGGATGGCTCCTCGGAAACCCAATGTGT
GACGAATTCATCAATGTGCCGGAATGGTCCTACATAGTGGAGAAGGCCAATCCAGTCAAT
GACCTCTGTTACCCAGGGGATTTCAATGACTATGAAGAATTGAAACACCTATTGAGCAGA
ATAAACCATTTTGAGAAAATTCAGATCATCCCCAAAAGTTCTTGGTCCAGTCATGAAGCC
TCATTAGGGGTGAGCTCAGCATGTCCATACCAGAGAAGTCCTCCTTTTTCAGAAATGTG
GTATGGCTTATCAAAAAGAACAGTACATACCCAACAATAAAGAGGAGCTACAATAATACC
AACCAAGAAGATCTTTTGGTACTGTGGGGATTCACCATCCTAATGATGCGGCAGAGCAG
ACAAAGCTCTATCAAAACCCAACCACCTATATTTCCGTTGGGACATCAACACTAAACCAG
AGATTGGTACCAAGAATAGCTACTAGATCCAAAGTAAACGGGCAAAGTGGAAGGATGGAG
TTCTTCTGGACAATTTTAAAACCGAATGATGCAATCAACTTCGAGAGTAATGGAAATTTC
ATTGCTCCAGAATATGCATACAAAATTGTCAAGAAGGGGACTCAACAATTATGAAAAGT
GAATTGGAATATGGTAACTGCAACACCAAGTGTCAAACTCCAATGGGGGCGATAAACTCT
AGTATGCCATTCCACAATATACACCCTCTCACCATCGGGGAATGCCCCAAATATGTGAAA
TCAAACAGATTAGTCCTTGCGACTGGGCTCAGAAATAGCCCTCAAAGAGAGAGAAGAAGA
AAAAGAGAGGATTATTTGGAGCTATAGCAGGTTTTATAGAGGGAGGATGGCAGGGAATG
GTAGATGGTTGGTATGGGTACCACCATAGCAATGAGCAGGGGAGTGGGTACGCTGCAGAC
AAAGAATCCACTCAAAAGGCAATAGATGGAGTCACCAATAAGGTCAACTCGATCATTGAC
AAAATGAACACTCAGTTTGAGGCCGTTGGAAGGGAATTTAACAACTTAGAAAGGAGAATA
GAGAATTTAAACAAGAAGATGGAAGACGGGTTCCTAGATGTCTGGACTTATAATGCTGAA
CTTCTGGTTCTCATGGAAAATGAGAGAACTCTAGACTTTCATGACTCAAATGTCAAGAAC
CTTTACGACAAGGTCCGACTACAGCTTAGGGATAATGCAAAGGAACTGGGTAACGGTTGT
TTCGAGTTCTATCATAAATGTGATAATGAATGTATGGAAAGTGTAAGAAACGGAACGTAT
GACTACCCGCAGTATTCAGAAGAAGCAAGACTAAAAAGAGAGGAAATAAGTGGAGTAGGG
CATGCATTAGCCTATGGAAGTCAGGGTGATCTTAATCCATTAATTAATGAAATCAGCAAA
ATCATTTCAGCTGCAGGTAGCTTCGATGTTAAAGAGGAAAGAACTGCAGCTTCTTTATTG
CAGTTGTCCGGTAATGCCAGTGATTTTTCATATGGACGGAACTCAATAACCCTGACCACA
TCAGCATAA

Figure 18

Vector pMKhly1 (full sequence):

```
LOCUS       pMO Kan        12672 bp    DNA     CIRCULAR SYN      13-NOV-2006
DEFINITION  pMO Kan secretion Vector
ACCESSION   pMO Kan
KEYWORDS    .
SOURCE      Unknown.
  ORGANISM  Unknown
            Unclassified.
REFERENCE   1  (bases 1 to 12672)
  AUTHORS   Self
  JOURNAL   Unpublished.
FEATURES             Location/Qualifiers
     CDS             2503..3015
                     /gene="HlyC"
     CDS             3027..3128
                     /gene="5hlyA nter"
     CDS             3129..3311
                     /gene="3'hlyA"
                     /product="hlyA'"
     CDS             3383..5506
                     /gene="hlyB"
                     /product="hlyB"
     CDS             5525..6961
                     /gene="hlyD"
                     /product="hlyD"
     CDS             complement (11029..11823)
                     /gene="KM-Res"
BASE COUNT     3420 a   2832 c   3095 g   3325 t
ORIGIN
        1 GAATTCCAAG CGAAGTCCAT CCCCCTCCCT CTTGATTACA AGGGTGATAA TTATTATTCG
       61 CATTTGTGTG GTAATGGGAT AGAAAGGAAT GGATAGAAAA AGAACAAAAT TAGTATAGCA
      121 ATAGATATGC CCACTGCATT GAATACTTAC AGGGCATTAT TTTATTATGT TTAAATTGAA
      181 GTGGTCTCTG GTTTGATTTA TTTGTTATTC AAGGGGGCTG TTTGGAGATC GGAAAATTCT
      241 GTACGTTAAG TGTATTATTT AACCAGTTTC GATGCGTAAC AGATTGATTT TGCGTCAGCG
      301 GTTATCGCTT TTAAGTTGTT GCTCTTGCGC TATCGCGTTT AGGTTATCCG ATTAAAGTCA
      361 AATTTCCTGA AAATGCTGTA TAGCGCGGGA GTGCACCTTA TAGCTGTAGG TAAGTATGTT
      421 CAAAAAATAG TCTTGCCGTA CAATAATTTT CCATATCCAA ACTCACTCCT TCAAGATTCT
      481 GGTCCCGGTT TACGGGTAGT TTCCGGAAGG GCGGTAGCAT GCTGATTCAA ACTGCAAGAT
      541 GAAACATTGT CGGAGTTGGA TGGAATTAAG TCATGGCTAT AGCATTTGGG CGTGCATAAC
      601 AAAATTGGTC CTCATATTTT AGAGTATGAT TGCATATTCA CTAATATTTT TACTTTCTGA
      661 TGCGTGGTGG CATCATGCTT TATGAGATAA ACAATCCTGG TAGACTAGCC CCCTGAATCT
      721 CCAGACAACC AATATCACTT ATTTAAGTGA TAGTCTTAAT ACTAGTTTTT AGACTAGTCA
      781 TTGGAGAACA GATGATTGAT GTCTTAGGAT CGGAGAAACG CAGACGGCGT ACTACACAGG
      841 AAAAGATCGC TATCGTTCAG CAGAGCTTTG AACCGGGAAT GACGGTCTCC CTTGTTGCCC
      901 GGCAACATGG TGTGGCAGCC AGCCAGCTAT TTCTCTGGCG CAAGCAATAC CAGGAGGGAA
      961 GTCTTACTGC TGTGGCTGCC GGAGAACAGG TCGTTCCTGC CTCTGAACTT GCTGCCGCCA
     1021 TGAAGCAGAT TAAAGAGCTC CAGCGCCTGC TCGGCAAAAA AACGATGGAA AATGAACTCC
     1081 TTAAAGAAGC CGTTGAATAT GGGCGAGCAA AAAAGTGGAT AGCGCACGCG CCCTTATTGC
     1141 CCGGGGATGG GGAGTAAGCT TCGTCAGCCG TTGTCTCCGG GTGTCGCGTG CGCAGTTGCA
     1201 CGTCATTCTC AGACGAACCG ATGACTGGAA GGACGGCCGC CGCAGCCGTC ACACGGATGA
     1261 TACGGATGTG CTTCGCCGTA TACATCATGT TATCGGAGAG CTGCCCACAT ATGGTTATCG
     1321 TCGGGTATGG GCGCTGCTTC GCAGACAAAC AGAACTTGAT GGTATGCCTG CGATCAATGC
     1381 CAAATGTGTT TACCGGATCA TGTGCCAGAA TGCGCTGTTG CTTGAGCGAA AACCCGCTGT
     1441 ACCGCCATCG AAACGGGCAC ATACCGGCAG AGTGGCTGTG AAAGAAAGTA ATCAGCGATG
     1501 GTGCTCTGAC GGGTTTGAGT TCCGCTGTGA TAACGGAGAA AAACTGCGGG TCACGTTCGC
```

Figure 18 -continued

```
1561 GCTGGACTGC TGTGATCGTG AGGCACTGCA CTGGGCGGTC ACAACGGGTG GCTTCAACAG
1621 TGAAACAGTA CAGGACGTCA TGCTGGGAGC AGTGGAACGC CGCTTTGGCA GCGAGCTTCC
1681 GGCGTCTCCA GTGGAGTGGC TGACGGATAA TGGTTCATGC TACCGGGCGA ATGAAACACG
1741 TCAGTTCGCC AGGATGTTGG GACTTGAACC GAAGAACACG GCAGTGCGGA GTCCGGAGAG
1801 TAACGGAATA ACAGAGAGCT TCGTGAAAAC GATAAAGCGT GATTACATAA GTATCATGCC
1861 CAAACCAGAC GGGTTAACGG CAGCAAAGAA CCTTGCAGAG GCGTTCGAGC ATTATAACGA
1921 ATGGCATCCG CATAGTGCGC TGGGTTATCG CTCGCCACGG GAATATCTGC GGCAGCGGGC
1981 CAGTAATGGG TTAAGTGATA ACAGGTATCT GGAAATATAG GGGCAAATCC ACCTGGTCAT
2041 TATCTGGAAT TTGACGAAGT GTGATAACTG GTATAGCCAG ATTAATCTAA ACCTTTGTCT
2101 GACAAAATCA GATAAAGAAG AGTAGTTCAA AAGACAACTC GTGGACTCTC ATTCAGAGAG
2161 ATAGGCGTTA CCAAAATTTG TTTGGAACTG AACAAGAAAA TTGTATTTGT GTAACTATAA
2221 TCTTAATGTA AAATAAAAGA CACCAGTTCT GTAGAATATG CTTATTGAAG AGAGTGTAAT
2281 AATAATTTTA TATAGATGTT GTACAAAGAA CAGGAATGAG TAATTATTTA TGCTTGATGT
2341 TTTTTGACTC TTGCTTTTTA TAGTTATTAT TTTTAAGTTA GTCAGCGCAA TAAAAACTTG
2401 CTTTTAATAT TAATGCGAGT TATGACATTA AACGGAAGAA ACATAAAGGC ATATTTTTGC
2461 CACAATATTT AATCATATAA TTTAAGTTGT AGTGAGTTTA TTATGAATAT AAACAAACCA
2521 TTAGAGATTC TTGGGCATGT ATCCTGGCTA TGGGCCAGTT CTCCACTACA CAGAAACTGG
2581 CCAGTATCTT TGTTTGCAAT AAATGTATTA CCCGCAATAC AGGCTAACCA ATATGTTTTA
2641 TTAACCCGGG ATGATTACCC TGTCGCGTAT TGTAGTTGGG CTAATTTAAG TTTAGAAAAT
2701 GAAATTAAAT ATCTTAATGA TGTTACCTCA TTAGTTGCAG AAGACTGGAC TTCAGGTGAT
2761 CGTAAATGGT TCATTGACTG GATTGCTCCT TTCGGGGATA ACGGTGCCCT GTACAAATAT
2821 ATGCGAAAAA AATTCCCTGA TGAACTATTC AGAGCCATCA GGGTGGATCC CAAAACTCAT
2881 GTTGGTAAAG TATCAGAATT TCATGGAGGT AAAATTGATA ACAGTTAGC GAATAAAATT
2941 TTTAAACAAT ATCACCACGA GTTAATAACT GAAGTAAAAA GAAAGTCAGA TTTTAATTTT
3001 TCATTAACTG GTTAAGAGGT AATTAAATGC CAACAATAAC CACTGCACAA ATTAAAAGCA
3061 CACTGCAGTC TGCAAAGCAA TCCGCTGCAA ATAAATTGCA CTCAGCAGGA CAAAGCACGA
3121 AAGATGCATT AGCCTATGGA AGTCAGGGTG ATCTTAATCC ATTAATTAAT GAAATCAGCA
3181 AAATCATTTC AGCTGCAGGT AGCTTCGATG TTAAAGAGGA AAGAACTGCA GCTTCTTTAT
3241 TGCAGTTGTC CGGTAATGCC AGTGATTTTT CATATGGACG GAACTCAATA ACCCTGACCA
3301 CATCAGCATA ATATATTAAT TTAAATGATA GCAATCTTAC TGGGCTGTGC CACATAAGAT
3361 TGCTATTTTT TTTGGAGTCA TAATGGATTC TTGTCATAAA ATTGATTATG GGTTATACGC
3421 CCTGGAGATT TTAGCCCAAT ACCATAACGT CTCTGTTAAC CCGGAAGAAA TTAAACATAG
3481 ATTTGATACA GACGGGACAG GTCTGGGATT AACGTCATGG TTGCTTGCTG CGAAATCTTT
3541 AGAACTAAAG GTAAAACAGG TAAAAAAAAC AATTGATCGA TTAAACTTTA TTTTTCTGCC
3601 CGCATTAGTC TGGAGAGAGG ATGGACGTCA TTTTATTCTG ACTAAAATCA GCAAAGAAGT
3661 AAACAGATAT CTTATTTTTG ATTTGGAGCA GCGAAATCCC CGTGTTCTCG AACAGTCTGA
3721 GTTTGAGGCG TTATATCAGG GGCATATTAT TCTTATTACT TCCCGTTCTT CTGTTACCGG
3781 GAAACTGGCA AAATTTGACT TTACCTGGTT TATTCCTGCC ATTATAAAAT ACAGGAGAAT
3841 ATTTATTGAA ACCCTTGTTG TATCTGTTTT TTTACAATTA TTTGCATTAA TAACCCCCCT
3901 TTTTTTCCAG GTGGTTATGG ACAAAGTATT AGTGCACAGG GGGTTTTCAA CCCTTAATGT
3961 TATTACTGTT GCATTATCTG TTGTAGTGGT GTTTGAGATT ATACTCAGCG GTTTAAGAAC
4021 TTACATTTTT GCACATAGTA CAAGTCGGAT TGATGTTGAG TTGGGTGCCA AACTCTTCCG
4081 GCATTTACTG GCGCTACCGA TCTCTTATTT TGAGAGTCGT CGTGTTGGTG ATACTGTTGC
4141 GAGGGTAAGA GAATTAGACC AGATCCGTAA TTTTCTGACA GGACAGGCAT AACATCTGT
4201 TTTGGACTTA TTATTTTCAC TCATATTTTT TGCGGTAATG TGGTATTACA GCCCAAAGCT
4261 TACTCTGGTG ATCTTATTTT CGCTGCCTTG TTATGCTGCA TGGTCTGTTT TTATTAGCCC
4321 CATTTTGCGA CGTCGCCTTG ATGATAAGTT TTCACGGAAT GCGGATAATC AATCTTTCCT
4381 GGTGGAATCA GTAACGGCGA TTAACACTAT AAAAGCTATG GCAGTCTCAC CTCAGATGAC
4441 GAACATATGG GACAAACAAT TGGCAGGATA TGTTGCTGCA GGCTTTAAAG TGACAGTATT
4501 AGCAACCATT GGTCAACAAG GAATACAGTT AATACAAAAG ACTGTTATGA TCATCAACCT
4561 ATGGTTGGGA GCACACCTGG TTATTTCCGG GGATTTAAGT ATTGGTCAGT TAATTGCTTT
4621 TAATATGCTT GCTGGTCAGA TTGTTGCACC GGTTATTCGC CTTGCACAAA TCTGGCAGGA
4681 TTTCCAGCAG GTTGGTATAT CAGTTACCCG CCTTGGTGAT GTGCTTAACT CTCCAACTGA
4741 AAGTTATCAT GGGAAACTGA CATTGCCGGA AATTAATGGT GATATCACTT TTCGTAATAT
4801 CCGGTTTCGC TATAAACCTG ATTCTCCGGT TATTTTGGAC AATATCAATC TTAGTATTAA
4861 GCAGGGGGAG GTTATTGGTA TTGTCGGACG TTCTGGTTCA GGAAAAAGCA CATTAACTAA
4921 ATTAATTCAA CGTTTTTATA TTCCTGAAAA TGGCCAGGTA TTAATTGATG GACATGATCT
```

Figure 18 -continued

```
4981 TGCGTTGGCT GATCCTAACT GGTTACGTCG TCAGGTGGGG GTTGTGTTGC AGGACAATGT
5041 GCTGCTTAAT CGCAGTATTA TTGATAATAT TTCACTGGCT AATCCTGGCA TGTCCGTCGA
5101 AAAAGTTATT TATGCAGCGA AATTAGCAGG CGCTCATGAT TTTATTTCTG ATTTGCGTGA
5161 GGGGTATAAC ACCATTGTCG GGGAACAGGG GGCAGGATTA TCCGGAGGTC AACGTCAACG
5221 CATCGCAATT GCAAGGGCGC TGGTAACAA CCCTAAAATA CTCATTTTTG ATGAAGCAAC
5281 CAGTGCTCTG GATTATGAGT CGGAGCATGT CATCATGCGC AATATGCACA AAATATGTAA
5341 GGGCAGAACG GTTATAATCA TTGCTCATCG TCTGTCTACA GTAAAAAATG CAGACCGCAT
5401 TATTGTCATG GAAAAAGGGA AAATTGTTGA ACAGGGTAAA CATAAGGAGC TGCTTTCTGA
5461 ACCGGAAAGT TTATACAGTT ACTTATATCA GTTACAGTCA GACTAACAGA AAGAACAGAA
5521 GAATATGAAA ACATGGTTAA TGGGGTTCAG CGAGTTCCTG TTGCGCTATA AACTTGTCTG
5581 GAGTGAAACA TGGAAAATCC GGAAGCAATT AGATACTCCG GTACGTGAAA AGGACGAAAA
5641 TGAATTCTTA CCCGCTCATC TGGAATTAAT TGAAACGCCA GTATCCGAC GGCCGCGTCT
5701 GGTTGCTTAT TTTATTATGG GGTTTCTGGT TATTGCTTTT ATTTTATCTG TTTTAGGCCA
5761 AGTGGAAATT GTTGCCACTG CAAATGGGAA ATTAACACAC AGTGGGCGTA GTAAAGAAAT
5821 TAAACCTATT GAAAACTCAA TAGTTAAAGA AATTATCGTA AAAGAAGGAG AGTCAGTCCG
5881 GAAAGGGGAT GTGTTATTAA AGCTTACAGC ACTGGGAGCT GAAGCTGATA CGTTAAAAAC
5941 ACAGTCATCA CTGTTACAGG CCAGGCTGGA ACAAACTCGG TATCAAATTC TGAGCAGGTC
6001 AATTGAATTA AATAAACTAC CTGAACTAAA GCTTCCTGAT GAGCCTTATT TTCAGAATGT
6061 ATCTGAAGAG GAAGTACTGC GTTAACTTC TTTGATAAAA GAACAGTTTT CCACATGGCA
6121 AAATCAGAAG TATCAAAAAG AACTGAATTT GGATAAGAAA AGAGCAGAGC GATTAACAGT
6181 ACTTGCCCGT ATAAACCGTT ATGAAAATTT ATCAAGGGTT GAAAAAGCC GTCTGGATGA
6241 TTTCAGTAGT TTATTGCATA AACAGGCAAT TGCAAAACAT GCTGTACTTG AGCAGGAGAA
6301 TAAATATGTC GAAGCAGTAA ATGAATTACG AGTTTATAAA TCACAACTGG AGCAAATTGA
6361 GAGTGAGATA TTGTCTGCAA AAGAAGAATA TCAGCTTGTT ACGCAGCTTT TTAAAAATGA
6421 AATTTTAGAT AAGCTAAGAC AAACAACAGA CAACATTGGG TTATTAACTC TGGAATTAGC
6481 GAAAAATGAA GAGCGTCAAC AGGCTTCAGT AATCAGGGCC CCAGTTTCGG GAAAAGTTCA
6541 GCAACTGAAG GTTCATACTG AAGGTGGGGT TGTTACAACA GCGGAAACAC TGATGGTCAT
6601 CGTTCCGGAA GATGACACGC TGGAGGTTAC TGCTCTGGTA CAAAATAAAG ATATTGGTTT
6661 TATTAACGTC GGGCAGAATG CCATCATTAA AGTGGAGGCA TTTCCTTATA CACGATATGG
6721 TTATCTGGTG GGTAAGGTGA AAAATATAAA TTTAGATGCA ATAGAAGACC AGAGACTGGG
6781 ACTTGTTTTT AATGTTATTA TTTCTATTGA AGAGAATTGT TTGTCAACCG GAATAAAAA
6841 CATTCCATTA AGCTCGGGTA TGGCAGTCAC TGCAGAAATA AAGACAGGTA TGCGAAGTGT
6901 AATCAGTTAT CTTCTTAGTC CTTTAGAAGA GTCAGTAACA GAAAGTTTAC GTGAGCGTTA
6961 AGTTTCAGAA GTCCAGTATT TGCTGCTATA CGTGCTGCGT GGCACTTGCC GTCTGAACGG
7021 CATTGATCCG GAAGCCAAGT CAAACAACAG CGTGATGAGC GTCAGGGCAA AACACCAAGG
7081 CTCTCTCGAT GACACCAGAA CAAATTGAAA TACGTGAGCT GAGGAAAAAG CTACCGAGTT
7141 CTTGATGTTG GACTCCCTGA ACAGTTCTCT GTAATCGGGA AACTCAGGAC GCGTTATCCT
7201 GTGGTCACAC TCTGCCATGT GTTTAGGGTT CATCACAGCA GCTACAGATA CTGGTAAAAC
7261 CGTCCTGAAA AACCAGACGG CAGACGGGCT GTATTACGTA GTCAGGTACT TGAGCTACAT
7321 GGCATCAGTC ACGGTTTGGC CGGAGCAAGA CGTATCCACA CAATGGCAAC CCGGAGAGGT
7381 GTCAGCGCCA GTGATATAAG ACGGTTAACG GTTAAAAATC GTGGCGTTGA CAACATCCCA
7441 GTGGACTGAG GTCACACAGG CCTGGCAGCA TTCCTCTTCC GGCCGGATGA CCCGGATTTC
7501 ACGGGGAAAG TACGCCGATA ACAGTTTACG GGCTGAAGAT TGGCGTAGGG AGGATAGCAG
7561 ACGTTTTGCC GCCCCATTG TCTGGAGTTG GGTGAGAAGG CATCATTTCA CCAACACCAA
7621 CATTTCACAG TTACACCCCA CAGCTACATG AAGCGCTTCC ATGAATTATC GCTTTGATTT
7681 ATCATGTTAA AATAGCTCTA CACGGTTGGT TCAGGATTGC GCACCGAAAC CCTCTAAAAT
7741 CCACTGACGC GCCTGCGAAT TATCCAGCAC CGCGCCTTTC GAGATCCTCT ACGCCGGACG
7801 CATCGTGGCC GGCATCACCG GCGCCACAGG TGCGGTTGCT GGCGCCTATA TCGCCGACAT
7861 CACCGATGGG GAAGATCGGG CTCGCCACTT CGGGCTCATG AGCGCTTGTT TCGGCGTGGG
7921 TATGGTGGCA GGCCCCGTGG CCGGGGGACT GTTGGGCGCC ATCTCCTTGC ATGCACCATT
7981 CCTTGCGGCG GCGGTGCTCA ACGGCCTCAA CCTACTACTG GGCTGCTTCC TAATGCAGGA
8041 GTCGCATAAG GGAGAGCGTC GACCGATGCC CTTGAGACC TTCAACCCAG TCAGCTCCTT
8101 CCGGTGGGCG CGGGGCATGA CTATCGTCGC CGCACTTATG ACTGTCTTCT TTATCATGCA
8161 ACTCGTAGGA CAGGTGCCGG CAGCGCTCTG GGTCATTTTC GGCGAGGACC GCTTTCGCTG
8221 GAGCGCGACG ATGATCGGCC TGTCGCTTGC GGTATTCGGA ATCTTGCACG CCCTCGCTCA
8281 AGCCTTCGTC ACTGGTCCCG CCACCAAACG TTTCGGCGAG AAGCAGGCCA TTATCGCCGG
8341 CATGGCGGCC GACGCGCTGG GCTACGTCTT GCTGGCGTTC GCGACGCGAG GCTGGATGGC
```

Figure 18 -continued

```
 8401 CTTCCCCATT ATGATTCTTC TCGCTTCCGG CGGCATCGGG ATGCCCGCGT TGCAGGCCAT
 8461 GCTGTCCAGG CAGGTAGATG ACGACCATCA GGGACAGCTT CAAGGATCGC TCGCGGCTCT
 8521 TACCAGCCTA ACTTCGATCA TTGGACCGCT GATCGTCACG GCGATTTATG CCGCCTCGGC
 8581 GAGCACATGG AACGGGTTGG CATGGATTGT AGGCGCCGCC CTATACCTTG TCTGCCTCCC
 8641 CGCGTTGCGT CGCGGTGCAT GGAGCCGGGC CACCTCGACC TGAATGGAAG CCGGCGGCAC
 8701 CTCGCTAACG GATTCACCAC TCCAAGAATT GGAGCCAATC AATTCTTGCG GAGAACTGTG
 8761 AATGCGCAAA CCAACCCTTG GCAGAACATA TCCATCGCGT CCGCCATCTC CAGCAGCCGC
 8821 ACGCGGCGCA TCTCGGGCAG CGTTGGGTCC TGGCCACGGG TGCGCATGAT CGTGCTCCTG
 8881 TCGTTGAGGA CCCGGCTAGG CTGGCGGGGT TGCCTTACTG GTTAGCAGAA TGAATCACCG
 8941 ATACGCGAGC GAACGTGAAG CGACTGCTGC TGCAAAACGT CTGCGACCTG AGCAACAACA
 9001 TGAATGGTCT TCGGTTTCCG TGTTTCGTAA AGTCTGGAAA CGCGGAAGTC AGCGCCCTGC
 9061 ACCATTATGT TCCGGATCTG CATCGCAGGA TGCTGCTGGC TACCCTGTGG AACACCTACA
 9121 TCTGTATTAA CGAAGCGCTG GCATTGACCC TGAGTGATTT TTCTCTGGTC CCGCCGCATC
 9181 CATACCGCCA GTTGTTTACC CTCACAACGT TCCAGTAACC GGGCATGTTC ATCATCAGTA
 9241 ACCCGTATCG TGAGCATCCT CTCTCGTTTC ATCGGTATCA TTACCCCCAT GAACAGAAAT
 9301 CCCCCTTACA CGGAGGCATC AGTGACCAAA CAGGAAAAAA CCGCCCTTAA CATGGCCCGC
 9361 TTTATCAGAA GCCAGACATT AACGCTTCTG GAGAAACTCA ACGAGCTGGA CGCGGATGAA
 9421 CAGGCAGACA TCTGTGAATC GCTTCACGAC CACGCTGATG AGCTTTACCG CAGCTGCCTC
 9481 GCGCGTTTCG GTGATGACGG TGAAAACCTC TGACACATGC AGCTCCCGGA GACGGTCACA
 9541 GCTTGTCTGT AAGCGGATGC CGGGAGCAGA CAAGCCCGTC AGGGCGCGTC AGCGGGTGTT
 9601 GGCGGGTGTC GGGGCGCAGC CATGACCCAG TCACGTAGCG ATAGCGGAGT GTATACTGGC
 9661 TTAACTATGC GGCATCAGAG CAGATTGTAC TGAGAGTGCA CCATATGCGG TGTGAAATAC
 9721 CGCACAGATG CGTAAGGAGA AAATACCGCA TCAGGCGCTC TTCCGCTTCC TCGCTCACTG
 9781 ACTCGCTGCG CTCGGTCGTT CGGCTGCGGC GAGCGGTATC AGCTCACTCA AAGGCGGTAA
 9841 TACGGTTATC CACAGAATCA GGGGATAACG CAGGAAAGAA CATGTGAGCA AAAGGCCAGC
 9901 AAAAGGCCAG GAACCGTAAA AAGGCCGCGT TGCTGGCGTT TTTCCATAGG CTCCGCCCCC
 9961 CTGACGAGCA TCACAAAAAT CGACGCTCAA GTCAGAGGTG GCGAAACCCG ACAGGACTAT
10021 AAAGATACCA GGCGTTTCCC CCTGGAAGCT CCCTCGTGCG CTCTCCTGTT CCGACCCTGC
10081 CGCTTACCGG ATACCTGTCC GCCTTTCTCC CTTCGGGAAG CGTGGCGCTT TCTCATAGCT
10141 CACGCTGTAG GTATCTCAGT TCGGTGTAGG TCGTTCGCTC CAAGCTGGGC TGTGTGCACG
10201 AACCCCCCGT TCAGCCCGAC CGCTGCGCCT TATCCGGTAA CTATCGTCTT GAGTCCAACC
10261 CGGTAAGACA CGACTTATCG CCACTGGCAG CAGCCACTGG TAACAGGATT AGCAGAGCGA
10321 GGTATGTAGG CGGTGCTACA GAGTTCTTGA AGTGGTGGCC TAACTACGGC TACACTAGAA
10381 GGACAGTATT TGGTATCTGC GCTCTGCTGA AGCCAGTTAC CTTCGGAAAA AGAGTTGGTA
10441 GCTCTTGATC CGGCAAACAA ACCACCGCTG GTAGCGGTGG TTTTTTTGTT TGCAAGCAGC
10501 AGATTACGCG CAGAAAAAAA GGATCTCAAG AAGATCCTTT GATCTTTTCT ACGGGGTCTG
10561 ACGCTCAGTG GAACGAAAAC TCACGTTAAG GGATTTTGGT CATGAGATTA TCAAAAAGGA
10621 TCTTCACCTA GATCCTTTTA AATTAAAAAT GAAGTTTTAA ATCAATCTAA AGTATATATG
10681 AGTAAACTTG GTCTGACAGT TACCAATGCT TAATCAGTGA GGCACCTATC TCAGCGATCT
10741 GTCTATTTCG TTCATCCATA GTTGCCTGAC TCCCCATATG AATATCCTCC TTAGTTCCTA
10801 TTCCGAAGTT CCTATTCTCT AGAAAGTATA GGAACTTCAG AGCGCTTTTG AAGCTGGGGT
10861 GGGCGAAGAA CTCCAGCATG AGATCCCGC GCTGGAGGAT CATCCAGCCG GCGTCCCGGA
10921 AAACGATTCC GAAGCCCAAC CTTTCATAGA AGGCGGCGGT GGAATCGAAA TCTCGTGATG
10981 GCAGGTTGGG CGTCGCTTGG TCGGTCATTT CGAACCCCAG AGTCCGCTC AGAAGAACTC
11041 GTCAAGAAGG CGATAGAAGG CGATGCGCTG CGAATCGGGA GCGGCGATAC CGTAAAGCAC
11101 GAGGAAGCGG TCAGCCCATT CGCCGCCAAG CTCTTCAGCA ATATCACGGG TAGCCAACGC
11161 TATGTCCTGA TAGCGGTCCG CCACACCCAG CCGGCCACAG TCGATGAATC CAGAAAAGCG
11221 GCCATTTTCC ACCATGATAT CGGCAAGCA GGCATCGCCA TGGGTCACGA CGAGATCCTC
11281 GCCGTCGGGC ATGCGCGCCT TGAGCCTGGC GAACAGTTCG GCTGGCGCGA GCCCCTGATG
11341 CTCTTCGTCC AGATCATCCT GATCGACAAG ACCGGCTTCC ATCCGAGTAC GTGCTCGCTC
11401 GATGCGATGT TTCGCTTGGT GGTCGAATGG GCAGGTAGCC GGATCAAGCG TATGCAGCCG
11461 CCGCATTGCA TCAGCCATGA TGGATACTTT CTCGGCAGGA GCAAGGTGAG ATGACAGGAG
11521 ATCCTGCCCC GGCACTTCGC CCAATAGCAG CCAGTCCCTT CCCGCTTCAG TGACAACGTC
11581 GAGCACAGCT GCGCAAGGAA CGCCCGTCGT GGCCAGCCAC GATAGCCGCG CTGCCTCGTC
11641 CTGCAGTTCA TTCAGGGCAC CGGACAGGTC GGTCTTGACA AAAGAACCG GGCGCCCCTG
11701 CGCTGACAGC CGGAACACGG CGGCATCAGA GCAGCCGATT GTCTGTTGTG CCCAGTCATA
11761 GCCGAATAGC CTCTCCACCC AAGCGGCCGG AGAACCTGCG TGCAATCCAT CTTGTTCAAT
```

Figure 18 -continued

```
11821 CATGCGAAAC GATCCTCATC CTGTCTCTTG ATCAGATCTT GATCCCCTGC GCCATCAGAT
11881 CCTTGGCGGC AAGAAAGCCA TCCAGTTTAC TTTGCAGGGC TTCCCAACCT TACCAGAGGG
11941 CGCCCCAGCT GGCAATTCCG GTTCGCTTGC TGTCCATAAA ACCGCCCAGT CTAGCTATCG
12001 CCATGTAAGC CCACTGCAAG CTACCTGCTT TCTCTTTGCG CTTGCGTTTT CCCTTGTCCA
12061 GATAGCCCAG TAGCTGACAT TCATCCGGGG TCAGCACCGT TTCTGCGGAC TGGCTTTCTA
12121 CGTGTTCCGC TTCCTTTAGC AGCCCTTGCG CCCTGAGTGC TTGCGGCAGC GTGGGGATC
12181 TTGAAGTTCC TATTCCGAAG TTCCTATTCT CTAGAAAGTA TAGGAACTTC GAAGCAGCTC
12241 CAGCCTACAC CAAAAAGGG AATAAGGGCG ACACGGAAAT GTTAATACT CATACTCTTC
12301 CTTTTTCAAT ATTATTGAAG CATTTATCAG GGTTATTGTC TCATGAGCGG ATACATATTT
12361 GAATGTATTT AGAAAAATAA ACAAATAGGG GTTCCGCGCA CATTTCCCCG AAAAGTGCCA
12421 CCTGACGTCT AAGAAACCAT TATTATCATG ACATTAACCT ATAAAATAG GCGTATCACG
12481 AGGCCCTTTC GTCTTCAAGA ATTCTCATGT TTGACAGCTT ATCATCGATG ACATTATTT
12541 TTGTGGAGCC GGAGGAAACA GACCAGACGG TTCAGATGAG GCGCTTACCA CCAGAACCGC
12601 TGTTGTCCCA CCATTCTGGC GATTCCCAAA CGCTATTTGG ATAAAAGTA GCCTTAACGT
12661 GGTTTATTTT CC
//
```

MICROORGANISMS AS CARRIERS OF NUCLEOTIDE SEQUENCES CODING FOR ANTIGENS AND PROTEIN TOXINS, PROCESS OF MANUFACTURING AND USES THEREOF

CROSS-REFERENCE TO RELATED APPLICATIONS

This application claims priority under 35 U.S.C. §119(e) to U.S. provisional application No. 60/865,484, filed Nov. 13, 2006 and to U.S. provisional application No. 60/939,140, filed May 21, 2007; priority is also claimed to EP 06123974.5, filed Nov. 13, 2006. Each of these priority applications is hereby incorporated by reference in its entirety.

BACKGROUND OF THE INVENTION

1. Field of the Invention

The invention relates to microorganisms as carriers of heterogeneous nucleotide sequences coding for antigens and protein toxins, a process of manufacturing thereof as well as corresponding plasmids or expression vectors. These microorganisms can be used as medicaments, in particular as tumor vaccines for the treatment of various tumors.

2. Description of the Related Art

Immunotherapy of cancer represents a promising option of tumor-treatment. A multiplicity of clinical trials using different approaches concentrates on its efficiency in patients. In principle, a distinction is drawn between passive and active immunotherapy.

Active immunotherapy aims at the induction of a vaccine-related tumor-specific immune response. The latter is currently being clinically probed using several different approaches. For instance there are so called whole-cell vaccines, whose feed stock are tumor cells that are either directly obtained from the patient (autologous) or derived from appropriate cell lines (heterologous). These cells are then usually inactivated, differentially manipulated and (re)applied to the patient.

In contrast, antigen-specific vaccines contain one (or more) tumor-specific antigens, parts of the antigen or the specific antigen-coding DNA as well as so called anti-idiotype vaccines. Normally these vaccines are not isolated, but injected in combination with an appropriate carrier. Hence, on one hand different classic adjuvants are utilized, but likewise combinations with biological immuno-stimulants such as cytokines.

For the purpose of immuno-stimulation, approaches are being applied, that contain antigen associated with immuno-stimulants, such as tetanus toxin. Furthermore, there exist attempts, applying antigens in combination with dendritic cells. And finally there are several attempts with recombinant live-vaccines with viral or bacterial carriers.

Fusion proteins of bacterial toxins, such as tetanus toxin, shiga toxin, lethal toxin or cholera toxin, as adjuvants with an antigen are utilized as vaccines especially against infections for quite some time (Freytag and Clements, 1999). Additionally, native toxins, often merged with a target-cell specific molecule, such as a cell surface molecule of tumor cells, are also used in order to destroy target cells.

At this, fusion proteins with the native toxin, that generally comprise an enzymatic unit and a protein-binding domain, develop their optimum effect in use as adjuvants (Freytag and Clements, 1999). By means of these vaccines a satisfying immune response is obtained even after mucosal and particularly after oral immunization. The trouble with these fusion proteins is, that native toxins are highly toxic and therefore cannot be established in humans (Holmgren et al., 2005).

A whole string of research is thus occupied with detoxification of toxins that at the same time preserve the adjuvant-effect. However, since in most cases the adjuvant-effect coincides with enzymatic-activity, which is responsible for the toxic effect (Lycke et al., 1992), detoxification cannot be performed in a straightforward way, even if it appears to be possible for some toxins that do not lose their enzymatic, adjuvant activity (Hormozi et al., 1999; Lycke et al., 1992).

In the case of cholera toxin (CT) several attempts of detoxification are pursued (Agren et al., 1999; Byun et al., 2001; Eriksson et al., 2004; Kweon et al., 2002; Sanchez et al., 2002), for which, however, the use as mucosal adjuvant prevails (Freytag and Clements). Therefore, above all, efficient induction of an antibody response (primarily mucosal IgA), which receive an increased toxin-related MHC class II restricted T-cell support, is the main prerequisite for a mucosal adjuvant for a vaccine that consists of protein-antigen and a fused or co-applied toxin (Freytag and Clements).

As for cholera toxin, especially its B-subunit (CtxB) is tested as adjuvant since it is responsible for binding to the GM-1 receptor and does not show toxic effects when isolated (Holmgren et al.). Protein fusions with CtxB are characterized by primary induction of so called Th2 immune responses. These are T-cell responses, which are mainly characterized by cytokines, such as IL-4 or IL-6, and which primarily cause induction of antibodies, but which do not at all or at most restrictedly initiate a cellular immune response, particularly of cytotoxic T cells (CTL) (Holmgren et al.).

In addition, CtxB as mucosal adjuvant induces protein-antigen systemic tolerance. Systemic tolerance describes the depletion or inactivation of antigen-specific lymphocytes, in particular T-cells or B-cells. This kind of approach is therefore inapplicable for the induction of a systemic immune response (Holmgren et al.).

In contrast to mucosal application intraperitoneal or subcutaneous application of a toxin-antigen fusion protein is able to induce systemic as well as low cytotoxic responses. This has indeed been utilized for tumor-vaccination in model systems (refer to e.g. (Becerra et al., 2003)). However such response is also obtained with the purified antigen itself and is primarily depending on the adjuvant used. Apart from the fact that the measured CTL responses in the model are rather low, there was no evidence that the protection was even depending on these effects. Moreover, the antigen was not applied orally, but only by direct injection (s.c., i.d., i.m., i.p.) of the antigen.

Antigen proteins fused to a detoxified toxin are generally ineffective if applied as oral tumor vaccine. The main reasons are, if present at all, only low induction of a systemic immune response or even, in the case of CtxB, induction of systemic tolerance as well as induction of mucosally restricted antibody and Th2 type immune responses.

McSorley et al., for instance, showed that nasal immunization with a CtxB-antigen fusion protein (which for a tumor vaccine represents the preferred way of inducing a systemic response) preferably tolerates and therefore inactivates Th1 cells, whereas Th2 cells are not influenced (McSorley et al., 1998). Th2 responses are characterized by T-helper cells that predominantly produce IL-4 or IL-6. These cytokines are particularly responsible for the initiation of antibody production by B-cells, which provide protection in the case of most conventional vaccines. In contrast, Th1 T-cells mostly secrete IL-2 and IFN-gamma, thus cytokines, which play a role in cellular immune response. Depending on the objective of an immunization strategy it is of crucial importance, whether an antibody dominated Th2 immune response (so-called Th2 bias) or a cellular dominated Th1 response (so called Th1 bias) is initiated.

By contrast, systemic induction of a Th1 dominated cellular immune response with IFN-gamma producing T-helper cells and induction of cytotoxic T-cells (CTL) is indispensable for tumor immunotherapy.

The prior art shows that toxins can function as adjuvants. Especially cholera toxin (CT) shows a strong adjuvant effect. However, this effect is significantly attenuated as soon as the toxin is detoxified. Regarding its subunit CtxB, oral application even induces systemic tolerance. This problem can be partially avoided by nasal application. However, if nasal administration is applied, other problems arise, in particular such as the ones associated with CtxB subunit concerning the expression of GM-1 receptor in the brain (van Ginkel et al., 2000), which are reflected in an increasing risk of particular severe side effects (Mutsch et al., 2004).

To overcome these problems, it may be possible to generate recombinant live-vaccines that co-express toxins and (heterologous) antigens. This option has already been pursued with regard to infection vaccines, i.e. vaccines that are directed against a specific pathogen, for instance the tuberculosis pathogen, and are meant to induce immunity against that pathogen.

In the course of developing such infection vaccines, recombinant toxins fused to appropriate (heterologous) antigens have already been generated, using several recombinant bacterial strains that are administered orally, either as alive or inactivated vaccine. In most cases, the generated strains only expressed a recombinant toxin. Hence, these approaches primarily aimed at solely immunizing against the toxin itself (induction of an antibody response) and, consequently, the toxin expressing strain (pathogen). These kinds of vaccines are not suitable for use as potential tumor vaccines in tumor therapy and, not surprisingly, corresponding trials do not mention any such possible application (Reveneau et al., 2002) (Vertiev et al., 2001) (Freytag and Clements, 1999; Jackson et al., 1996).

With respect to such infection vaccines, in the course of induction of an antibody response the toxin does not function as adjuvant, it is the induction of a mucosal antibody immune response which prevails. These infection vaccine trials include no or only a very weak systemic immune response. In contrast to tumor vaccines, such vaccines do not pursue an induction of cellular immune response, especially of cytotoxic T-cells. The toxin expressing bacterial pathogens normally show an extracellular live pattern and therefore do not contribute to an activation of CTL, i.e. the protection conferred by such infection vaccines is CTL independent.

The following bacterial strains have been used in the mentioned infection vaccine trials: recombinant *Lactobacilli* (Reveneau et al., 2002), *Listeria* (Vertiev et al., 2001), *Bacillus anthracis* (Mendelson et al., 2005; Mesnage et al., 1999), *Shigellae* (Anderson et al., 2000; Tzschaschel et al., 1996b), *E. coli* (Walker et al., 1992), *Vibrio* (Butterton et al., 1995; Chen et al., 1998; Thungapathra et al., 1999) and *Salmonella* (Jackson et al., 1996).

In addition, it was tried to enhance mucosal immune responses by surface presentation (Konieczny et al., 2000) or secretion of the toxin as heterologous antigen (*Salmonella, Shigellae*: (Garmory et al., 2003; Orr et al., 1999; Su et al., 1992; Tzschaschel et al., 1996a; Tzschaschel et al., 1996b), *Yersinia*: (Sory and Cornelis, 1990), *Vibrio* (Ryan et al., 1997a), *E. coli*: (Zhu et al., 2006)). However, in these additional cases the toxins themselves represent the antigens to which the immune response is directed to.

Thus, it has to be noted that the toxins neither function as adjuvants nor did the describing studies intend to express toxins as fusion proteins with an additional separate (heterologous) antigen. Moreover, fusions proteins with CT or CtxB were neither generated with these systems nor were they suggested.

Consequently, fusion proteins mentioned in above cited documents are fusion proteins of a peptidic secretion signal, such as HlyA, and a toxin protein, but not fusion proteins, consisting of a toxin and a (heterologous) antigen.

The primary objective of these studies was to merely obtain an optimum mucosal immune response (Tzschaschel et al., 1996a). Induction of a systemic immune response was not pursued. Yet if measured at all, analyses of systemic immune responses were restricted to antibodies (particularly systemic IgA) only, since protection in these kind of models is mainly mediated by antibodies (compare e.g. [31]). Induction of a systemic cellular immune response, in particular a cytotoxic T-cell response, is not described. The fusion with a secretion signal was primarily used in order to increase the solubility of the toxins and enhance their stability, respectively, since a strong, mere cytoplasmatic expression often results in the production of insoluble aggregates (Gentschev et al., 2002a).

In this respect, some authors observe that fusion proteins with a secretion signal cause a fast cytoplasmatic degradation (Tzschaschel et al., 1996a), whereas others observe a stabilization (Orr et al., 1999). The prior art, hence, is contradictory here. So far, previous experiments with secreted toxins (toxin+secretion signal) are above all aimed at increasing stability, which obviously was not achieved in all cases.

One reason certainly is found in variable expression intensity and plasmid stability. Tzschaschel et al. describe, that the plasmid system used, is highly instable and above all, without selection, is merely found in a few bacteria. As a possible solution the authors use chromosomal integration via a mini-transposon (Tzschaschel et al., 1996a; Tzschaschel et al., 1996b).

However, such a system possesses several disadvantages. On one hand the point of integration is not defined, which can lead to an undesired phenotype alteration of the host strain (e.g. increased/decreased expression of flanking genes). On the other hand the expected expression level using a single genomic copy is only low, which has a negative effect on immunogenicity. After all, chromosomal transposon integration is relatively instable, for it leads quite frequently to spontaneous excisions at the sides of the repetitive elements.

As mentioned above, the prior art is contradictory concerning the stability of a secreted heterologous toxin.

Garmory et al. even assume, that secretion of a heterologous antigen does not have any special benefit with regard to immunogenicity (Garmory et al., 2002; Roland et al., 2005). In other cases increased systemic antibody response to a secreted toxin after intravenous administration has indeed been observed, but not after oral application. All the contrary, oral application is even indirectly put into question (Roland et al., 2005).

Eventually, studies with a gram-positive strain (*Lactobacillus plantarum*) which produces tetanus toxin showed no significant difference in induction of a systemic antibody response compared to strains that secrete the toxin, present it bound to their membrane or contain the toxin cytoplasmatically (Reveneau et al., 2002).

Systemic cellular immune responses, in particular cytotoxic T-cell responses, and the resulting protection, were not studied nor described.

The above cited prior art of toxin-based infection vaccines thus cannot declare if a secretion of toxin used as adjuvant represents an advantage, concerning the induction of a systemic (cellular) immune response. All the contrary, above cited studies rather point the stability problem out and mention the missing benefit of a secreted heterologous toxin. Fusion proteins, consisting of secretion signal, toxin and heterologous antigen, are not at all described or suggested.

In above passages the prior art was presented, that describes bacterial carriers which express toxins heterologously and can be used as infection vaccines. In the cited examples mainly modifications regarding the expression or stability of toxins and their solubility were carried out, for instance insertion of strong expression promoter or fusion of a toxin to a secretion signal.

Other authors have also studied genetic fusions of toxins to heterologous antigens in live-vaccines. In these cases the toxin was mostly used as adjuvant. In some cases (e. g. (Brossier et al., 2000)) the heterologous antigen functioned as adjuvant and the toxin as proper antigen.

However, it is important to note, that in the mentioned cases, expression of the toxin-antigen gene fusion construct exclusively took place cytoplasmatically or periplasmatically. The toxin-antigen construct was neither fused to an additional secretion signal (which would lead to its complete secretion) nor was it directly secreted.

In the course of these toxin-antigen gene fusion constructs, recombinant *E. coli* (Clemens et al., 2004), *Bacillus anthracis* (Brossier et al., 2000), *Shigella* (Koprowski et al., 2000; Ranallo et al., 2005; Zheng et al., 2005) and *Vibrio* strains (Silva et al., 2003) were used. For *Salmonella* (summarized in (Garmory et al., 2002)), too, fusions of CT variants with antigens (Hajishengallis et al., 1996; Huang et al., 2000) or other toxins with antigens (Barry et al., 1996; Cardenas and Clements, 1993; Chabalgoity et al., 1997; Chabalgoity et al., 1996; Chabalgoity et al., 2000; Chabalgoity et al., 1995; Chacon et al., 1996; Jagusztyn-Krynicka et al., 1993; Khan et al., 1994a; Khan et al., 1994b; Lee et al., 2000; Pogonka et al., 2003; Schodel et al., 1990; Smerdou et al., 1996; Ward et al., 1999; Wu et al., 2000) have been described.

In the majority of these cases the main focus was on induction of a mucosal (antibody) immune response and for the induction of a systemic immune response, only subcutaneous, but not oral application was chosen [36].

Some work with *Salmonella* as supporter strain are limited to a mere characterization of the strain (Gomez-Duarte et al., 1995; Jagusztyn-Krynicka et al., 1993), others only analyze the mucosal and/or systemic antibody response and/or protection (Barry et al., 1996; Cardenas and Clements, 1993; Dunstan et al., 2003; Hajishengallis et al., 1996; Harokopakis et al., 1997; Khan et al., 1994a; Khan et al., 1994b; Pogonka et al., 2003; Smerdou et al., 1996; Somner et al., 1999). In all these cases, in which incidentally a fusion between antigen and tetanus toxin was used and which are exclusively used as infection vaccines, systemic cellular immune responses, particularly cytotoxic T-Cell responses, have not been studied.

Therefore, from an immunological point of view, no conclusions about a potential use as a tumor vaccine can be drawn from those studies, since their focuses were set on antibody mediated effects as infection vaccines.

Investigations that include an isotype analysis of the immune response studied appear to be more relevant. In fact, cellular immune responses are not directly measured in these cases, but the isotype profile of the antibody response allows a conclusion on the Th1/Th2 bias of the immune response. Antibody isotypes like IgG1 are associated with Th2 responses and isotypes like IgG2a are associated with Th1 responses. As already mentioned, Th1 responses are cellular dominated immune responses, whereas Th2 responses mainly represent humoral antibody-driven responses. Still, those studies do neither describe tumor vaccines nor do they suggest any use as anti-tumor agent.

One infection vaccine study based on *Salmonella* as carrier, which expresses a tetanus-toxin antigen fusion protein has been realized in dogs. The low antibody responses that were induced in dogs, show a Th1 bias, regarding the antibody profile, hence, a response that rather correlates with a cellular type immune response (Chabalgoity et al., 2000). Admittedly, dog immunology is only scarcely researched, and therefore it is not clear to which extent a dog's antibody profile can give information about a Th1 bias.

Studies in mice, performed by the same group, using comparable constructs, however showed an antibody profile with the same level for IgG1 as for IgG2a, which would indicate a mixed Th1/Th2 response.

Interestingly, an existing immunity against tetanus toxin, as it is found in most humans due to previous immunizations, causes another relatively strong induction of IgG 1, whereas IgG2a is hardly induced. This clearly indicates a distinct Th2 bias (Chabalgoity et al., 1995). For this reason, a tetanus toxin based live-vaccine as tumor vaccine is rather harmful for human use. For it can be expected, that a strong Th2 antibody-dominated response is induced in the majority of these patients, who show a tetanus toxin specific response.

Only few studies also analyze cellular immune response and compare genetic constructs with and without toxin fusion. In one case, for instance, a fusion of an antigen with and without tetanus toxin has been compared in *Salmonella* (Lee et al.). There, the tetanus toxin antigen fusion construct mainly increased the total antibody level, whereas the Th1/Th2 profile was hardly altered. Even the antigen specific CD4$^+$ T cell secretion of typical Th1 cytokines, such as IFN-gamma and IL-2, respectively, only showed weak divergence. In an earlier study by the same group, cellular IFN-gamma levels had been measured, too. However, no comparison drawn with constructs without tetanus toxin (Chabalgoity et al.). Other studies with different gram-negative bacterial carriers, like *Shigella* (Koprowski et al.; Ranallo et al.; Zheng et al.) or *Vibrio* (Campos et al.; Ryan et al.), did not analyze isotypes and cellular immune responses, respectively, either.

In summary, it can be stated, that the studies mentioned clearly focus on the induction of an antibody-driven humoral immune response. Indeed, genetic toxin antigen constructs are used, but these are not provided with a secretion signal nor are they directly secreted. On no account, however, systemic cellular immune responses, in particular cytotoxic T-cell responses, were analyzed. What is more, such cellular cytotoxic T-cell responses cannot be concluded from humoral antibody response and cannot be detected if the antibody response is Th1/Th2-composed.

However, it is exactly these cellular cytotoxic T cell immune responses which are crucial for use in tumor vaccination therapy.

Hence, in terms of toxin-antigen fusions, which are restricted to mucosal infection vaccines only, the state-of-the-art does not allow any statement about possible use of any such constructs as tumor vaccines.

As already mentioned, expression of the genetic fusion constructs is realized without assistance of a secretion system. Toxins and toxin antigen constructs, respectively, are usually located cytoplasmatically as well as periplasmatically, i.e. between the two membranes. In order to induce an efficient cellular immune response the toxin must be freely accessible for the antigen-presenting cell (APC). Usually, native toxin is produced in the periplasm of gram-negative bacteria. This is sufficient for mere mucosal immune responses, because periplasmatic toxins can escape from the periplasm in the colon and consequently are accessible, too (Hunt and Hardy, 1991). This does not count, however, if the carrier targets antigen-presenting cells outside the colon, such as e.g. Peyer's Patches or lymphatic organs like lymph nodes or spleen.

In principle, two factors are crucial for the efficiency of a tumor vaccine: induction of a cellular immune response of the Th1-type and participation of components of the innate immune system, such as NK cells, NKT-cells and gamma-delta T cells, which play an important role for the efficiency of tumor therapy (Dunn et al., 2004).

The importance of these components of the innate immune systems lies on multiple levels. Properly activated NK- and gamma-delta T cells are able to locally produce large amounts of IFN-gamma. This interferon, which is also produced by specific Th1 polarized T-cells, has multiple functions, relevant to tumor therapy. One of its central functions is the inhibition of angiogenesis, which cuts off the tumor's oxygen and nutrients supply and de facto starves the tumor. Furthermore, NK cells possess receptors, which recognize MHC class I molecules. If these molecules are present on a cell, NK cells are inhibited.

As for a vaccine, which induces specific cytotoxic T-cells, tumor cells can be killed by these CTLs. If the tumor cell loses its capability to express MHC class I molecules, which occurs quite frequently in tumors, specific cytotoxic T-cells are ineffective. Hence, in this case, inhibition of NK cells is stopped, and they are able to eliminate tumor cells directly.

Consequently, it would be ideal if a tumor vaccine induces both components efficiently. There are contradictory data concerning the Th1-Th2 bias of a fused toxin adjuvant. As discussed earlier, toxin antigen fusion constructs applied in an isolated fashion obviously induce a strong Th2 polarized immune response. Some authors still describe a low Th2 bias for live-carriers; other authors see a slight Th1 bias.

However, these data again are exclusively based on non-secreted constructs. Induction of innate immunity by means of such kinds of infection vaccines has never been compared nor contemplated.

As already mentioned, the main reason is that the existing vaccines are mucosal infection vaccines, not tumor vaccines. Therefore, induction of Th1 immune responses, CTL immune responses and responses of the innate immune system were not in the focus. In contrast, regarding tumor vaccines, induction of these immune responses is indispensable.

Interestingly, in cell biology native toxins are commonly used as inhibitors of signaling pathways. So among others it has been shown, that native *pertussis* toxin, but not cholera toxin, is able to inhibit a particular apoptosis pattern of NK cells (Ramirez et al., 1994). A different research study was able to show that cholera toxin, but not its B-subunit, blocks specific NK cell functions (Poggi et al., 1996). Native *pertussis* toxin is used in order to inhibit chemotaxis of lymphocytes (Spangrude et al., 1985). Even if these studies do not deal with tumor vaccination, a person skilled in the art would conclude, that the use of toxins as tumor vaccines would be harmful, because the response of the innate immune system, crucial for tumor therapy, is rather inhibited than induced.

Other research studies were able to show that toxins like native *pertussis* toxin (but not inactive *pertussis* toxin) efficiently induce components of the innate immune system. Regarding immunotherapy against tumors, this would mean that, if at all, native toxins would need to be employed. However, due to toxicity reasons such kind of administration is infeasible. Further, such induction would inevitably lead to a Th2 directed secondary immune response, which in turn would be deleterious for tumor therapy (Boyd et al., 2005).

Consequently, concerning the induction of an innate immune response, the prior art does not describe nor contemplates tumor vaccination. All the contrary, critical analysis of the literature even militates against the use of toxins in tumor therapy.

Interesting, though, is an analysis of the synergistic effect of toxins or their subunits with other stimulants, such as immune stimulating DNA oligonucleotides with hypomethylated CpG motives (CpG ODN) (Holmgren et al., 2005) or liposaccharides (LPS). In the case of LPS primarily the induction of monocytes appears to be increased mainly through the B-subunit of the toxins, whereas it is inhibited by the toxin as a whole (holotoxin) (Hajishengallis et al., 2004). However, these studies exclusively rely on the use of purified toxin-antigen-fusion constructs, to which substances like LPS or CpG are added as adjuvants. Furthermore, analysis there is only carried out on macrophages, which induce an adaptive immune response, but do not attack tumours directly. Hence, these studies have no significance regarding the induction of components of the innate immune system, in particular NK cells, which can attack tumors directly.

Other studies, however, show that NK cells can be activated and chemotacticly attracted by toxins like *Pseudomonas aeruginosa* Exotoxin A (Muhlen et al., 2004). Depending on the experimental system, Th1 responses can also be induced, although a suppression of NK cells and Th1 responses thereby mostly occurs (Michalkiewicz et al., 1999). However, these assays primarily aim at the analysis of the hepatotoxicity of Enterotoxin A and do not refer to tumor vaccination. Interestingly, the effects are highly dose-dependent, and only a slight change of dose can invert the effects. Yet, the authors could not reveal which response effectively occurs in vivo. As a consequence, the data do not provide a prediction which effects may occur if a toxin or even a detoxified toxin is used as adjuvant.

All in all, the immune response strongly depends on the particular system applied. In most cases, a mucosal anti-infection vaccine aims at the local manipulation of the immune system at the mucosa, in order to induce an efficient mucosal immune response (Lycke, 2005). However, these studies do not include the development of a tumor vaccine. In addition, those studies lack information about the induction of systemic cellular immune responses, particularly responses of cytotoxic T-cells, which are essential for tumor vaccination.

It has already been shown, that secretion of a heterologous antigen confers advantages for a systemic immune response (Hess et al., 1996). However, the secreted antigens described were not secreted toxin-antigen constructs; toxins or subunits thereof were not used. The thereby attainable immune responses in a transgenic tumor model were highly limited, too (Gentschev et al., 2005). Indeed, weak antibody and cytotoxic T-cell responses could be induced in this case, that partially protected from a tumor progression. However, not only the immune responses themselves, but the protection itself was limited. Likewise, these tumor vaccination studies lack a comparison with non-secreted constructs. Furthermore, the comparative studies were not carried out in the context of tumor vaccination (Hess et al., 1996) and are in contrast to further studies, that do not see any advantage with regard to secretion (Garmory et al., 2002; Roland et al., 2005).

In summary and as previously mentioned, the prior art is highly contradictory regarding secretion and, all in all, does not give any hint towards potential advantages of secreted toxin-antigen constructs in tumor therapy. All the contrary, critical analysis of the existing literature rather disagrees with such kind of use.

Bacterial toxins (Todar, 2002): At a chemical level, there are two types of bacterial toxins, lipopolysaccharides, which are associated with the cell walls of gram-negative bacteria, and proteins, which are released from bacterial cells and may act at tissue sites remote from the site of bacterial growth. The cell-associated lipopolysaccharide (LPS) toxins are referred to as endotoxins and the extracellular diffusible toxins are referred to as exotoxins.

Exotoxins are typically soluble proteins secreted by living bacteria during exponential growth but in some cases they are released by lysis of the bacterial cell. The production of the toxin is generally specific to a particular bacterial species that produces the disease associated with the toxin (e.g. only *Clostridium tetani* produces tetanus toxin; only *Corynebacterium diphtheriae* produces the diphtheria toxin). Both gram-positive and gram-negative bacteria produce soluble protein toxins.

In general there exist three classes of protein (exo-) toxins: (i) type I toxins (super-antigens), that bind to the host cell surface and modulate the immune response but are not translocated into the cell, (ii) type II toxins (pore-forming toxins), which act on the host cell membrane and make the host cell leak and die, and (iii) type III toxins (A-B toxins), which bind to the host cell via one specific receptor, are translocated into the cell, become active therein an modify proteins or other components of the host cell.

As indicated above, type III toxins, acting intracellularly with regard to host cells, consist of two components: one component (subunit A) is responsible for the enzymatic activity of the toxin; the other component (subunit B) is concerned with binding to a specific receptor on the host cell membrane and transferring the enzyme across the membrane. The enzymatic component is not active until it is released from the native (A+B) toxin. Isolated A subunits are enzymatically active but lack binding and cell entry capability. Isolated B subunits may bind to target cells (and even block the binding of the native toxin), but they are non-toxic.

There are a variety of ways that toxin subunits may be synthesized and arranged: A+B indicates that the toxin is synthesized and secreted as two separate protein subunits that interact at the target cell surface; A-B or A-5B or AB5 indicates that the A and B subunits are synthesized separately, but associated by noncovalent bonds during secretion and binding to their target; 5B or B5 indicates that the binding domain of the protein is composed of 5 identical subunits. AB or A/B denotes a toxin synthesized as a single polypeptide, divided into A and B domains, which may be separated by proteolytic cleavage. Examples of AB or A/B toxins are Diphtheria Toxin, Exotoxin A, *Botulinum* toxin and Tetanus Toxin. Examples of A-5B or AB5 toxins are Cholera Toxin and Shiga Toxin, whereas Anthrax Toxin LF and Anthrax Toxin EF are examples of A-B toxins.

Further relevant documents of the prior art comprise the following:

Michl et al. describe the use of bacteria and bacterial toxins as therapeutic agents for solid tumors. Toxin-Antigen fusion constructs are disclosed as well as bacterial targeting of such construct. Use of diphtheria toxin (DT), pseudomonas exotoxin A (PE) and *clostridium perfringens* enterotoxin (CPE) is studied. However, the authors do neither mention the use of cholera toxin nor do they show or render obvious secretion of bacteria-delivered toxin-antigen fusion constructs (Michl and Gress, 2004).

Lahiri gives an overview about different bacterial toxins and discuss their manifold uses. Although the author mentions toxin-antigen fusion proteins he is silent about cholera toxin and bacterial targeting of secreted toxin-antigen fusion constructs (Lahiri, 2000).

Lavelle et al. disclose molecules of infectious agents as immunomodulatory drugs. The authors also mention cholera toxin-antigen fusion proteins, but such constructs are only applied directly as proteins and not by means of genetically modified live vaccines (Lavelle et al., 2004).

WO 01/74383 is directed to chimeric antigen-enterotoxin mucosal immunogens and also mentions the use of cholera toxin subunits A2 and B. Such chimeric immunogens, however, comprises always A2 and B subunits at the same time and are intended for use in mucosal immunization but not in tumor therapy.

WO 02/077249 describes non-virulent *Yersinia enterocolitica* mutant strains for the delivery of heterologous proteins to specific mutated target cells. Use of cholera toxin subunit A1 is also mentioned but the patent document is silent about secretion and refers to the treatment of infections and infectious states only.

WO 2004/018630 discloses recombinant double stranded RNA phages encoding a double stranded eukaryotic expression cassette. Although cholera toxin subunit A is mentioned, the document is not of further relevance.

Holmgren et al. give a brief overview about the field of mucosal immunization and adjuvants. They discuss among others the effects of cholera toxin as mucosal adjuvants but do not disclose information about genetic expression systems or live vaccines and are also silent about tumor therapy (Holmgren et al., 2003).

Holmgren and Czerkinsky also give an overview about mucosal immunity and vaccines. However, this article is restricted to anti-infectives only and does not discuss or render obvious possible uses in the field of tumor therapy (Holmgren and Czerkinsky, 2005).

Another review by Freytag and Clements discusses mucosal adjuvants for application in anti-infective immunotherapy. Although cholera toxin is mentioned as mucosal adjuvants the authors are silent about secreted toxin-antigen constructs and tumor therapy as a possible field of administration (Freytag and Clements, 2005).

Shaw and Starnbach describe the use of modified bacterial toxins to deliver vaccine antigens. However, the article does not mention cholera toxin and further is limited to direct application of toxin-antigen fusion proteins for vaccination reasons (Shaw and Starnbach, 2003).

WO 03/072789 is directed to microorganisms as carriers of nucleotide sequences coding for cell antigens used for the treatment of tumors. Although the patent document mentions secretion and use in the field of tumor therapy it is silent about bacterial toxins and fusion proteins at all.

Gentschev, Dietrich and Goebel as well as Gentschev et al. describe bacterial targeting and its use in tumor vaccine development. However, these two documents do not mention the use of bacterial toxins and fusion proteins in tumor therapy (Gentschev et al., 2002a; Gentschev et al., 2002b).

WO 98/23763 discloses *Vibrio cholerae* cells expressing *E. coli* hemolysin B and D subunits along with a fusion polypeptide that includes a heterologous antigen fused to hylA. Further described is a *Vibrio cholerae* vaccine strain that expresses cholera toxin subunit B and a fusion polypeptide of a secretory signal sequence, heterologous antigen and choleratoxin A2 subunit. Last, a fusion polypeptide that includes cholera toxin B subunit fused to an antigenic portion of *C. difficile* toxin A or toxin B subunit is disclosed. However, the patent application does not mention use of a fusion protein of protein toxin plus a heterologous non-protein toxin antigen in tumor therapy.

Dietrich and co-workers discuss two vaccine delivery tools—haemolysin A and listeriolysin—that can be used for cell-mediated immunity. However, no protein toxin—heterologous antigen fusion proteins or co-expression is mentioned (Dietrich et al., 2003).

Gentschev et al. describe the use of the alpha-hemolysin secretion system of Escherichia coli for antigen delivery in the Salmonella typhi Ty21a vaccine strain. However, the authors do not mention the use of bacterial toxins and fusion proteins in tumor therapy (Gentschev et al., 2004).

WO 02/47727 is directed to therapeutic agents comprising a B-subunit of a protein toxin. The document only discloses fusion proteins of CtxB and EtxB with viral antigen. No bacterial vaccine or bacterial vaccine delivery is mentioned.

Cheng-hua S and co-workers describe a gene fusion of cholera toxin B subunit and HBV PreS2 epitope and the antigenicity of the fusion protein in direct immunization studies. However, no bacterial vaccine or bacterial vaccine delivery is mentioned (Cheng-hua et al., 1995).

Sanchez et al. disclose that cholera toxin B-subunit gene enhances mucosal immunoglobulin A, Th1-type and $CD8^+$ cytotoxic responses when co-administered intradermally with a DNA vaccine (Sanchez et al., 2004). However, in this approach the authors use DNA as a carrier which acts as a Th1 promoting adjuvant on its own. In addition, the proteins are produced by host cells and not delivered directly or via abacterial carrier and are therefore directly available for eukaryotic cells.

WO 01/29233 is directed to chimeric immunogenic compositions and nucleic acids encoding them. However, no bacterial vaccine or bacterial vaccine delivery is mentioned.

WO 2007/044406 relates to methods for stimulating an immune response using a bacterial antigen delivery system that is based on a SopE bearing type III secretion signal. However, the patent application does not mention the use of bacterial toxins and fusion proteins in tumor therapy.

In summary, it can be concluded from the prior art that native toxins cannot be established for use in humans due to their strong toxicity. Further, their application in tumor therapy would be harmful because the response of the innate immune system, in particular that of NK cells, would be inhibited. However, it is this immune response which is a crucial component for a successful tumor therapy since tumor cells very frequently lose their capability to express MHC class I molecules and therefore are resistant to CTL recognition and attack.

Use of the detoxified toxin subunits, on the other hand, alone or fused to (heterologous) antigen proteins results in a strongly attenuated adjuvant effect an(/or even an induced systemic tolerance of the immune system as well as mucosally restricted antibody and Th2 type immune responses.

Furthermore, secretion of (heterologous) antigen-toxin fusion proteins, which is only described in the course of anti-infection vaccines (i.e. targeting the antigen or even the toxin itself), is said to not only display no advantages over cytoplasmatic expression, but to be generally rather unsuitable.

All in all, neither a tumor therapeutic approach is presented nor were a systemic induction of a Th1 dominated cellular immune response with IFN-gamma producing T-helper cells, an induction of CTL nor the activation of the innate immune system described or achieved, all of which are indispensable for tumor therapy.

BRIEF DESCRIPTION OF THE INVENTION

One object of the present invention is to provide novel tumor vaccines by means of which a strong systemic cellular immune system response is induced and an efficient tumor therapy can be achieved.

This object of the present invention has been surprisingly solved in one aspect by providing a microorganism as a carrier of nucleotide sequences coding for antigens and protein toxins comprising the following components:

(I) at least one nucleotide sequence coding for at least one complete or partial antigen of at least one wild-type or mutated protein; and (II) at least one nucleotide sequence coding for at least one protein toxin and/or at least one protein toxin subunit; and (III) a) at least one nucleotide sequence coding for at least one transport system which enables the expression of the expression products of component (I) and component (II) on the outer surface of the microorganism and/or enables the secretion of the expression products of component (I) and component (II); and/or coding for at least one signal sequence which enables the secretion of the expression products of component (I) and component (II); and/or b) optionally, at least one nucleotide sequence coding for at least one protein for lysing the microorganism in the cytosol of mammalian cells and for intracellularly releasing plasmids or expression vectors, which are contained in the lysed microorganism; and (IV) at least one nucleotide sequence for at least one activation sequence for the expression of one or more of components (I) to (III), wherein said activation sequence can be activated in the microorganism and/or is tissue cell-specific, tumor cell-specific, macrophage-specific, dendrite-specific, lymphocyte-specific, function-specific or non-cell-specific;

wherein any of components (I) to (IV) can be present either once or several times and if a component of components (I) to (IV) is present several times it can independently from each other be either identical or different.

In a preferred embodiment, a microorganism comprising above components (I) to (IV) is provided, wherein the component (I) and component (II) are not identical, that is component (I) does not code for at least one nucleotide sequence coding for at least one protein toxin and/or at least one protein toxin subunit.

The term "tissue cell-specific" in connection with component (IV) in the course of the present invention refers to activation sequence(s) which are specifically activated in target tissue cells, such as hormone dependent promoters in prostatic tissues for instance.

The term "tumor cell-specific" in connection with component (IV) in the course of the present invention refers to activation sequence(s) which are specifically activated in tumor cells, such as promoter elements activated by the action of tumor specific oncogenes.

The term "macrophage-specific" in connection with component (IV) in the course of the present invention refers to activation sequence(s) which are specifically activated in macrophages, such as promoter elements which encode for-macrophage specific genes, for instance the gene encoding for F4/80.

The term "dendrite-specific" in connection with component (IV) in the course of the present invention refers to activation sequence(s) which are specifically activated in dendritic cells, such as promoter elements controlling the expression of B7.1. The terms "dendrite-specific" and "dendriticcell-specific" are equivalent, i.e. they have the same meaning and both refer to dendritic cells.

The term "lymphocyte-specific" in connection with component (IV) in the course of the present invention refers to elements which are specifically activated in cells of the lymphocytic lineage like promoter elements regulating the expression of CD3 molecules in T-cells or promoter elements regulating the expression of CD20 in mature B-cells.

The term "function-specific" in connection with component (IV) in the course of the present invention refers to activation sequence(s) which are specifically activated in cellular context, e.g. in tumor cells which have lost p53 expression, or activation sequence(s) which are activated within bacteria depending on the context, e.g. cellular localization or oxygen pressure.

The term "non-cell-specific" in connection with component (IV) in the course of the present invention refers to activation sequence(s) which are ubiquitously active, such as constitutively active bacterial promoters.

The term "nucleotide sequence" in the course of the present invention refers to dsDNA, ssDNA, dsRNA, ssRNA or dsDNA/RNA hybrids. Preferred is dsDNA.

The term "antigen" in the course of the present invention refers to molecules that react with antibodies, i.e. that are able to generate antibodies. Some antigens do not, by themselves, elicit antibody production; only those that can induce antibody production are called immunogens. For the purpose of the present invention, all kinds of known antigens are intended to be comprised. It is within the knowledge of a person skilled in the art to retrieve the necessary information about potential antigens by means of databases and/or experimental screening without undue burden. Examples of antigens are among others cell antigens, tissue-cell specific antigens (e.g. tissue cells from which the tumor derives), cell protein antigens, viral antigens, viral protein antigens and the like. Preferred are protein antigens. Further preferred are heterologous antigens or foreign antigens, i.e. antigens which are not endogenous to the respective microorganism of the invention or antigens which are not expressed by the respective microorganism of the invention by nature, but are introduced into it by means of standard molecular biotechnological methods.

The term "complete antigen" in the course of the present invention refers to complete molecules that react with antibodies according to the definition above. Examples of complete antigens are for instance full-length proteins, which are also preferred.

The term "partial antigen" in the course of the present invention refers to specific parts of molecules that react with antibodies according to the definition above. Partial antigens can be for instance protein motives such as amino acid loops within proteins, protein kinase domains, epitopes and the like. Preferred are protein kinase domains and epitopes, the latter of which are specific sites of an antigen recognized by an antibody (also referred to as antigenic determinants). The term "antigenic determinant" is also intended to embrace so-called T cell epitopes, including short peptide sequences that bind to and are presented to the cellular immune system via MHC Class I and Class II molecules.

The terms "wild-type" and "mutated" in connection with "protein" in the course of the present invention refer to proteins consisting of either their "natural" dominating amino acid sequence (encoded by the respective nucleotide sequence) and proteins that have one or more mutations in their amino acid sequence (encoded by the respective nucleotide sequence) compared to the wild-type sequence, respectively. Preferably wild-type and/or mutated proteins are derived from tumor cells. As for partial antigens it is further preferred that the sequence encompasses mutations, i.e. an epitope is chosen that preferably contains one or more mutations, for instance the B-Raf V600E epitope.

Microorganisms in the meaning of the invention are bacteria, gram-positive bacteria, gram-negative bacteria and eukaryotic cells, the latter of which comprise unicellular parasites, yeasts, tumor cells and cell line cells, such as *Sacharomyces cerevisiae, Leishmania* spp., autologous patient derived tumor cells and tumor cell lines. Such microorganisms are usually used as carriers for the transfer of nucleotide sequences being foreign (heterologous or heterogeneous) for the microorganism. Preferably, bacteria are used, which are attenuated in their virulence, for instance bacteria that carry a deleted or inactivated aroA, aro, asd, gal, pur, cya, crp, phoP/Q, omp gene or are temperature-sensitive mutants or antibiotic-dependent mutants (Cardenas and Clements, 1992). Further preferred as a microorganism comprising above components (I) to (IV) is a gram-negative, attenuated, facultative intracellular bacterium as a carrier, which is able to overcome the intestinal mucosa (e.g. *Salmonella* spp. or *Shigella* spp.).

In a preferred embodiment, a microorganism comprising above components (I) to (IV) is provided, wherein the microorganism is selected from the group consisting of "bacterium, gram-positive bacterium, gram-negative bacterium, eukaryotic cell" and preferably is selected from the group consisting of "*Escherichia* spp., *Escherichia coli, Salmonella* spp., *Salmonella typhi, Salmonella typhimurium, Yersinia* spp., *Yersinia enterocolitica, Vibrio* spp., *Vibrio cholerae, Listeria* spp., *Listeria monocytogenes, Shigella* spp., *Shigella flexneri*", wherein preferably the virulence of the microorganism is attenuated. Further preferred, *Vibrio cholerae* is excluded from above defined microganisms.

The term "spp." in connection with any microorganism is intended to comprise for the purpose of the present invention all members of a given genus, including species, subspecies and others. The term "*Salmonella* spp." for instance is intended to comprise all members of the genus *Salmonella*, such as *Salmonella typhi* and *Salmonella typhimurium*.

In another preferred embodiment, a microorganism according to above definitions is provided, wherein the at least one complete or partial antigen of at least one wild-type or mutated protein according to component (I) is selected from the group consisting of the following wild-type proteins and their known mutants: "receptor; extracellular, transmembranic or intracellular part of a receptor; adhesion molecule; extracellular, transmembranic or intracellular part of an adhesion molecule; signal-transducing protein; cell-cycle protein; transcription factor; differentiation protein; embryonic protein; viral protein; allergen; protein of microbial pathogen; protein of eukaryotic pathogen; cancer testis antigen protein; tumor antigen protein; and/or tissue-cell specific protein", wherein the tissue cell is selected from the group consisting of "glandula thyroidea, glandula mammaria, glandula salivaria, nodus lymphoideus, glandula mammaria, tunica mucosa gastris, kidney, ovarium, prostate, cervix, tunica serosa vesicae urinariae and nevus".

As for the mutated protein, the mutation may have been oncogenic and may have caused a loss or a gain of its original cellular functions.

Such antigens perform in the cell the control of the cell growth and of the cell division and are presented on the cell membrane of normal cells, for instance by the MHC class I molecule. In tumor cells, these antigens are frequently overexpressed or specifically mutated. Such mutations can have function limitations of oncogene suppressors or the activation of proto-oncogenes to oncogenes as a consequence and can be involved alone or commonly with over-expressions in the tumor growth. Such cell antigens are presented on the membrane of tumor cells and thus represent antigens on tumor cells, without however causing an immune reaction affecting the tumor disease of the patient. Rapp (U.S. Pat. No. 5,156, 841) has already described the use of oncoproteins, i.e. expression products of the oncogenes, as an immunogen for tumor vaccines.

Examples for antigens and their (oncogenic) mutations according to the invention are i) receptors, such as Her-2/neu, androgen receptor, estrogen receptor, lactoferrin receptor, midkine receptor, EGF receptor, ERBB2, ERBB4, TRAIL receptor, FAS, TNFalpha receptor, TGF-beta receptor; ii) signal-transducing proteins, such as c-Raf (Raf-1), A-Raf, B-Raf, B-Raf V599E, B-Raf V600E, B-Ra , B-Raf V600E kinase domain, B-Raf V600E KD, B-Raf V600E kinase domain , B-Raf kinase domain, B-Raf kinase domain KD, Ras, Bcl-2, Bcl-X, Bcl-W, Bfl-1, Brag-1, Mcl-1, A1, Bax, BAD, Bak, Bcl-Xs, Bid, Bik, Hrk, Bcr/abl, Myb, C-Met, IAP1, IAO2, XIAP, ML-IAP LIVIN, survivin, APAF-1; iii) proteins of the cell cycle control, such as cyclin D(1-3), cyclin E, cyclin A, cyclin B, cyclin H, Cdk-1, Cdk-2, Cdk-4, Cdk-6, Cdk-7, Cdc25C, p16, p15, p21, p27, p18, pRb, p107, p130, E2F(1-5), GAAD45, MDM2, PCNA, ARF, PTEN, APC, BRCA, p53 and homologues; iv) transcription factors, such as C-Myc, NFkB, c-Jun, ATF-2, Spl; v) embryonic proteins, such as carcinoembryonic antigen, alpha-fetoprotein, MAGE, MAGE-1, MAGE-3, NY-ESO-1, PSCA; vi) differentiation antigens, such as MART, Gp100, tyrosinase, GRP, TCF-4, basic myelin, alpha-lactalbumin, GFAP, prostate specific antigen (PSA), fibrillary acid protein, tyrosinase, EGR-1, MUC1; vii) viral antigens, such as of the following viruses: HIV, HPV, HCV, HPV, EBV, CMV, HSV, influenza virus, influenza virus type A, influenza virus type A (H5N1) and (H3N2), influenza virus type B, influenza virus type C; hemagglutinins, hemagglutinin H1, hemagglutinin H5, hemagglutinin H7, hemagglutinin HA1 (preferably from Influenza A virus (A/Thailand/1 (KAN-1) 2004 (H5N1), hemagglutinin HA12 (preferably from Influenza A virus (A/Thailand/1 (KAN-1) 2004 (H5N1), hemagglutinin HA12C (preferably from Influenza A virus (A/Thailand/1 (KAN-1) 2004 (H5N1), neuramidase, microbial antigens: p60, LLO, urease etc. Antigens of eukaryotic pathogens: CSP (malaria), calflagin (*trypanosoma*), CPB (*Leishmania major*) etc.

In yet another preferred embodiment, a microorganism according to above definitions is provided, wherein the at least one complete or partial antigen of at least one wild-type or mutated protein according to component (I) is selected from the group consisting of the following wild-type proteins and their known mutants: "Her-2/neu, androgen receptor, estrogen receptor, midkine receptor, EGF receptor, ERBB2, ERBB4, TRAIL receptor, FAS, TNFalpha receptor, TGF-beta receptor, lactoferrin receptor, basic myelin, alpha-lactalbumin, GFAP, fibrillary acid protein, tyrosinase, EGR-1, MUC1, c-Raf (Raf-1), A-Raf, B-Raf, B-Raf V599E, B-Raf V600E, B-Raf , B-Raf V600E kinase domain, B-Raf V600E KD, B-Raf V600E kinase domain KD, B-Raf kinase domain, B-Raf kinase domain , N-Ras, K-Ras, H-Ras, Bcl-2, Bcl-X, Bcl-W, Bfl-1, Mcl-1, A1, Bax, BAD, Bak, Bcl-Xs, Bid, Bik, Hrk, Bcr/abl, Myb, C-Met, IAP1, IAO2, XIAP, ML-IAP LIVIN, survivin, APAF-1, cyclin D(1-3), cyclin E, cyclin A, cyclin B, cyclin H, Cdk-1, Cdk-2, Cdk-4, Cdk-6, Cdk-7, Cdc25C, p16, p15, p21, p27, p18, pRb, p107, p130, E2F(1-5), GAAD45, MDM2, PCNA, ARF, PTEN, APC, BRCA, Akt, PI3K, mTOR, p53 and homologues, C-Myc, NFkB, c-Jun, ATF-2, Sp1, prostate specific antigen (PSA), carcinoembryonic antigen, alpha-fetoprotein, PAP; PSMA; STEAP; MAGE, MAGE-1, MAGE-3, NY-ESO-1, PSCA, MART, Gp100, tyrosinase, GRP, TCF-4, viral antigens of the viruses HIV, HPV, HCV, HPV, EBV, CMV, HSV, influenza virus, influenza virus type A, influenza virus type A (H5N1) and (H3N2), influenza virus type B, influenza virus type C; hemagglutinins, hemagglutinin H1, hemagglutinin H5, hemagglutinin H7, hemagglutinin HA1 (preferably from Influenza A virus (A/Thailand/1 (KAN-1) 2004 (H5N1), hemagglutinin HA 12 (preferably from Influenza A virus (A/Thailand/1 (KAN-1) 2004 (H5N1), hemagglutinin HA12C (preferably from Influenza A virus (A/Thailand/1 (KAN-1) 2004 (H5N1), neuramidase, p60, LLO, urease, CSP, calflagin and/or CPB".

In yet another preferred embodiment, a microorganism according to above definitions is provided, wherein the at least one complete or partial antigen of at least one wild-type or mutated protein according to component (I) is selected from the group of kinases consisting of the following wild-type proteins and their known mutants (accession numbers in parentheses): AAK1 (NM 014911), AATK (NM 004920), ABL1 (NM 005157), ABL2 (NM 005158), ACK1 (NM 005781), ACVR1 (NM 001105), ACVR1B (NM 020328), ACVR2 (NM 001616), ACVR2B (NM 001106), ACVRL1 (NM 000020), ADCK1 (NM 020421), ADCK2 (NM 052853), ADCK4 (NM 024876), ADCK5 (NM 174922), ADRBK1 (NM 001619), ADRBK2 (NM 005160), AKT1 (NM 005163), AKT2 (NM 001626), AKT3 (NM 005465), ALK (NM 004304), ALK7 (NM 145259), ALS2CR2 (NM 018571), ALS2CR7 (NM 139158), AMHR2 (NM 020547), ANKK1 (NM 178510), ANKRD3 (NM 020639), APEG1 (NM 005876), ARAF (NM 001654), ARK5 (NM 014840), ATM (NM 000051), ATR (NM 001184), AURKA (NM 003600), AURKB (NM 004217), AURKC (NM 003160), AXL (NM 001699), BCKDK (NM 005881), BCR (NM 004327), BIKE (NM 017593), BLK (NM 001715), BMPR1A (NM 004329), BMPR1B (NM 001203), BMPR2 (NM 001204), BMX (NM 001721), BRAF (NM 004333), BRD2 (NM 005104), BRD3 (NM 007371), BRD4 (NM 014299), BRDT (NM 001726), BRSK1 (NM 032430), BRSK2 (NM 003957), BTK (NM 000061), BUB1 (NM 004336), BUB1B (NM 001211), CABC1 (NM 020247), CAMK1 (NM 003656), CAMK1B (NM 198452), CAMK1D (NM 020397), CAMK1G (NM 020439), CAMK2A (NM 015981), CAMK2B (NM 001220), CAMK2D (NM 001221), CAMK2G (NM 001222), CAMK4 (NM 001744), CAMKK1 (NM 032294), CAMKK2 (NM 006549), CASK (NM 003688), CCRK (NM 012119), CDC2 (NM 001786), CDC2L1 (NM 001787), CDC2L5 (NM 003718), CDC42BPA (NM 014826), CDC42BPB (NM 006035), CDC7L1 (NM 003503), CDK10 (NM 003674), CDK11 (NM 015076), CDK2 (NM 001798), CDK3 (NM 001258), CDK4 (NM 000075), CDK5 (NM 004935), CDK6 (NM 001259), CDK7 (NM 001799), CDK8 (NM 001260), CDK9 (NM 001261), CDKL1 (NM 004196), CDKL2 (NM 003948), CDKL3 (NM 016508), CDKL4 (NM 001009565), CDKL5 (NM 003159), CHEK1 (NM 001274), CHUK (NM 001278), CIT (NM 007174), CLK1 (NM 004071), CLK2 (NM 003993), CLK3 (NM 003992), CLK4 (NM 020666), CRK7 (NM 016507), CSF1R (NM 005211), CSK (NM 004383), CSNK1A1 (NM 001892), CSNK1D (NM 001893), CSNK1E (NM 001894), CSNK1G1 (NM 022048), CSNKIG2 (NM 001319), CSNK1G3 (NM 004384), CSNK2A1 (NM 001895), CSNK2A2 (NM 001896), DAPK1 (NM 004938), DAPK2 (NM 014326), DAPK3 (NM 001348), DCAMKL1 (NM 004734), DCAMKL2 (NM 152619), DCAMKL3 (XM 047355), DDR1 (NM 013993), DDR2 (NM 006182), DMPK (NM 004409), DMPK2 (NM 017525.1), DYRK1A (NM 001396), DYRK1B (NM 006484), DYRK2 (NM 006482), DYRK3 (NM 003582), DYRK4 (NM 003845), EEF2K (NM 013302), EGFR (NM 005228), EIF2AK3 (NM 004836), EIF2AK4 (NM_001013703), EPHA1 (NM 005232), EPHA10 (NM 001004338), EPHA2 (NM 004431), EPHA3 (NM 005233), EPHA4 (NM 004438), EPHA5 (NM 004439), EPHA6 (XM 114973), EPHA7 (NM 004440), EPHA8 (NM 020526), EPHB1 (NM 004441), EPHB2 (NM 017449), EPHB3 (NM 004443), EPHB4 (NM 004444), EPHB6 (NM 004445), ERBB2 (NM 004448), ERBB3 (NM 001982), ERBB4 (NM 005235), ERK8 (NM 139021), ERN1 (NM 001433), ERN2 (NM 033266), FASTK (NM 025096), FER (NM 005246), FES (NM 002005), FGFR1 (NM 000604), FGFR2 (NM 022970), FGFR3 (NM 000142), FGFR4 (NM 022963), FGR (NM 005248), FLJ23074 (NM 025052), FLJ23119 (NM 024652), FLJ23356 (NM 032237), FLT1 (NM 002019), FLT3 (NM 004119), FLT4 (NM 002020), FRAP1 (NM 004958), FRK (NM 002031), FYN (NM 002037), GAK (NM 005255), GPRK5 (NM 005308), GPRK6 (NM 002082), GPRK7 (NM 139209), GRK4 (NM 005307), GSG2 (NM 031965), GSK3A (NM 019884), GSK3B (NM 002093), GUCY2C (NM 004963), GUCY2D (NM 000180), GUCY2F (NM 001522), H11 (NM 014365), HAK (NM 052947), HCK (NM 002110), HIPK1 (NM 152696), HIPK2 (NM 022740), HIPK3 (NM 005734), HIPK4 (NM 144685), HRI (NM 014413), HUNK (NM 014586), ICK (NM 016513), IGF1R (NM 000875), IKBKB (NM 001556), IKBKE (NM 014002), ILK (NM 004517), INSR (NM 000208), INSRR (NM 014215), IRAK1 (NM 001569), IRAK2 (NM 001570), IRAK3 (NM 007199), IRAK4 (NM 016123), ITK (NM 005546), JAK1 (NM 002227), JAK2 (NM 004972), JAK3 (NM 000215), KDR (NM 002253), KIS (NM 144624), KIT (NM 000222), KSR (XM 290793), KSR2 (NM 173598), LAK (NM 025144), LATS1 (NM 004690), LATS2 (NM 014572), LCK (NM 005356), LIMK1 (NM 016735), LIMK2 (NM 005569), LMR3 (XM 055866), LMTK2 (NM 014916), LOC149420 (NM 152835), LOC51086 (NM 015978), LRRK2 (XM 058513), LTK (NM 002344), LYN (NM 002350), MAK (NM 005906), MAP2K1 (NM 002755), MAP2K2 (NM 030662), MAP2K3 (NM 002756), MAP2K4 (NM 003010), MAP2K5 (NM 002757), MAP2K6 (NM 002758), MAP2K7 (NM 005043), MAP3K1 (XM 042066), MAP3K10 (NM 002446), MAP3K11 (NM 002419), MAP3K12 (NM 006301), MAP3K13 (NM 004721), MAP3K14 (NM 003954), MAP3K2 (NM 006609), MAP3K3 (NM 002401), MAP3K4 (NM 005922), MAP3K5 (NM 005923), MAP3K6 (NM 004672), MAP3K7 (NM 003188), MAP3K8 (NM 005204), MAP3K9 (NM 033141), MAP4K1 (NM 007181), MAP4K2 (NM 004579), MAP4K3 (NM 003618), MAP4K4 (NM 145686), MAP4K5 (NM 006575), MAPK1 (NM 002745), MAPK10 (NM 002753), MAPK11 (NM 002751), MAPK12 (NM 002969), MAPK13 (NM 002754), MAPK14 (NM 001315), MAPK3 (NM 002746), MAPK4 (NM 002747), MAPK6 (NM 002748), MAPK7 (NM 002749), MAPK8 (NM 002750), MAPK9 (NM 002752), MAPKAPK2 (NM 032960), MAPKAPK3 (NM 004635), MAPKAPK5 (NM 003668), MARK (NM 018650), MARK2 (NM 017490), MARK3 (NM 002376), MARK4 (NM 031417), MAST1 (NM 014975), MAST205 (NM 015112), MAST3 (XM 038150), MAST4 (XM 291141), MASTL (NM 032844), MATK (NM 139355), MELK (NM 014791), MERTK (NM 006343), MET (NM 000245), MGC33182 (NM 145203), MGC42105 (NM 153361), MGC43306 (C9orf96), MGC8407 (NM 024046), MIDORI (NM 020778), MINK (NM 015716), MKNK1 (NM 003684), MKNK2 (NM 017572), MLCK (NM 182493), MLK4 (NM 032435), MLKL (NM 152649), MOS (NM 005372), MST1R (NM 002447), MST4 (NM 016542), MUSK (NM 005592), MYLK (NM 053025), MYLK2 (NM 033118), MYO3A (NM 017433), MYO3B (NM 138995), NEK1 (NM 012224), NEK10 (NM 152534), NEK11 (NM 024800), NEK2 (NM 002497), NEK3 (NM 002498), NEK4 (NM 003157), NEK5 (MGC75495), NEK6 (NM 014397), NEK7 (NM 133494), NEK8 (NM 178170), NEK9 (NM 033116), NLK (NM 016231), NPR1 (NM 000906), NPR2 (NM 003995), NRBP (NM 013392), NRBP2 (NM 178564), NRK (NM 198465), NTRK1 (NM 002529), NTRK2 (NM 006180), NTRK3 (NM 002530), OBSCN (NM 052843), OSR1 (NM 005109), PACE-1 (NM 020423), PAK1 (NM 002576), PAK2 (NM 002577), PAK3 (NM 002578), PAK4 (NM 005884), PAK6 (NM 020168), PAK7 (NM 020341), PASK (NM 015148), PCTK1 (NM 006201), PCTK2 (NM 002595), PCTK3 (NM 212503), PDGFRA (NM 006206), PDGFRB (NM 002609), PDK1 (NM 002610), PDK2 (NM 002611), PDK3 (NM 005391), PDK4 (NM 002612), PDPK1 (NM 002613), PFTK1 (NM 012395), PHKG1 (NM 006213), PHKG2 (NM 000294), PIK3R4 (NM 014602), PIM1 (NM 002648), PIM2 (NM 006875), PIM3 (NM 001001852), PINK1 (NM 032409), PKE (NM 173575), PKMYT1 (NM 004203), pknbeta (NM 013355), PLK (NM 005030), PLK3 (NM 004073), PRKAA1 (NM 006251), PRKAA2 (NM 006252), PRKACA (NM 002730), PRKACB (NM 002731), PRKACG (NM 002732), PRKCA (NM 002737), PRKCB1 (NM 002738), PRKCD (NM 006254), PRKCE (NM 005400), PRKCG (NM 002739), PRKCH (NM 006255), PRKCI (NM 002740), PRKCL1 (NM 002741), PRKCL2 (NM 006256), PRKCM (NM 002742), PRKCN (NM 005813), PRKCQ (NM 006257), PRKCZ (NM 002744), PRKD2 (NM 016457), PRKDC (NM 006904), PRKG1 (NM 006258), PRKG2 (NM 006259), PRKR (NM 002759), PRK-WNK1 (NM 018979), PRKWNK2 (NM 006648), PRK-WNK3 (NM 020922), PRKWNK4 (NM 032387), PRKX (NM 005044), PRKY (NM 002760), PRPF4B (NM 003913), PSKH1 (NM 006742), PSKH2 (NM 033126), PTK2 (NM 005607), PTK2B (NM 004103), PTK6 (NM 005975), PTK7 (NM 002821), PTK9 (NM 002822), PTK9L (NM 007284), PXK (NM 017771), QSK (NM 025164), RAD53 (NM 007194), RAF1 (NM 002880), RAGE (NM 014226), RET (NM 020975), RHOK (NM 002929), RIOK1 (NM 031480), RIOK2 (NM 018343), RIPK1 (NM 003804), RIPK2 (NM 003821), RIPK3 (NM 006871), RIPK5 (NM 015375), RNASEL (NM 021133), ROCK1 (NM 005406), ROCK2 (NM 004850), ROR1 (NM 005012), ROR2 (NM 004560), ROS1 (NM 002944), RPS6KA1 (NM 002953), RPS6KA2 (NM 021135), RPS6KA3 (NM 004586), RPS6KA4 (NM 003942), RPS6KA5 (NM 004755), RPS6KA6 (NM 014496), RPS6KB1 (NM 003161), RPS6KB2 (NM 003952), RPS6KC1 (NM 012424), RPS6KL1 (NM 031464), RYK (NM 002958), SBK (XM 370948), SCYL1 (NM 020680), SCYL2 (NM 017988), SGK (NM 005627), SgK069 (SU SgK069), SgK085 (XM 373109), SgK110 (SU SgK110), SGK2 (NM 016276), SgK223 (XM 291277), SgK269 (XM 370878), SgK424 (CGP SgK424), SgK493 (SU SgK493), SgK494 (NM 144610), SgK495 (NM 032017), SGKL (NM 013257), SK681 (NM 001001671), SLK (NM 014720), SMG1 (NM 015092), SNARK (NM 030952), SNF1LK (NM 173354), SNF1LK2 (NM 015191), SNK (NM 006622), SNRK (NM 017719), SRC (NM 005417), SRMS (NM 080823), SRPK1 (NM 003137), SRPK2 (NM 003138), SSTK (NM 032037), STK10 (NM 005990), STK11 (NM 000455), STK16 (NM 003691), STK17A (NM 004760), STK17B (NM 004226), STK18 (NM 014264), STK19 (NM 032454), STK22B (NM 053006), STK22C (NM 052841), STK22D (NM 032028), STK23 (NM 014370), STK24 (NM 003576), STK25 (NM 006374), STK3 (NM 006281), STK31 (NM 031414), STK32B (NM 018401), STK33 (NM 030906), STK35 (NM 080836), STK36 (NM 015690), STK38 (NM 007271), STK38L (NM 015000), STK39 (NM 013233), STK4 (NM 006282), STLK5 (NM 001003787), STYK1 (NM 018423), SUDD (NM 003831), SYK (NM 003177), TAF1 (NM 138923), TAF1L (NM 153809), TAO1 (NM 004783), TAOK1 (NM 020791), TAOK3 (NM 016281), TBCK (NM 033115), TBK1 (NM 013254), TEC (NM 003215), TEK (NM 000459), TESK1 (NM 006285), TESK2 (NM 007170), TEX14 (NM 031272), TGFBR1 (NM 004612), TGFBR2 (NM 003242), TIE (NM 005424), TIF1 (NM 003852), TLK1 (NM 012290), TLK2 (NM 006852), TNIK (NM 015028), TNK1 (NM 003985), TOPK (NM 018492), TP53RK (NM 033550), TRAD (NM 007064), TRIB1 (NM 025195), TRIB2 (NM 021643), TRIB3 (NM 021158), TRIM28 (NM 005762), TRIM33 (NM 015906), TRIO (NM 007118), TRPM6 (NM 017662), TRPM7 (NM 017672), TRRAP (NM 003496), TSSK4 (NM 174944), TTBK1 (NM 032538), TTBK2 (NM 173500), TTK (NM 003318), TTN (NM 003319), TXK (NM 003328), TYK2 (NM 003331), TYRO3 (NM 006293), ULK1 (NM 003565), ULK2 (NM 014683), ULK3 (NM 015518), ULK4 (NM 017886), VRK1 (NM 003384), VRK2 (NM 006296), VRK3 (NM 016440), WEE1 (NM 003390), Wee1B (NM 173677), YANK1 (NM 145001), YESI (NM 005433), ZAK (NM 016653), and/or ZAP70 (NM 001079).

The term "allergen" in the course of the present invention refers to complete or partial antigens as defined herein that elicit hypersensitivity and/or allergic reactions. Examples are Der p 5 (mite), Bet v 1 (birch pollen), Ph1 p 1 (grass pollen), Asp f I/a (*Aspergillus*), PLA 2 (bee), Hey b (latex) (Schmid-Grendelmeier and Crameri, 2001).

Antigens of microbial and eukaryotic pathogens and of cancer testis antigens are enclosed in the list above.

In the course of the present invention, protein toxins and/or their subunits according to component (II) are preferably bacterial protein toxins, more preferably exotoxins. Examples of bacterial exotoxins are type I toxins (superantigens), type II toxins (pore-forming toxins) and (iii) type III toxins (A-B toxins).

In a preferred embodiment, a microorganism according to above definitions is provided, wherein component (II) is selected from the group consisting of "bacterial toxin, enterotoxin, exotoxin, type I toxin, type II toxin, type III toxin, type IV toxin, type V toxin, RTX toxin, AB toxin, A-B toxin, A/B toxin, A+B toxin, A-5B toxin and/or AB5 toxin.

In yet a further preferred embodiment, a microorganism according to above definitions is provided, wherein component (II) is selected from the group consisting of "Adenylate cyclase toxin, Anthrax toxin, Anthrax toxin (EF), Anthrax toxin (LF), *Botulinum* toxin, Cholera toxin (CT, Ctx), Cholera toxin subunit B (CTB, CtxB), Diphtheria toxin (DT, Dtx), *E. coli* LT toxin, *E. coli* heat labile enterotoxin (LT), *E. coli* heat labile enterotoxin subunit B (LTB), *E. coli* ST toxin, *E. coli* heat stabile enterotoxin (ST), Erythrogenic toxin, Exfoliatin toxin, Exotoxin A, *Perfringens* enterotoxin, *Pertussis* toxin (PT, Ptx), Shiga toxin (ST, Stx), Shiga toxin subunit B (STB, StxB), Shiga-like toxin, *Staphylococcus* enterotoxins, Tetanus toxin (TT), Toxic shock syndrome toxin (TSST-1), Vero toxin (VT), Toxin A (TA) and Toxin B (TB) of *Clostridium difficile*, Lethal Toxin (LT) and Hemorrhagic Toxin (HT) of *Clostridium sordellii*, alpha Toxin (AT) of *Clostridium novyi*".

However, if Cholera Toxin or its subunit CtxB is used as toxins according to component (II) of the invention, it is preferred not to employ *Vibrio cholerae* as bacterial carrier (microorganism).

In a preferred embodiment, a microorganism according to above definitions is provided, wherein component (I) and component (II) are linked together to enable the expression and/or secretion of a fusion protein encoded by both components. More preferably, this fusion protein is selected from the group consisting of "CtxB-PSA, CtxB-B-Raf V600E KD (kinase dead), CtxB-B-Raf V600E kinase domain, CtxB-B-Raf V600E kinase domain KD (kinase dead), CtxB-B-Raf, CtxB-B-Raf KD (kinase dead), CtxB B-Raf kinase domain KD (kinase dead), CtxB-HA1 (subunit 1 of a hemagglutinin of an influenza virus), CtxB-HA12C".

Secretion is the process of segregating, elaborating, and releasing chemicals from a cell, or a secreted chemical substance or amount of substance. Secretion is not unique to eukaryotes alone; it is present in bacteria and archaea as well. ATP binding cassette (ABC) type transporters are common to all the three domains of life. The Sec system is also another conserved secretion system which is homologous to the translocon in the eukaryotic endoplasmic reticulum consisting of Sec 61 translocon complex in yeast and Sec Y-E-G complex in bacteria. Gram-negative bacteria have two membranes, thus making secretion topologically more complex. So there are at least five specialized secretion system in Gram negative bacteria:

(1) Type I secretion system: It is same as the ATP binding cassette transporters mentioned above.

(2) Type II secretion system: It depends on the Sec system for a protein to cross the inner membrane and another special system to cross the outer membrane. Bacterial pili use modifications of the sec system, but are different from type I system.

(3) Type III secretion system (T3SS): It is homologous to bacterial flagellar basal body. It is like a molecular syringe through which a bacterium (e.g. *Shigella* or *Yersinia*) can inject proteins into eukaryotic cells. The low $Ca^{2+}$ concentration in the cytosol opens the gate that regulates T3SS. The Hrp system in plant pathogens injects hairpins through similar mechanisms into plants.

(4) Type IV secretion system: It is homologous to conjugation machinery of bacteria (and archaeal flagella). It is capable of transporting both DNA and proteins. It was discovered in *Agrobacterium tumefaciens*, which uses this system to introduce the Ti plasmid and proteins into the host which develops the crown gall (tumor). *Helicobactor pylori* uses a type IV secretion system to inject Cag A into gastic epithelial cells. *Bordetella pertussis*, the causative agent of whooping cough, secretes the *pertussis* toxin partly through the type IV system.

(5) Type V secretion system, also called autotransporter system: This use the sec system for crossing the inner membrane. The proteins which use this path have the capability to form a beta barrel in their C terminus and insert into the outer membrane to transport the rest of the peptide out. Finally the beta barrel may be cleaved and left back in the outer membrane. Some people believe these remnants of the autotransporters gave rise to the porins which are similar beta barrels.

Bacteria as well as mitochondria and chloroplasts also use many other special transport systems such as the twin-arginine translocation (Tat) pathway which, in contrast to Sec-dependent export, transports fully folded proteins across the membrane. The name of the system comes from the requirement for two consecutive arginines in the signal sequence required for targeting to this system. Secretion in gram-negative bacteria involves overcoming the inner and outer membrane by the way of a suitable secretion system, like e.g. the Hly type I or type III secretion system or AIDA auto-transporter. In gram-positive bacteria the secretion system has to overcome the inner membrane and the cell wall, which, in most strains, can be achieved by fusion with a suitable secretion signal.

Component (III) a) is at least one nucleotide sequence coding for at least one transport system which enables the expression of the expression products of component (I) and component (II) on the outer surface of the microorganism and/or enables the secretion of the expression products of component (I) and component (II). The respective component can as an option be either secreted or expressed on the membrane of the microorganism, i.e. is membrane-bound. Such transport systems are for instance i) type I secretion system, type II secretion system, type III secretion system, type IV secretion system, type V secretion system, ii) the hemolysin transport system (signal) of *E. coli* (nucleotide sequences containing HlyA, HlyB and HlyD under the control of the hly-specific promoter); the following transport signals are to be used: for the secretion—the C-terminal HlyA transport signal, in presence of HlyB and HlyD proteins; for the membrane-bound expression—the C-terminal HlyA transport signal, in presence of HlyB protein, iii) the hemolysin transport system (signal) of *E. coli* (nucleotide sequences containing HlyA, HlyB and HlyD under the control of a not hly-specific bacterial promoter), iv) the transport signal for the S-layer protein (Rsa A) of *Caulobacter crescentus*; the following transport signals are to be used: for the secretion and the membrane-bound expression—the C-terminal RsaA transport signal, v) the transport signal for the TolC protein *Escherichia coli*; the following transport signals are to be used: for the membrane-bound expression—the N-terminal transport signal of TolC (the integral membrane protein TolC of *E. coli* is a multi-functional pore-forming protein of the outer membrane of *E. coli*, which serves—in addition to functions such as the reception of colicin E1 (Morona et al., 1983) and the secretion of colicin V (Fath et al., 1991) also as a receptor for the U3 phage (Austin et al., 1990); this protein is not only found in *E. coli*, but also in a multitude of gram-negative bacteria (Wiener, 2000); the localization in the outer membrane and the wide occurrence make TolC to an ideal candidate to present heterologous antigens, in order e.g. to cause an immune reaction.

Gram positive bacteria do not encompass an outer membrane. Secretion in these cases is simpler and usually does not require dedicated secretion machinery for transport through the cell membrane and cell wall. In the case of gram positive bacteria, secretion signals fused N-terminally to the heterologous protein are usually necessary and sufficient for secretion. Proteins, for which these signal sequences have been described, comprise principally all secreted bacterial proteins. Examples for *listeria* are the secretion signals derived from Listeriolysin, p60 or ActA. In general, a similar approach applies to eukaryotic cells, where a signal sequence (for instance the ubiquitous secretion signal Vtgss) targeting the protein to the endoplasmatic reticulum in the absence of a retention signal is necessary and sufficient for secretion.

Optional component (III) b) is at least one nucleotide sequence coding for at least one protein for lysing the microorganism in the cytosol of mammalian cells and for intracellularly releasing plasmids or expression vectors, which are contained in the lysed microorganism. Such lytic proteins (endolysins) are for instance *Listeria*-specific lysis proteins, such as PLY551 (Loessner et al., 1995) and/or the *Listeria*-specific holin under the control of a listerial promoter. A preferred embodiment of this invention is the combination of different components (III) b), for instance the combination of a lysis protein and the holin.

Both components (III) a) and/or (III) b) may be independently from each other constitutively active.

In a preferred embodiment, a microorganism according to above definitions is provided, wherein component (III) a) is selected from the group consisting of "type I secretion system, type II secretion system, type III secretion system, type IV secretion system, type V secretion system, hemolysin transport system (signal) of *Escherichia coli* (nucleotide sequences containing HlyA, HlyB and HlyD under the control of the hly-specific promoter), hemolysin transport system (signal) of *Escherichia coli* (nucleotide sequences containing HlyA, HlyB and HlyD under the control of a not hly-specific bacterial promoter), transport signal for the S-layer (Rsa A) protein of *Caulobacter crescentus*, transport signal for the TolC protein of *Escherichia coli*, secretion signal Vtgss and/or secretion signals derived from listeriolysin, p60 and/or ActA" and wherein component (III) b) is selected from the group consisting of "endolysins, lytic protein of gram-positive bacteria, lytic protein of *Listeria monocytogenes*, PLY551 of *Listeria monocytogenes* and/or holin of *Listeria monocytogenes*".

In a further preferred embodiment, the same component (III) a) enables the expression of the expression products of component (I) and component (II) on the outer surface of the microorganism and/or enables the secretion of the expression products of component (I) and component (II). That is in this preferred embodiment component (III) a) is at least one nucleotide sequence coding for only one transport system, which enables the concomitant expression of the expression products of component (I) and component (II) on the outer surface of the microorganism and/or enables the concomitant secretion of the expression products of component (I) and component (II), wherein such preferred component (III) a) is at least one nucleotide sequence coding for the hemolysin transport system (signal) of *Escherichia coli* (nucleotide sequences containing HlyA, HlyB and HlyD under the control of the hly-specific promoter) or the hemolysin transport system (signal) of *Escherichia coli* (nucleotide sequences containing HlyA, HlyB and HlyD under the control of a not hly-specific bacterial promoter).

In yet another preferred embodiment, a microorganism according to above definitions is provided, wherein according to component (III) a) the expression products of components (I) and component (II) are secreted. More preferably, component (I) and component (II) are linked together, expressed together and secreted as a fusion protein encoded by both components. Most preferably, this fusion protein is selected from the group consisting of "CtxB-PSA, CtxB-B-Raf V600E KD (kinase dead), CtxB-B-Raf V600E kinase domain, CtxB-B-Raf V600E kinase domain (kinase dead), CtxB-B-Raf, CtxB-B-Raf KD (kinase dead), CtxB B-Raf kinase domain KD (kinase dead), CtxB-HA1 (subunit 1 of a hemagglutinin of an influenza virus), CtxB-HA12C".

In the course of the present invention, the term "secretion" refers to the secretion of a protein antigen, protein toxin and/or toxin-antigen fusion protein through both membranes of a gam-negative bacterium or through the inner membrane and cell-wall of a gram-positive bacterium into the neighboring environment, by the means of a proper secretion system, such as the ones illustrated above.

As it is known that using a secretion system, such as the hemolysin type I secretion system from *E. coli*, secretion product is usually found in all cellular fractions: cyto-plasmatically, membrane-associated, located in auto-membrane vesicles and fully secreted into the neighboring environment (Balsalobre et al., 2006), secretion in the course of the present invention does not need to be complete. However, a complete or an almost complete secretion, i.e. a majority quantity of fully secreted secretion product, is desired and preferred.

Component (IV) represents at least one nucleotide sequence for at least one activation sequence for the expression of one or more of components (I) to (III), wherein said activation sequence can be activated in the microorganism and/or is tissue cell-specific, tumor cell-specific, macrophage-specific, dendrite-specific, lymphocyte-specific, function-specific or non-cell-specific.

If the expression is membrane-bound on the outer surface of the microorganism, the activation sequence has preferably to be selected such that it is capable of being activated in the microorganism. Such activation sequences are for instance: i) constitutively active promoter regions, such as the promoter region with "ribosomal binding site" (RBS) of the beta-lactamase gene of *E. coli* or of the tetA gene (Busby and Ebright, 1994), endogenous promoter of the *E. coli* hly locus; ii) promoters, which are capable of being induced, preferably promoters, which become active after reception in the cell. To these belong the actA promoter of *L. monocytogenes* (Dietrich et al., 1998) or the pagC promoter of *S. typhimurium* (Bumann, 2001).

If the plasmids are released from the microorganism after its lysis into the cytosol of the mammalian cell, the activation sequence is not cell-specific, but tissue cell-specific, cell cycle-specific or function-specific. Preferably, such activation sequences are selected, which are particularly activated in macrophages, dendritic cells and lymphocytes.

In a further preferred embodiment, a microorganism according to above definitions is provided, wherein component (I) is selected from the group consisting of B-Raf V600E, B-Raf V600E kinase domain, B-Raf V600E KD (kinase dead), B-Raf V600E kinase domain KD (kinase dead), B-Raf KD (kinase dead), B-Raf kinase domain, B-Raf kinase domain KD (kinase dead), prostate specific antigen (PSA), hemagglutinin HA1 (preferably from Influenza A virus (A/Thailand/1 (KAN-1) 2004 (H5N1), hemagglutinin HAl2 (preferably from Influenza A virus (A/Thailand/1 (KAN-1) 2004 (H5N1), hemagglutinin HA12C (preferably from Influenza A virus (A/Thailand/1 (KAN-1) 2004 (H5N1)";

component (II) is selected from the group consisting of "Cholera toxin subunit B (CTB, CtxB), *E. coli* heat-labile enterotoxin subunit B (LTB), tetanus toxin (TT)";

component (III) a) is selected from the group consisting of "HlyA hemolysin transport signal of *Escherichia coli* together with components of the Hly secretion system (nucleotide sequences containing HlyA, HlyB and HlyD under the control of the hly-specific promoter)";

component (IV) is selected from the group consisting of "endogenous promoter of the *E. coli* hly locus";

wherein component (I) and component (II) are linked together to enable the expression of a fusion protein encoded by both components and wherein the fusion protein is secreted.

The above illustrated microorganisms according to components (I) to (IV) as well as the preferred embodiments are hereinafter referred to as microorganisms of the invention.

The microorganisms of the invention are advantageously suited for use in tumor therapy, as live vaccines in the course of tumor-targeting. That is by means of microorganisms of the invention, which function as carriers of genetic information, heterologous antigens together with protein toxins are transported to the tumor site, expressed as fusion proteins and secreted in situ.

The microorganisms of the invention are surprisingly and advantageously characterized through an efficient and superior expression and secretion of the transported, encoded and expressed toxin-antigen fusion proteins, i.e. no cytoplasmatic and/or periplasmatic aggregates occur.

Moreover, by administration of the microorganisms of the invention a strong systemic cellular immune system response is surprisingly elicited compared to orally administered protein vaccines which in contrast induce a systemic tolerance of the immune system.

Most notably, beside the induction of a systemic cellular immune system response of Th1 type, the microorganisms of the invention induce the activation of MHC class I restricted $CD8^+$ cytotoxic T-cells (CTL) and strongly enhance this CTL immune response.

Further, in addition to the induction and/or enhancement of strong cellular systemic Th1 and CTL immune system responses, the innate immune system, e.g. NK cells, NKT cells and/or gamma-delta T-cells, is also surprisingly activated by the microorganisms of the invention in a synergistic manner.

If Cholera Toxin is used as toxin component, the microorganisms of the invention possess the advantage that in humans no preexisting immunity against the toxin normally exists (in contrast to tetanus toxin for instance due to antitetanus vaccinations during childhood). Use of Cholera-Toxin and/or its subunits, in particular CtxB, is therefore preferred.

The microorganisms of the invention are particularly suitable for oral administration in live-vaccine based targeted tumor (immune) therapy. Thereby an improved patient compliance can be accomplished.

However, the microorganisms of the invention are not limited to the use in tumor therapy only. Principally, the microorganisms of the invention are also suitable for the treatment and/or prophylaxis of all these diseases that require a therapy in which induction of a systemic cellular Th1 immune system response is mandatory. Examples of such infectious diseases include, but are not limited to, HIV, influenza, HCV and other viral diseases, *Mycobacterium tuberculosis, Listeria monocytogenes* and other bacterial diseases. Symptomatic subjects, asymptomatic subjects, as well as subjects exposed to a pathogen or otherwise at risk of developing a disease or disorder, may be treated by inducing a systemic cellular Th1 immune system response.

The microorganisms of the invention are perfectly suited for the treatment of diseases like influenza, which require an optimum protection by the combination of mucosal immune system response and systemic cellular immune response. In addition, they might be useful for specific induction of Th1 like immunity in allergic diseases, e.g. allergic rhinitis. In such a case, the antigen would be an allergen that is fused to the protein toxin component and the principle of action of the respective vaccine would be the shift of the immune response from a Th2 dominated immune response against the allergen in allergic reactions (diseases) towards a Th1 immune response.

A preferred mode of application is oral application. In a preferred embodiment, a *Salmonella* strain according to this invention is fermented in appropriate medium, harvested and washed by centrifugation and subsequently formulated and stabilized using appropriate substances and lyophylized. The lyophylized substance is filled into stomach resistant capsules containing life cell numbers preferably between $10^9$ to $10^{10}$ bacteria. The capsules are orally uptaken with liquid.

Alternatively, lyophylized bacteria as described above are distributed together with sachets containing buffer which is able to neutralize the stomach acid (pharmaceutical kit). In a preferred embodiment, this buffer is a carbonate buffer. Immediately prior to use, the buffer is prepared with water and taken up, immediately afterwards the lyophylized bacteria are uptaken mixed with water.

Yet another alternative is the use of frozen bacteria. In this case, after washing bacteria are stabilized via a stabilizer, preferably succhrose or glycerine, and subsequently frozen and stored at −80° C. preferably in concentrations between $10^9$ to $10^{10}$ bacteria per dose. This preparation is preferably used in a pharmaceutical kit as described above in conjunction with carbonate buffer.

In a preferred embodiment, a pharmaceutical composition is provided comprising at least one microorganism of the invention, preferably at least one lyophilized microorganism of the invention, and a pharmaceutically acceptable carrier, preferably capsules.

The components (I) to (IV) according to the present invention are introduced into the microorganisms of the invention by methods well known to the man skilled in the art. If the microorganisms represent bacteria, the components are inserted into plasmids or expression vectors, and the plasmids or expression vectors are transferred into the bacteria. The molecular biologic cloning and transformation techniques suitable for the manufacturing of the plasmids, expression vectors and microorganisms of the invention are well-known to the person skilled in the art and represent routine experimental work.

Another subject matter of the invention is the administration of a medicament preparation containing the microorganisms of the invention. The administration is made locally or systemically, for instance orally, perorally, rectally, into the epidermis, into the subcutis, into the musculature, into a body cavity, into an organ, into the tumor or into the blood circulation.

Such medicament preparations are for instance suspensions of the microorganisms of the invention in solutions familiar to the pharmacist, suitable for injection.

A particular subject matter of this invention is the peroral or rectal administration of a medicament according to the invention for the treatment and/or prophylaxis of diseases. The administration can be made once or several times. In each administration, approximately 10 to $10^{11}$ microorganisms of the invention are administered. If the administration of this number of microorganisms of the invention does not cause a sufficient immune reaction, the number to be injected has to be increased.

After administration of the microorganisms of the invention, the tolerance for a cell presenting component (I), for instance a tumor cell, or a tissue cell, from which the tumor originates, is broken, and a strong systemic immune response directed against the tumor and/or its tissue cells is triggered. Depending on the selection of component (I), this cellular immune reaction is directed either exclusively against the tumor or also against tumor cells including the tissue cells, from which the tumor cells originate.

In another aspect, the object of the present invention has been solved by providing a medicament comprising at least one microorganism of the invention comprising above illustrated genetic components (I) to (IV) or at least one pharmaceutical composition as defined herein.

In a preferred embodiment, the microorganisms of the invention can be used for the production of a medicament for the treatment and/or prophylaxis of physiological and/or pathophysiological conditions selected from the group consisting of "uncontrolled cell division, malignant tumors, benign tumors, solid tumors, sarcomas, carcinomas, hyperproliferative disorders, carcinoids, Ewing sarcomas, Kaposi sarcomas, brain tumors, tumors originating from the brain and/or the nervous system and/or the meninges, gliomas, neuroblastomas, stomach cancer, kidney cancer, kidney cell carcinomas, prostate cancer, prostate carcinomas, connective tissue tumors, soft tissue sarcomas, pancreas tumors, liver tumors, head tumors, neck tumors, oesophageal cancer, thyroid cancer, osteosarcomas, retinoblastomas, thymoma, testicular cancer, lung cancer, bronchial carcinomas, breast cancer, mamma carcinomas, intestinal cancer, colorectal tumors, colon carcinomas, rectum carcinomas, gynecological tumors, ovary tumors/ovarian tumors, uterine cancer, cervical cancer, cervix carcinomas, cancer of body of uterus, corpus carcinomas, endometrial carcinomas, urinary bladder cancer, bladder cancer, skin cancer, basaliomas, spinaliomas, melanomas, intraocular melanomas, leukemia, chronic leukemia, acute leukemia, lymphomas, infection, viral or bacterial infection, influenza, chronic inflammation, organ rejection and/or autoimmune diseases".

Bacterial infections comprise, but are not limited to, anthrax, bacterial meningitis, botulism, brucellosis, campylobacteriosis, cat scratch disease, cholera, diphtheria, epidemic typhus, impetigo, legionellosis, leprosy (Hansen's disease), leptospirosis, listeriosis, lyme disease, melioidosis, MRSA infection, nocardiosis, *pertussis* (whooping cough), plague, pneumococcal pneumonia, psittacosis, Q fever, Rocky Mountain Spotted Fever (RMSF), salmonellosis, scarlet fever, shigellosis, syphilis, tetanus, trachoma, tuberculosis, tularemia, typhoid fever, typhus, urinary tract infections, bacterially caused heart diseases.

Viral infections comprise, but are not limited to, AIDS, AIDS related complex (ARC), chickenpox (varicella), common cold, cytomegalovirus infection, Colorado tick fever, Dengue fever, Ebola haemorrhagic fever, hand, foot and mouth disease, hepatitis, Herpes simplex, Herpes zoster, HPV, influenza (flu), Lassa fever, measles, Marburg haemorrhagic fever, infectious mononucleosis, mumps, poliomyelitis, progressive multifocal leukencephalopathy, rabies, rubella, SARS, smallpox (variola), viral encephalitis, viral gastroenteritis, viral meningitis, viral pneumonia, West Nile disease, Yellow fever.

Chronic inflammations or chronic inflammatory diseases comprise, but are not limited to, chronic cholecystitis, bronchiectasis, rheumatoid arthritis, Hashimoto's thyroiditis, inflammatory bowel disease (ulcerative colitis and Crohn's disease), silicosis and other pneumoconiosis.

Autoimmune diseases comprise, but are not limited to, systemic syndromes, such as SLE, Sjögren's syndrome, scleroderma, rheumatoid arthritis and polymyositis as well as local syndromes, such as IDDM, Hashimoto's thyroiditis, Addison's disease, pemphigus vulgaris, psoriasis, atopic dermatitis, atopic syndrome, asthma, autoimmune haemolytic anaemia, multiple sclerosis.

Corresponding medicaments comprising at least one microorganism as defined herein or at least one pharmaceutical composition as defined herein according to all herein described embodiments for use in the treatment and/or prophylaxis of physiological and/or pathophysiological conditions as described and defined herein are also comprised by the present invention.

In another aspect, the object of the present invention has been solved by providing plasmid or expression vector comprising components (I) to (IV) as illustrated herein. Preferred are microorganism of the invention that carry at least one plasmid or expression vector comprising components (I) to (IV) as illustrated herein.

In another aspect, the object of the present invention has been solved by providing a process for the production of a microorganism of the invention, wherein a plasmid or expression vector as illustrated herein is produced, and a microorganism is transformed with this plasmid or expression vector.

In another aspect, the object of the present invention has been solved by providing a pharmaceutical kit comprising at least one microorganism of the invention or a pharmaceutical composition as described above or a medicament as described above and a pharmacologically acceptable buffer, preferably a carbonate buffer.

BRIEF DESCRIPTION OF THE DRAWINGS

FIG. 1 depicts the nucleotide sequence (5'3') of *E. coli* hemolysin A (hlyA) secretion signal. The NsiI site is underlined.

FIG. 2 depicts the nucleotide sequence (5'→3') of *E. coli* hemolysin B (hlyB) of the *E. coli* hemolysin type I transport system.

FIG. 3 depicts the nucleotide sequence (5'→3') of *E. coli* hemolysin D (hlyD) of the *E. coli* hemolysin type I transport system.

FIG. 4 depicts the nucleotide sequence (5'→3') of human prostate specific antigen (PSA) without signal peptide, accession number M26663 (*Homo sapiens* prostate-specific antigen mRNA, complete cds), region 100-807 (corresponding peptide: AA 26-261).

FIG. 5 depicts the nucleotide sequence (5'→3') of Cholera Toxin subunit B (CtxB) without signal peptide encompassing region 204-494, accession number K01170 (*Vibrio cholerae* toxA and toxB genes for cholera enterotoxin subunits A2 (gamma).

FIG. 6 depicts the nucleotide sequence (5'→3') of B-Raf kinase domain (B-Raf KD) of human B-raf protein (BRAF), accession number M95712 (*Homo sapiens* B-raf protein (BRAF) mRNA, complete cds), region 1403-2359 without region 1448-1477 (corresponding peptide: AA 448-766 without AA 463-472) containing the V600E-mutation.

FIG. 7 depicts the nucleotide sequence (5'→3') of the human HLA B27 restricted B-Raf V600E epitope.

FIG. 8 depicts the nucleotide sequence (5'→3') of the genetic fusion construct of CtxB-PSA-HlyA.

FIG. 9 depicts the nucleotide sequence (5'→3') of the genetic fusion construct of Ctx-B-Raf V600E-HlyA.

FIG. 10 depicts the nucleotide sequence (5'→3') of the genetic fusion construct of CtxB-B-Raf V600E kinase domain KD-HlyA

FIG. 16 depicts the nucleotide sequence encoding for the CtxB-HA12c-HlyA fusion protein.

Figure 11:
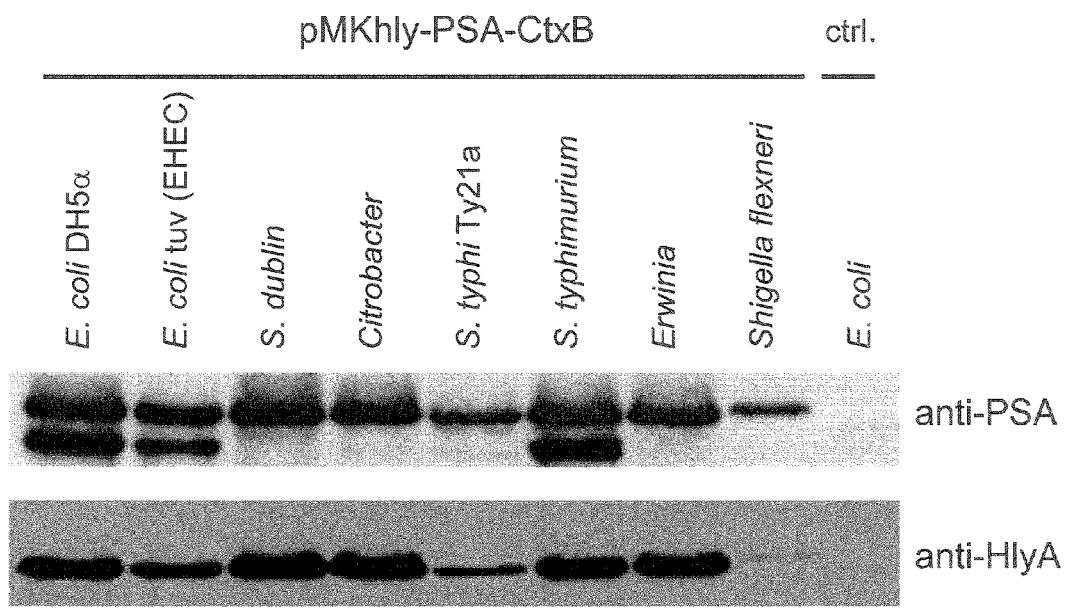
FIG. 11 depicts the functional expression and secretion of PSA-CtxB fusion proteins in different bacterial species recombinant for pMKhly-PSA-CtxB

A) lanes A1-A3: Analysis of supernatant according to TP StMoBKDC using anti-B-Raf antibody for detection. Lane A1: *S. typhi* Ty21a pMoBKDC, A2: *S. typhi* Ty21a, A3: *S. typhimurium* aroA. The BRaf-V600E L Y-CtxB fusion protein is marked with the upper arrow and has the expected size of approx. 48 kDa. Protein Marker: Invitrogen BenchMark Pre-Stained protein ladder, #10748-010

B) equivalent analysis as in A, using the newly produced anti-HlyA antibody as detection antibody. Lane 1, 2: StMoPC constructs, lane 3: *S. typhi* Ty21a MoB C; lane 4: *E. coli* MoBKDC, lane 5: *S. typhi* Ty21a, lane 6: *S. typhimurium* aroA. Protein Marker: Invitrogen BenchMark Pre-Stained protein ladder, #10748-010, Lot. 1315592

FIG. 18 depicts the full nucleotide sequence (5'→3') of the empty vector pMKhly1.

The contents of all cited references and patents are hereby incorporated by reference in their entirety. The invention is explained in more detail by means of the following examples without, however, being restricted thereto.

DETAILED DESCRIPTION OF THE INVENTION

EXAMPLES

Example 1

Construction, Expression and Secretion of PSA-CtxB Fusion Proteins in Different Bacterial Carrier Strains To prove the feasibility and demonstrate the efficacy of the *E. coli* type I hemolysin secretion system to secrete fusion proteins of tumor antigens, here prostate specific antigen (PSA), and protein toxin components, here CtxB, as adjuvant, a PSA-CtxB fusion protein was constructed as described herein. Expression and secretion was tested in different gram-negative bacterial strains, which are potentially useful as live vaccine strains in tumor therapy. The molecular biologic cloning is based on the plasmid/expression vector pMOhly1, which has been previously described (Gentschev et al., 2005; Gentschev et al., 1996, WO 03/072789).

1A Construction of Kanamycin-Resistant pMOhly1—Expression Vector Derivative

The replacement of the ampicillin resistance cassette of pMOhly1 was performed as described in (Datsenko and Wanner, 2000).

In brief, a sense primer P1 (5'-GAGTATTCAACATTTCCGTGTCGCCCTTATTCCC TTTTTTGGTGTAGGCTGGAGCTGCTTC-3') (SEQ ID NO: 1) and an anti-sense primer P2 (5'-GCGATCTGTCTATTTCGTTCATCCATAGTTGCCTGA CTCCCCATAT-GAATATCCTCCTTA-3') (SEQ ID NO: 2) and plasmid pKD4 as template were used for PCR to produce a fragment carrying the kanamycin resistance gene (Kan$^R$) flanked by regions homologous to the ampicillin resistance gene (underlined).

E. coli strain BW25114, harboring the pKD46 plasmid and the target plasmid pMOhly1 was grown at 37° C. in LB medium (Difco) supplemented with 0.2% L-(+)-arabinose for 3-4 hours before transformation of the PCR fragment.

After transformation the bacterial cells were spread on LB agar plates containing 25 µg/mL kanamycin and incubated at 37° C. overnight.

The next day, Kan$^R$ clones were picked and incubated for additional 48 h in LB medium containing 50 µg/mL kanamycin to get rid of all ampicillin resistance conferring plasmids.

Finally, clones were selected with a Kan$^R$ and ampicillin-sensitive phenotype. The replacement of the Ap$^R$ gene by the Kan$^R$ cassette was confirmed by PCR and sequencing. The resulting plasmid was called pMKhly1.

1B Cloning of pMKhly-PSA Plasmid

Sense primer PSA-Nsi1 (5'-GATTGGTG ATGCATCCCTCAT-3' (SEQ ID NO: 3); NsiI restriction sites are underlined) and anti-sense primer PSA-Nsi2 (5'-GGT-GCTCATGCATTGGCCACG-3') (SEQ ID NO: 4) were used to amplify a DNA fragment encoding PSA by PCR. PCRs were performed in a Thermal Cycler 60 (Biometra, Gottingen, Germany) for 30 cycles at 94° C. for 1 min, 54° C. for 1 min, and 72° C. for 2 min.

After digestion with the NsiI restriction enzyme, the DNA fragment, carrying the psa gene, was inserted into the single NsiI site of the export vector pMKhly1. The resulting plasmid pMKhly-PSA was isolated from E. coli DH5alpha (Invitrogene, Germany), analyzed by restriction analysis and sequenced.

1C Cloning of pMKhly-PSA/CtxB Plasmid

Sense primer Ptac-SalI (5'-AAAAAA GTCGACGGCTGTGCAGGTCGTAAATCACTGC-3') (SEQ ID NO: 5) and anti-sense Primer Ptac-NotI (5'-AAAAAAGCGGCCGCGAAATTGTTATCCGCT CACAATTCC-3') (SEQ ID NO: 6) were used to amplify by PCR a 201 bp DNA-Fragment encoding Ptac-Promoter from pGEX-6p-1-Plasmid (Amersham Bioscience, Germany). The PCR was performed in T3 thermocycler (Biometra, Germany): for 30 cycles at 95° C. for 30 s, 55° C. for 30 s, and 72° C. for 90 s. Sense primer Rbs-NotI-forward (5'-AAAAAA GCGGCCGCTAAGGATGAATTATGATTAAATTAA AATTTGG-3') (SEQ ID NO: 7) and antisense-primer ctb-SalI-reverse (5'-TTTATA GTCGACTTAATTTGCCATACTAATTGCGGCAAT CGC-3') (SEQ ID NO: 8) were used to amplify by PCR the 413 bp DNA-Fragment encoding the ribosome binding site and the whole coding sequence of CtxB from *V. cholerae* E1 tor. The PCR was performed in a T3 Thermocycler (Biometra, Germany): step 1: 30 cycles at 95° C. for 30 s, 50° C. for 30 s, and 72° C. for 2 min. After purification with the Qiaquick PCR Purification Kit (Qiagen, Germany) and the digestion of both fragments with the NotI restriction enzyme, the two fragments were ligated resulting in the 594 by Ptac-ctxB-fragment. The resulting fragment was also purified and after digestion with the SalI restriction enzyme, the Ptac-ctxB-Fragment was inserted into the single Sall site of the export vector pMKhly-PSA. The resulting plasmid pMKhly-PSA/CtxB was isolated from *E. coli* DH5alpha (Invitrogene, Germany), analyzed and sequenced.

1D Cloning of PSA-CtxB-HlyAs Fusion Construct

Sense primer 5'ctxB NsiI (5'-GCATATGCAC ATGCATCACCTCAAAATATTACTGAT-3')(SEQ ID NO: 9) and anti-sense primer 3' ctxB SrfI NsiI (5'-GGCTTTTT-TATATCTT ATGCATGCCCGGGCATTGCGGCAATCGC-3') (SEQ ID NO: 10) (SrfI site is bold) were used to amplify by PCR a ~300 bp DNA fragment representing the ctxB gene from *V. cholerae* E1 tor. After purification with the QIAquick PCR Purification Kit (Qiagen, Germany) and digestion with the NsiI restriction enzyme, the DNA fragment, carrying the whole ctxB gene without the N-terminal signal sequence, was inserted into the single NsiI site of the export vector pMKhly1. The resulting plasmid pMKhly-CtxB was isolated from *E. coli* DH5alpha (Life Technologies), analyzed and sequenced. The human psa gene was amplified from plasmid pCDNA3PSA by PCR with primers 5-PSA-Blunt (5'-GTGG-GAGGC TGGGAGTGC-3) (SEQ ID NO: 11) and 3-PSA-Blunt (5'-GGGGTTGGCCACGATGGT-3) (SEQ ID NO: 12). PCR was carried out in a Thermal Cycler 60 (Biometra, Gottingen, Germany) for 30 cycles at 94° C. for 1 min, 56° C. for 1 min, and 72° C. for 2 min. The 0.7 kb DNA product was subsequently cloned into the SrfI site of pMKhly-CtxB. The resulting plasmid pMKhly-CtxB-PSA was verified by restriction analysis and sequencing.

1E Expression and Secretion of Fusion Proteins in Different Bacterial Species

Using standard electroporation procedures, plasmid pMKhly-CtxB-PSA was transformed into different electrocompetent bacterial strains. Kanamycin resistant single colonies were picked and grown in BHI medium (Beckton Dickinson, USA: Calf Brains, Infusion from 200 g, 6.0 g/L; Beef Heart, Infusion from 250 g, 9.8 g/L; Proteose Peptone 10.0 g/L ; Sodium Chloride 5.0 g/L; Dextrose 2.0 g/L; Disodium Phosphate 2.5 g/L) to a density of $1\times10^9$ cells per ml. Following growth 20 ml of culture were centrifuged for 30 min at 4000 rpm (3000 g) in a Heraeus centrifuge at 4° C. 18 ml of the supernatant were transferred into a fresh tube. Subsequently, 1.8 ml TCA (trichloroacetic acid, Applichem, Germany) were added, the liquid was mixed and incubated for at least 1 hour on ice. After incubation, the suspension was centrifuged for 30 min at 4000 rpm (3000 g) in a Heraeus centrifuge at 4° C. The supernatant was decanted and the pellet was washed with 1 ml acetone p.a. (Applichem, Germany). The precipitate was centrifuged for 10 min at 4000 rpm (3000 g) in a Heraeus centrifuge at 4° C. The pellet was air-dried and taken up in 150 μl 5× Laemmli buffer (70 mM Tris-HCl, pH 6.8, 40% (v/v) glycerol, 3% (v/v) sodium dodecyl sulfate, 5% (v/v) 2-mercaptoethanol and 0.05% (w/v) bromophenol blue) with or without beta-mercaptoethanol (Laemmli, 1970). 20 μl of solution were used for each lane in SDS PAGE. The separated proteins were electrophoretically transferred (Western blot) to Hybond ECL nitrocellulose membrane (Amersham-Pharmacia, Little Chalfont, UK) and blocked overnight with PBS (Potassium chloride 0.20 g/l, Potassium dihydrogen phosphate 0.20 g/l, Sodium chloride 8.00 g/l, di-Sodium dihydrogen phosphate anhydrous 1.15 g/l) containing 1% BSA. The membrane was washed in PBS-Tween 0.05%, incubated with polyclonal rabbit anti PSA antibody (1:750, DAKO, Denmark), CtxB antibody (1:1000, Zytomed, Berlin, Germany) or HlyAs antibody (Gentschev et al., 1996)) and subsequently incubated with HRP-coupled anti rabbit IgG (1/2,000; Dianova, Hamburg, Germany) for 1 h. The Western blot was developed with the enhanced chemiluminescence kit (GE Healthcare Life Science, Germany).

FIG. 11 depicts the functional expression and secretion of PSA-CtxB fusion proteins in a variety of bacterial strains, including *Escherichia coli* spp., *Salmonella dublin, Citrobacter* spp, *Salmonella typhi* Ty21a, *Salmonella typhimurium* spp, *Erwinia* spp and *Shigella flexneri* spp.

The *Salmonella typhi* Ty21a strain expressing and secreting PSA-CtxB fusion protein was deposited at German Collection of Microorganisms and Cell Cultures (DSMZ) under DSM 19244.

Example 2

Immune Response and Protection Against Tumor Cell Challenge in Mice Immunized with *Salmonella* Strains Secreting Fusion Proteins of Tumor Antigens and CtxB or CtxB Alone By the following experiments the superior protective efficacy of secreted fusion proteins of tumor antigens and protein toxins was demonstrated in an animal tumor model. For this model, the strain *Salmonella typhimurium* aroA (SL7207) pMKhly-CtxB-PSA, expressing and secreting the CtxB-PSA fusion protein was compared with other control strains.

2A Immunization Procedures

DBA/2 mice were immunized three times with an interval of 3 weeks. For the immunization with bacteria, animals were pre-treated by applying 50 μl 7% $NaHCO_3$ intragastrically to increase the intragastric pH. 5 to 10 minutes after pre-treatment, $5 \times 10^8$ live, Kanamycin-insensitive bacteria were applied in a volume of 100 μl PBS intragastrically. As a control, mice were immunized intramuscularly with naked plasmid DNA encoding PSA (pcDNA-PSA) as described in (Fensterle et al., 2005).

2B T-Cell Responses

Seven days after the last immunization, splenocytes of immunized mice were prepared as published previously (Fensterle et al., 1999) by passaging the spleen through a mesh followed by lysis of erythrocytes. ELISPOT analysis for the detection of PSA specific $CD8^+$ T-cells was performed according to a protocol published in (Fensterle et al., 1999).

In brief, for the ex-vivo analysis of PSA specific $CD8^+$ T-cells 96-well nitrocellulose plates (Millititer H A; Millipore, Bedford, Mass.) were coated with 5 μg/ml of the anti-mouse IFN-gamma monoclonal antibody (mAb) R4 (PharMingen) in 100 μl of carbonate buffer (Fensterle et al., 1999), pH 9.6. After overnight incubation at 4° C. and blocking with 1% BSA in PBS, $1 \times 10^5$ splenocytes from vaccinated mice were added in 100 μl RP10 (Fensterle et al., 1999) per well.

For analysis of the $CD8^+$ T-cell response the PSA expressing P815 cell clone PPSA 24 was used; in brief, this clone expresses the full length PSA via a CMV promotor encoded by the plasmid pCDNA3 (Fensterle et al., 2005). After incubation for 20-22 h at 37° C., 5% $CO_2$ in the presence of 30 U/ml IL-2, plates were washed and incubated for additional 2 h with 100 μl biotinylated anti-mouse IFN-gamma mAb XMB 1.2 (0.25 μg/ml, PharMingen). Plates were washed and incubated for 1 h at 37° C. in the presence of 100 μl of a 1/20,000 dilution of alkaline phosphatase-coupled streptavidin (PharMingen). Spots were visualized by adding 50 μl of the ready-to-use substrate BCIP/NBT (Sigma, St. Louis, Mo.) dissolved in water. Spots were counted under a dissecting microscope at 3-fold magnification.

The frequency of peptide-specific T cells (CTL) is expressed as the number of IFN-gamma-secreting cells per $10^5$ splenocytes. For the analysis of T-cell responses after restimulation, $2.5 \times 10^7$ splenocytes were restimulated with $2 \times 10^6$ irradiated PSA expressing P815 cells (Fensterle et al., 2005) in RP10 medium (Fensterle et al., 1999) in the presence of 60 U/ml recombinant IL-2 for 5 days. ELISPOT analysis was performed as described above using various amounts of restimulated cells ($10^5$, $3 \times 10^4$, $10^4$ or $3 \times 10^3$ per well) mixed with $4 \times 10^5$ feeder cells (=freshly prepared splenocytes from naïve DBA/2 mice) and $10^5$ PPSA24 cells.

The induction of a cellular immune response, especially of $CD8^+$ cytotoxic T cells, plays an important role for the efficiency of tumor therapy (Boon et al., 2006; Rosenberg, 2001). Therefore, the efficacy of the recombinant bacterial strain *Salmonella typhimurium* (SL7207) carrying a pMKhly-CtxB-PSA expression vector to induce a PSA-specific $CD8^+$ T-cell immune response was first tested.

For this purpose 64 female DBA-2 mice at the age of 10-14 weeks were immunized p.o. with recombinant SL7207/pMKhly-CtxB (n=10), SL7207/pMKhly-CtxB-PSA (n=10), SL7207/pMKhly-PSA (n=10), SL7207/pMKhly-PSA/CxtB (n=10), SL7207/pMKhly1 (n=7) and naked pcDNA3-PSA (n=10) as a positive control as described herein.

Figure 12:
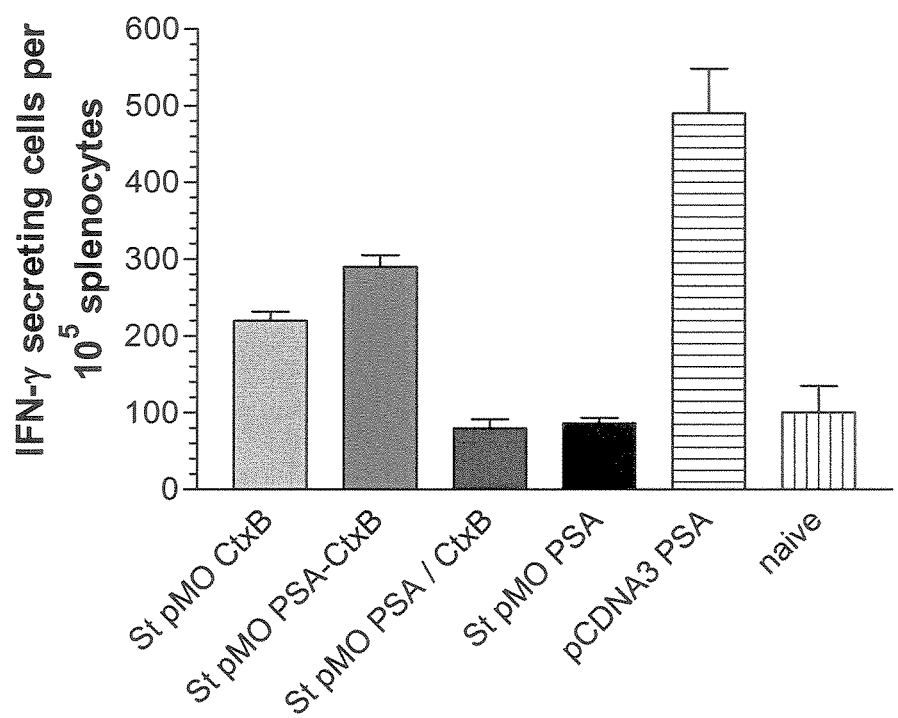
FIG. 12 depicts IFN-gamma secreting splenocytes as a measure for CD8+ T-cell and innate immune system (NK cell) responses in mice immunized with different live vaccine carriers.

FIG. 12 shows the ELISPOT data revealing that DNA immunized mice showed profound $CD8^+$ T-cell responses. After restimulation, marked immune responses were detected in animals vaccinated with *Salmonella* secreting PSA protein fused to CtxB, but not in strains secreting PSA alone or PSA and CtxB separately. Interestingly, animals vaccinated with *Salmonella* secreting CtxB toxin alone also showed significant immune responses after restimulation. These responses are most likely due to NK cells or other cells of the innate immune system, which non-specifically recognize the target cell line. Hence, from the data for secreted CtxB alone it can be concluded that the immune response observed for secreted CtxB-PSA fusion protein (IFN-gamma secreting splenocytes) is composed of a CD8+ T-cell response as well as a profound response of the innate immune system (most likely NK cells).

2C Protection Against Tumor Cell Challenge

To analyze the protective capacity of the immunization, 6-7 mice per group were immunized according to the schedule above. Two weeks after the third immunization, mice were challenged with PPSA 24 (see above) by two s.c. injection of $1 \times 10^6$ cells into each flank of shaven abdominal skin. Mice were monitored over a period of 14 days for tumor appearance and tumor volume was assessed by measuring the largest (a) and smallest (b) tumor diameter. Tumor volume was calculated as rotation ellipsoid using the following formula:

$$V = \frac{\pi}{6} * a * b^2, a > b.$$

Results were analyzed for significance by one way ANOVA and Dunnett's multiple comparison post-test using the Graph Pad Prism software. The post test was only performed when ANOVA revealed significance.

Figure 13:
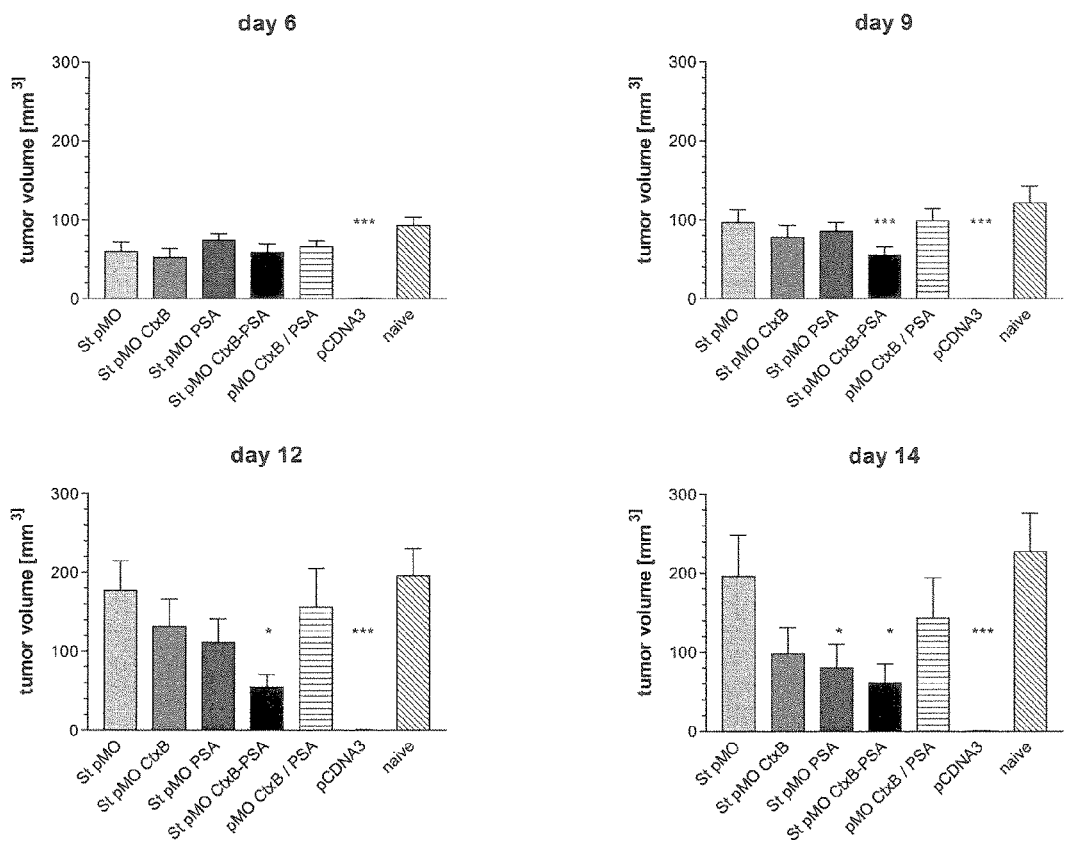
FIG. 13 depicts the reduction of tumor volume in response to immunization with different live vaccine carriers.

FIG. 13 displays the results as means+/−SD. At day 6, 9, 12 and 14 significant protective effects were observed. As expected, naked DNA vaccination included as a control completely protected mice from tumor growth. However, naked DNA vaccination shows at most moderate efficiency in humans. Regarding the bacterial constructs, the vaccine strain SL7207/pMKhly-CtxB-PSA (expressing and secreting the CtxB-PSA fusion protein) turned out to be most efficient. It significantly reduced tumor volume at day 9, 12 and 14 after tumor challenge. Of note, also the strain SL7207/pMKhly-CtxB reduced tumor growth with values comparable to SL7207/pMKhly-CtxB-PSA at day 14. Although not significant, this delayed effect is well compatible to the cellular response which was measured in the ELISPOT assay. Furthermore, also the SL7207/pMKhly-PSA strain achieved significant protection at day 14 which indicates, that also this strain induced a T-cell response which was below the detection threshold. In contrast, the SL7207/pMKhly-PSA/CxtB strain did not induce a relevant effect and remained in the same range as SL7207/pMKhly1 alone.

Example 3

Expression and Secretion of an Oncogen—Toxin Fusion Protein in *S. Typhi* Ty21a Analogous to example 1, another tumor antigen, the kinase domain of the oncogen B-Raf V600E with a 10 as deletion in the kinase domain was used (BRaf V600E kinase domain kinase dead (KD), or briefly BRaf* KD, more briefly BKD). This oncogen and protein toxin components, here CtxB, as adjuvant, a BKD-CtxB fusion protein was constructed as described herein. Expression and secretion was demonstrated in the human vaccine strain *S. typhi* Ty21a. The molecular cloning is based on the plasmid/expression vector pMOhly1, which has been previously described (Gentschev et al., 2005; Gentschev et al., 1996) and the cloning procedure is analogous to example 1 in this application. The resulting vector is named pMBKDC. The sequence of the fusion protein is given in FIG. 10.

Figure 17:
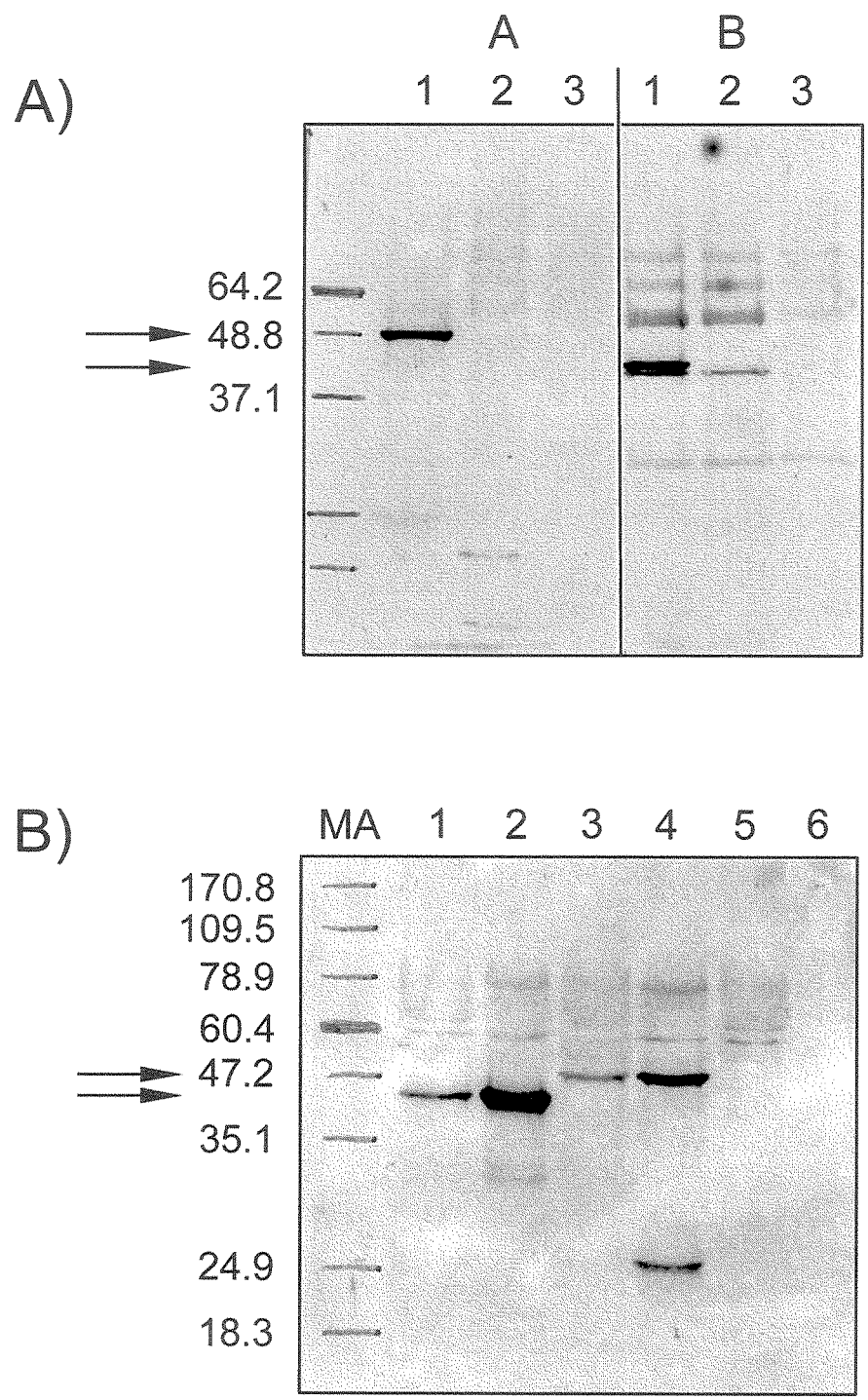
FIG. 17 depicts the expression and secretion of the fusion protein using the vector pMBKDC electroporated into the strain *Salmonella typhi* Ty21a and other bacterial strains.

FIG. 17 depicts the expression and secretion of the fusion protein using the vector pMBKDC electroporated into the strain *Salmonella typhi* Ty21a and other bacterial strains.

The *Salmonella typhi* Ty21a strain expressing and secreting BKD-CtxB fusion protein was deposited at German Collection of Microorganisms and Cell Cultures (DSMZ) under DSM 19245.

Example 4

Comparison of an OVA-CtxB Fusion Construct with Different Genetically Encoded Immunological Adjuvants To compare the immunological efficacy of toxin-antigen fusion proteins secreted by live vaccines, a fusion protein encompassing a widely used antigen for immunological studies, chicken ovalbumin (OVA) and CtxB was constructed.

Sense primer NsiI-OVA-forward 5'-CAT GTA TGC ATT AGC CAT GGT ATA CCT GG-3' (SEQ ID NO: 13) and anti-sense primer NsiI-OVA-reverse 5'-TTT TTT ATG CAT AAG GG AAA CAC CAC ATC TGC C-3' (SEQ ID NO: 14) were used to amplify by PCR a 1033 bp DNA fragment representing the ova gene (NM205152). After purification with the QIAquick PCR Purification Kit (Qiagen, Germany) and digestion with the NsiI restriction enzyme, the DNA fragment, carrying the whole ova gene without the N-terminal signal sequence, was inserted into the single NsiI site of the export vector pMKhly1. The resulting plasmid pMKhly-Ova was isolated from *E. coli* DH5alpha (Life Technologies), analyzed and sequenced.

Sense primer 5'ctxB NsiI (5'-GCATATGCAC ATGCATCACCTCAAAATATTACTGAT-3)(SEQ ID NO: 9) and anti-sense primer 3' ctxB SrfI NsiI (5'-GGCTTTTT-TATATCTT ATGCATGCCCGGGCATTGCGGCAATCGC-3') (SEQ ID NO: 10) (SrfI site is bold) were used to amplify by PCR a ~300 bp DNA fragment representing the ctxB gene from *V. cholerae* E1 tor. After purification with the QIAquick PCR Purification Kit (Qiagen, Germany) and digestion with the NsiI restriction enzyme, the DNA fragment, carrying the whole ctxB gene without the N-terminal signal sequence, was inserted into the single NsiI site of the export vector pMKhly1. The resulting plasmid pMKhly-CtxB was isolated from *E. coli* DH5alpha (Life Technologies), analyzed and sequenced. The ova gene was amplified from the pCI-OVA plasmid by PCR using 5-OVA-SfrI GCC ATC ATG TCA GCT CTA (SEQ ID NO: 15) and 3-OVA-SfrI AGG GGA AAC ACA TCT GCC (SEQ ID NO: 16) primers. The PCR was carried out in a Thermal Cycler 60 (Biometra, Göttingen, Germany) for 30 cycles of 1 min at 94° C., of 1 min at 49° C., and of 2 min. 30 sec at 72° C. The 1.1-kb DNA product was subsequently cloned into the SrfI site of pMKhly-CtxB. The resulting pMKhly-CtxB-OVA plasmid was examined by restriction analysis and sequencing.

The capacity of this fusion protein to elicit Th1 immune responses was compared with those of pMKhly vector encoded secreted OVA alone in combination with DNA delivery plasmids (encoding for proteins under the control of a eukaryotic promotor) coding for interferons (IFN-gamma), interleukins (IL-12) and chemokines (IP-10).

Immunization procedures and ELISPOT analysis were performed as described above. In brief, C57BL/6 mice were immunized orally three times with the different strains. 7 days after final immunization, splenocytes were removed, restimulated for 5 days and analysed in an ELISPOT assay. For restimulation of splenocytes, cells pulsed with the SIINFEKL peptide (letters stand for amino acids), the H-$2^b$ restricted MHC-I epitope of ovalbumin, were used.

Figure 14:
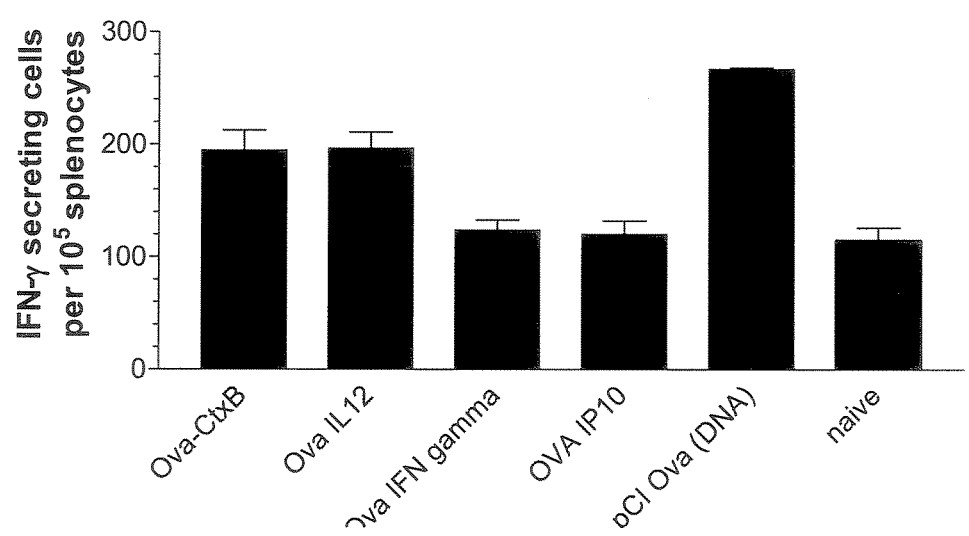
FIG. 14 depicts IFN-gamma secreting splenocytes as a measure for CD8+ T-cell and innate immune system (NK cell) responses in mice immunized with different live vaccines carrying different immunological adjuvants with CtxB-OVA fusion constructs.

FIG. 14 shows the superior efficacy of the fusion protein comprising chicken ovalbumin (OVA) and CtxB in inducing OVA specific CD8$^+$ T-cell responses and potentially innate immune system) responses compared to constructs co-delivering IFN-gamma or IP-10. It exhibits a similar efficacy as the strain with co-delivered IL-12 construct.

Example 5

Expression and Secretion of Viral Antigens

The suitability of the microorganisms of the invention for the expression and secretion of any (non-tumor) antigen was demonstrated through the expression of hemagglutinin H1 protein of the chicken influenza virus H5N1 fused to CtxB in a veterinary vaccine strain, Salmonella typhimurium VacT.

Sense primer 5'-HA-G: 5'-ATC TGT CAA ATG GAG AAA-3' (SEQ ID NO: 17) and anti-sense primer 3-HA12C: 5'-TAC TCC ACT TAT TTC CTC TCT-3' (SEQ ID NO: 18) were used in PCR, amplifying a DNA fragment encoding the H5 without the C-terminal membrane domain (H12C). The PCR product was subsequently cloned into the SrfI site of pMKhly-CtxB. The resulting pMKhly-CtxB-H12C plasmid was examined by restriction analysis and sequencing. The *S. typhimurium* VacT/pMKhly-CtxB-H12C strain efficiently expressed and secreted the hybrid H5-protein, as shown by immunoblotting with polyclonal antibodies raised against CtxB and HlyA (FIG. 2). The amount of secreted H5 was 2-3 μg protein/ml supernatant under the experimental conditions.

Bacteria were grown in BHI medium to a density of $1 \times 10^9$ cells per ml. 20 ml of the culture were centrifuged for 30' at 4000 rpm (3000 g) and 4° C. in a Hereaus centrifuge. 18 ml of the supernatant were transferred into a fresh tube. Subsequently, 1.8 ml TCA (trichlor-acetic acid, Applichem, Germany) were added; the liquid was mixed and incubated on ice for at least 1 hour. After incubation, the suspension was centrifuged for 30' at 4000 rpm (3000 g) and 4° C. in a Hereaus centrifuge. The supernatant was decanted and the pellet was washed with 1 ml Aceton p.a. (Applichem, Germany); the precipitate was centrifuged for 10' at 4000 rpm (3000 g) and 4° C. in a Hereaus centrifuge. The pellet was air-dried and taken up in 150 μl 5× Laemmli-buffer. 20 μl of the solution were used for each lane in SDS PAGE. The separated proteins were electrophoretically transferred to Hybond ECL nitrocellulose membrane (Amersham-Pharmacia, Little Chalfont, U.K.) and blocked overnight with PBS containing 1% BSA.

The membrane was washed in PBS-Tween 0.05%, incubated with polyclonal rabbit anti CtxB antibody (1:1000, Zytomed, Berlin, Germany) or HlyAs antibody (Gentschev et al., 1996) and subsequently incubated with HRP-coupled anti rabbit IgG (1/2,000; Dianova, Hamburg, Germany) for 1 h. The Western blot was carried out using the enhanced chemiluminescence kit (GE Healthcare Life Science, Germany).

Figure 15:
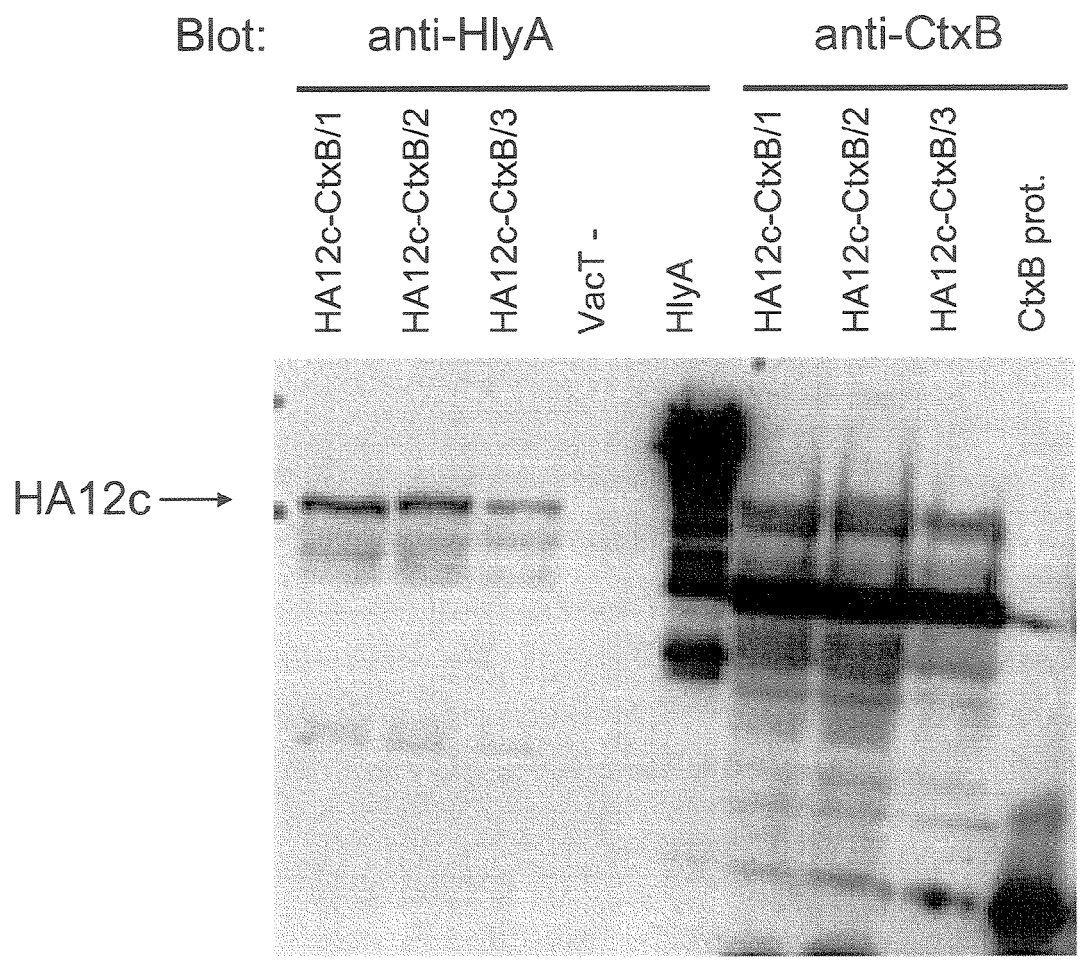
FIG. 15 depicts the efficient expression and functional secretion of chicken influenza hemagglutinin H1-CtxB fusion proteins in a veterinary vaccine strain encompassing the full sequence of H5N1 haemaglutinin (HA1+HA2, depicted, HA12), without the transmembrane region (HA12c). Live attenuated *Salmonella enterica* serovar *Typhimurium* vacT (gyrA D87G) and live attenuated *Salmonella enterica* serovar Enteritidis vacE, (strain Sm24/Rif12/Ssq), both LOHMANN ANIMAL HEALTH GMBH & CO KG

FIG. 15 depicts the efficient expression and functional secretion of HA12C-CtxB fusion protein in the veterinary vaccine strain, Salmonella typhimurium VacT.

Example 6

Expression and Secretion of Fusion Proteins of Toxin Adjuvants and Tumor Antigens Via Type III Secretion Systems Several Gram negative bacteria carry type III secretion systems which can be exploited for antigen secretion. Usually, these systems can be exploited to directly inject heterologous antigens into cells. In this example, a toxin component of Yersinia which serves as secretion signal (YopE)) is genetically fused to the heat labile enterotoxin sub-unit B (LT-B) fragment serving as an adjuvant and a tumor antigen, PSA. This construct is to be expressed in suitable, preferably attenuated, *Yersinia* strains which leads to secretion of the fusion protein by the endogenous type III secretion machinery via the YopE signal sequence.

In this example, the genetic fusion YopE18-LT-B-PSA is cloned into the EcoRI site of the plasmid paCYC184, for use the construct with the same orientation as the cat gene is used yielding a product expressed by the plasmid encoded cat promoter (http://www.fermentas.com/techinfo/nucleicacids/mappacyc184.htm). For enhanced expression, any suitable promotor can be used.

In the following, a cloning procedure is exemplified. Chromosomal DNA from *E. coli* encompassing the heat labile enterotoxin subunit B or a vector encompassing this sequence (GenBank accession number AF242418) is amplified using the following primers in a PCR reaction:

Eco-yope18-f (Encompassing EcoRI Site+YopE18 Signal Sequence):

```
                                        (SEQ ID NO: 19)
5'-
CTGAATTCATGAAAATATCATCATTTATTTCTACATCACTGCCCCTGC-
CGGCA TCAGTGTCAAATAAAGTAAAATGTTATGTTTTAT 3'
```

(5' region black: EcoRI site+3 bases 5', red: sequence encoding for secretion signal for type III secretion of YopE protein (aa 1-18), GenBank Accession M92066; italic region: homology region of LT-B gene (GB accession AF242418), bases 4-28).

Phosphorylated Reverse Primer LT-B-r:

```
                                        (SEQ ID NO: 20)
     5' GTTTTCCATACTGATTGCCGCAATTGAATTGG-3'
```

(reverse strand 372-341 of GB AF242418).

In parallel, the PSA sequence as described in this application from the vector pMK CtxB-PSA is amplified using the following primers:

```
phosphorylated forward primer psa-f:
                                        (SEQ ID NO: 21)
5'-GTGGGAGGCTGGGAGTGCGAG-3' reverse primer psa-eco-r:
                                        (SEQ ID NO: 22)
5' CCTGAATTCTTAGACGTGATACCTTGAAGCAC
```

(5' black: EcoRI site+3 bases 5', blue: stop codon, black: 3' region of PSA sequence, this application)

Subsequently, the two fragments are ligated with a DNA Ligase under the appropriate conditions. After ligation, the new fragment is amplified in a second PCR reaction using the Eco-yope18-f and PSA-Eco-R primers described above.

The resulting fragment is purified using a suitable PCR purification kit to remove buffer and oligonucleotides and subsequently digested with EcoRI enzyme in suitable reaction conditions. The resulting 1040 bp fragment is purified using agarose gel electrophoresis in ligated into the EcoRI digested vector paCYC 184. After sequencing tetracyclin resistant, cm sensitive clones, a clone which has the correct sequence integrated with the same orientation than the cm gene is chosen and transformed into a suitable Yersinia strain using electroporation. This vaccine strain will secrete the LT-B-PSA fusion via its endogenous type III secretion system.

Example 7

Expression and Secretion of Toxin-Antigen Fusions in Gram Positive Bacteria

Gram positive and negative bacteria have different prerequisites for secretion. Gram negative bacteria possess two membranes and therefore a secretion machinery in addition to secretion signals is mandatory for full secretion. In the case of Gram positive bacteria, a secretion signal sequence is sufficient.

In this example a system for secretion of a Tetanus-toxoid PSA fusion in *Listeria* using the p60 secretion signal is described.

In a first step, the vector pUC18(PS)actAOVATin1A (Loeffler et al., 2006) is digested using NsiI and subsequently treated with 3'-5' Exonuclease in the appropriate conditions. Finally, the fragment is purified by agarose gel electrophoresis.

In parallel, the tetanus toxoid fragment C (GenBank accession no. M12739) is amplified from a suitable source, e.g. genomic DNA from a *Clostridium tetanii* strain using the following phosphorylated primers:

```
tetc for:
                                        (SEQ ID NO: 23)
5'- TAAAAATCTGGATTGTTGGGTTG -3',
``` whereas the underlined additional base is to ensure the correct frame of the fusion.

```
tetc rev:
                                        (SEQ ID NO: 24)
5'- ATCATTTGTCCATCCTTCATCTG -3'.
```

The BRAF KD fragment is amplified from the plasmid pMO BKDC described in this application using the following phosphorylated primers:

```
br for:
5'- GATTGGGAGATTCCTGATG -3'         (SEQ ID NO: 25)

br rev:
5'- CCCGTGGACAGGAAACGCACC -3'.      (SEQ ID NO: 26)
```

Both fragments are purified using a suitable PCR purification kit and subsequently ligated with DNA ligase under suitable conditions. After ligation, the fragment is purified again using a suitable PCR purification kit and amplified using the tetc for and the br rev primer. After amplification, the resulting 2280 bp fragment is purified by agarose gel electrophoreses and ligated into the purified NsiI-3'-5' exonuclease fragment of pUC18(PS)actAOVATin1A. After ligation and transformation into E. coli, a clone is selected carrying the fragment in frame. Subsequently, the plasmid is cut using PstI and SacI and the 2837 bp fragment is purified using gel electrophoresis and ligated into the appropriately PstI and SacI digested and purified vector pSP118 (Loeffler et al., 2006).

The resulting vector, pSP118-act-TetC-BRaf*KD is transformed into a Listeria strain carrying a trpS deletion e.g. Listeria monocytogenes delta trps delta aroA/B (Loeffler et al., 2006). In this setting, the plasmid is stabilized via the plasmid based trpS ("Balanced lethal system") and the plasmid encodes for a phage lysine which leads to intracellular lysis of the strain. The act-TetC-BRaf*KD cassette is expressed mainly in eukaryotic host cells under the control of the actA promoter, which has some extracellular leakiness (Loeffler et al., 2006). The actA signal sequence of the cassette leads to secretion of the TetC-BRaf*KD fusion protein.

Example 8

Eukaryotic Cells Secreting Toxin-Antigen Fusions

In this example, a eukaryotic cell line, eg tumor cell line, is constructed which secretes a CtxB-PSA fusion protein. For this purpose, a universal secretion signal is employed (U.S. Pat. No. 6,733,997), which, in principle, allows the secretion of the corresponding expression cassette in cells of different origin, including mammalian cells, yeast and procaryotic cells.

In a first step, the CtxB-BRaf*KD fusion is amplified from the plasmid pMO BKDC (this application) using the following primers:

```
CB-for:
                                    (SEQ ID NO: 27)
5'- atcGGATCCTCAAAATATTACTGATTTGTGTGC -3'
(lower case: spacer, underlined: BamHI site,
uppercase: CtxB 5')

CB-rev:
                                    (SEQ ID NO: 28)
5'- tagGGATCCTTAGTGGACAGGAAACGCACCATATCC -3'
(lower case: spacer, underlined: BamHI site,
italic: stop codon, uppercase: BRaf* KD 3').
```

Subsequently, the PCR product is purified using a suitable PCR purification kit and subsequently partially digested (fragment contains internal BamHI site) with BamHI. The 1231 bp fragment of the partial digest is isolated via agarose gel electrophoresis and subsequently ligated into the BamHI digested and gel purified plasmid pVtgEGFP (U.S. Pat. No. 6,733,997). Subsequently, a clone carrying the in frame orientation with Vtgss is selected and named pVtgCtxBRAf. This plasmid can be transformed via electroporation into a eukaryotic cell line, which can be selected via the kan/neo selection cassette. The cell lines can be established cell lines like cancer cell lines for use as heterologous cancer vaccine or patient derived tumor cells for use as autologuous cancer vaccines.

In any case, the secretion signal Vtgss encoded by the vector pVtgEGFP genetically fused to CtxB-BRaf* KD will result in the secretion of the fusion protein.

Using a similar approach, fusion proteins can also be expressed in yeast. As an example, a modified cloning strategy as depicted in FIG. 11 of U.S. Pat. No. 6,733,997 is demonstrated. In the first step, the cassette containing the Vtgss-CtxB-BRaf*KD fusion from plasmid pVtgCtxBRAf described above is excised via EagI and Eco47III and inserted into the vector pBSPGK (U.S. Pat. No. 6,733,997, FIG. 11). Subsequently, the resulting vector is digested with SacI and HindIII and the fragment encompassing the PGK element and the Vtgss-CtxB-BRaf*KD fusion is integrated in the corresponding region of the vector pYEX-S1 analoguous to the description of U.S. Pat. No. 6,733,997 (FIG. 11). The resulting plasmid can be transformed by electroporation in yeast strains like Saccharomyces cerevisiae. The yeast will express and secrete the fusion protein and can be used for vaccination purposes.

Abbreviations
ABC ATP binding cassette
AIDA adhesin involved in diffuse adherence
APC Antigen-presenting cell
aroA aroA gene
AT alphaToxin
ATP adenosine triphosphate
B-Raf KD B-Raf kinase domain
BSA bovine serum albumin
Cag A major disease-associated virulence protein of Helicobacter pylori
CPE Clostridium perfringens enterotoxin
CpG DNA sequences containing hypomethylated immunstimulatory DNA sequences encompassing CpG motives
CT/Ctx Cholera Toxin
CTB/CtxB Cholera Toxin subunit B
CTL cytotoxic CD8 T cells (T killer cells)
CMV Cytomegalievirus
DNA desoxyribonucleic acid
ds double-stranded
DT/Dtx Diphetaria Toxin
E. coli Escherichia coli
EBV Ebstein Barr virus
GM-1 receptor Monosialoganglioside receptor 1
HA hemagglutinin
HCV Hepatitis C virus
HIV human immunodeficiency virus
Hly hemolysin
HPV Human Papilloma virus
HT Hemorrhagic Toxin
i.d. intradermally
i.m. intramuscular
i.p. intraperetoneally
IFN interferon
IgA Immunoglobulin isotype A
IgG Immunoglobulin isotype G
IL interleukin
KD kinase dead
LPS lipopolysaccharide
LT E. coli heat labile enterotoxin
LT Lethal toxin
LTB E. coli heat labile enterotoxin subunit B
mAb monoclonal antibody
MHC major histocompatibility complex NK cell natural killer cell
NKT cell natural killer T cell
PAGE polyacrylamide gel electrophoresis
PBS phosphate buffered saline
PCR Polymerase Chain Reaction
PSA prostate specific antigen
PT/Ptx *Pertussis* Toxin
RNA ribonucleic acid
s.c. subcutaneous
SDS sodium dodecylsulphate
Sec general secretory (Sec) pathway
ss single-stranded
ST *E. coli* heat stabile enterotoxin
ST/Stx Shiga Toxin
STB/StxB Shiga Toxin subunit B
T3SS type III secretion system
Tat twin-arginine translocation
TCA trichloroacetic acid
Th1 (cell) inflammatory CD4+ T cells
Th2 (cell) helper CD4+ T cells
TSST-1 Toxic shock syndrome toxin
TT Tetanus Toxin
VT Vero toxin
Literature Agren, L. C., Ekman, L., Lowenadler, B., Nedrud, J. G., and Lycke, N. Y. (1999). Adjuvanticity of the cholera toxin A1-based gene fusion protein, CTA1-DD, is critically dependent on the ADP-ribosyltransferase and Ig-binding activity. J Immunol 162, 2432-2440.

Anderson, R. J., Pasetti, M. F., Sztein, M. B., Levine, M. M., and Noriega, F. R. (2000). DeltaguaBA attenuated *Shigella flexneri* 2a strain CVD 1204 as a *Shigella* vaccine and as a live mucosal delivery system for fragment C of tetanus toxin. Vaccine 18, 2193-2202.

Austin, E. A., Graves, J. F., Hite, L. A., Parker, C. T., and Schnaitman, C. A. (1990). Genetic analysis of lipopolysaccharide core biosynthesis by *Escherichia coli* K-12: insertion mutagenesis of the rfa locus. J Bacteriol 172, 5312-5325.

Balsalobre, C., Silvan, J. M., Berglund, S., Mizunoe, Y., Uhlin, B. E., and Wai, S. N. (2006). Release of the type I secreted alpha-haemolysin via outer membrane vesicles from *Escherichia coli*. Mol Microbiol 59, 99-112.

Barry, E. M., Gomez-Duarte, O., Chatfield, S., Rappuoli, R., Pizza, M., Losonsky, G., Galen, J., and Levine, M. M. (1996). Expression and immunogenicity of *pertussis* toxin S1 subunit-tetanus toxin fragment C fusions in *Salmonella typhi* vaccine strain CVD 908. Infect Immun 64, 4172-4181.

Becerra, J. C., Arthur, J. F., Landucci, G. R., Forthal, D. N., and Theuer, C. P. (2003). CD8+ T-cell mediated tumor protection by *Pseudomonas* exotoxin fused to ovalbumin in C57BL/6 mice. Surgery 133, 404-410.

Boon, T., Coulie, P. G., Van den Eynde, B. J., and van der Bruggen, P. (2006). Human T cell responses against melanoma. Annu Rev Immunol 24, 175-208.

Boyd, A. P., Ross, P. J., Conroy, H., Mahon, N., Lavelle, E. C., and Mills, K. H. (2005). *Bordetella pertussis* adenylate cyclase toxin modulates innate and adaptive immune responses: distinct roles for acylation and enzymatic activity in immunomodulation and cell death. J Immunol 175, 730-738.

Brossier, F., Weber-Levy, M., Mock, M., and Sirard, J. C. (2000). Protective antigen-mediated antibody response against a heterologous protein produced in vivo by *Bacillus anthracis*. Infect Immun 68, 5731-5734.

Bumann, D. (2001). Regulated antigen expression in live recombinant *Salmonella enterica* serovar Typhimurium strongly affects colonization capabilities and specific CD4 (+)-T-cell responses. Infect Immun 69, 7493-7500.

Busby, S., and Ebright, R. H. (1994). Promoter structure, promoter recognition, and transcription activation in prokaryotes. Cell 79, 743-746.

Butterton, J. R., Beattie, D. T., Gardel, C. L., Carroll, P. A., Hyman, T., Killeen, K. P., Mekalanos, J. J., and Calderwood, S. B. (1995). Heterologous antigen expression in *Vibrio cholerae* vector strains. Infect Immun 63, 2689-2696.

Byun, Y., Ohmura, M., Fujihashi, K., Yamamoto, S., McGhee, J. R., Udaka, S., Kiyono, H., Takeda, Y., Kohsaka, T., and Yuki, Y. (2001). Nasal immunization with *E. coli* verotoxin 1 (VT1)-B subunit and a nontoxic mutant of cholera toxin elicits serum neutralizing antibodies. Vaccine 19, 2061-2070.

Campos, J., Martinez, E., Marrero, K., Silva, Y., Rodriguez, B. L., Suzarte, E., Ledon, T., and Fando, R. (2003). Novel type of specialized transduction for CTX phi or its satellite phage RS1 mediated by filamentous phage VGJ phi in *Vibrio cholerae*. J Bacteriol 185, 7231-7240.

Cardenas, L., and Clements, J. D. (1992). Oral immunization using live attenuated *Salmonella* spp. as carriers of foreign antigens. Clin Microbiol Rev 5, 328-342.

Cardenas, L., and Clements, J. D. (1993). Development of mucosal protection against the heat-stable enterotoxin (ST) of *Escherichia coli* by oral immunization with a genetic fusion delivered by a bacterial vector. Infect Immun 61, 4629-4636.

Chabalgoity, J. A., Harrison, J. A., Esteves, A., Demarco de Hormaeche, R., Ehrlich, R., Khan, C. M., and Hormaeche, C. E. (1997). Expression and immunogenicity of an *Echinococcus granulosus* fatty acid-binding protein in live attenuated *Salmonella* vaccine strains. Infect Immun 65, 2402-2412.

Chabalgoity, J. A., Khan, C. M., Nash, A. A., and Hormaeche, C. E. (1996). A *Salmonella typhimurium* htrA live vaccine expressing multiple copies of a peptide comprising amino acids 8-23 of herpes simplex virus glycoprotein D as a genetic fusion to tetanus toxin fragment C protects mice from herpes simplex virus infection. Mol Microbiol 19, 791-801.

Chabalgoity, J. A., Moreno, M., Carol, H., Dougan, G., and Hormaeche, C. E. (2000). *Salmonella typhimurium* as a basis for a live oral *Echinococcus granulosus* vaccine. Vaccine 19, 460-469.

Chabalgoity, J. A., Villareal-Ramos, B., Khan, C. M., Chatfield, S. N., de Hormaeche, R. D., and Hormaeche, C. E. (1995). Influence of preimmunization with tetanus toxoid on immune responses to tetanus toxin fragment C-guest antigen fusions in a *Salmonella* vaccine carrier. Infect Immun 63, 2564-2569.

Chacon, M. R., Londono, P., Dougan, G., and Selkirk, M. E. (1996). Heterologous expression of the cuticular-glutathione peroxidase of lymphatic filariae in an attenuated vaccine strain of *Salmonella typhimurium* abrogates H-2 restriction of specific antibody responses. Parasite Immunol 18, 307-316.

Chen, I., Finn, T. M., Yanqing, L., Guoming, Q., Rappuoli, R., and Pizza, M. (1998). A recombinant live attenuated strain of *Vibrio cholerae* induces immunity against tetanus toxin and *Bordetella pertussis* tracheal colonization factor. Infect Immun 66, 1648-1653.

Cheng-hua, S., Cheng, C., Jing-sheng, Z., Jiezhi., L., and Qing-jun, M. (1995). Gene fusion of cholera toxin B subunit and HBV PreS2 epitope and the antigenicity of fusion protein. Vaccine 13, 933-937.

Clemens, J., Savarino, S., Abu-Elyazeed, R., Safwat, M., Rao, M., Wierzba, T., Svennerholm, A. M., Holmgren, J., Frenck, R., Park, E., and Naficy, A. (2004). Development of pathogenicity-driven definitions of outcomes for a field trial of a killed oral vaccine against enterotoxigenic *Escherichia coli* in Egypt: application of an evidence-based method. J Infect Dis 189, 2299-2307.

Datsenko, K. A., and Wanner, B. L. (2000). One-step inactivation of chromosomal genes in *Escherichia coli* K-12 using PCR products. Proc Natl Acad Sci USA 97, 6640-6645.

Dietrich, G., Bubert, A., Gentschev, I., Sokolovic, Z., Simm, A., Catic, A., Kaufmann, S. H., Hess, J., Szalay, A. A., and Goebel, W. (1998). Delivery of antigen-encoding plasmid DNA into the cytosol of macrophages by attenuated suicide *Listeria monocytogenes*. Nat Biotechnol 16, 181-185.

Dietrich, G., Viret, J F, and Gentschev, I. (2003). Haemolysin A and listeriolysin—two vaccine delivery tools for the induction of cell-mediated immunity. Int. J. Parasitol 33, 495-505

Dunn, G. P., Old, L. J., and Schreiber, R. D. (2004). The immunobiology of cancer immunosurveillance and immunoediting. Immunity 21, 137-148.

Dunstan, S. J., Simmons, C. P., and Strugnell, R. A. (2003). In vitro and in vivo stability of recombinant plasmids in a vaccine strain of *Salmonella enterica* var. *Typhimurium*. FEMS Immunol Med Microbiol 37, 111-119.

Eriksson, A. M., Schon, K. M., and Lycke, N. Y. (2004). The cholera toxin-derived CTA1-DD vaccine adjuvant administered intranasally does not cause inflammation or accumulate in the nervous tissues. J Immunol 173, 3310-3319.

Fath, M. J., Skvirsky, R. C., and Kolter, R. (1991). Functional complementation between bacterial MDR-like export systems: colicin V, alpha-hemolysin, and *Erwinia* protease. J Bacteriol 173, 7549-7556.

Fensterle, J., Grode, L., Hess, J., and Kaufmann, S. H. E. (1999). Effective DNA vaccination against listeriosis by prime/boost inoculation with the gene gun. J Immunol 163, 4510-4518.

Fensterle, J., Schwartz, V., Riedmiller, H., and Rapp, U. R. (2005). Animal models for DNA vaccination against prostate cancer using PSA encoding plasmids. Onkologie 28 (suppl 2), 52.

Freytag, L. C., and Clements, J. D. (1999). Bacterial toxins as mucosal adjuvants. Curr Top Microbiol Immunol 236, 215-236.

Freytag, L. C., and Clements, J. D. (2005). Mucosal adjuvants. Vaccine 23, 1804-1813.

Garmory, H. S., Brown, K. A., and Titball, R. W. (2002). *Salmonella* vaccines for use in humans: present and future perspectives. FEMS Microbiol Rev 26, 339-353.

Garmory, H. S., Titball, R. W., Griffin, K. F., Hahn, U., Bohm, R., and Beyer, W. (2003). *Salmonella enterica* serovar *typhimurium* expressing a chromosomally integrated copy of the *Bacillus anthracis* protective antigen gene protects mice against an anthrax spore challenge. Infect Immun 71, 3831-3836.

Gentschev, I., Dietrich, G., and Goebel, W. (2002a). The *E. coli* alpha-hemolysin secretion system and its use in vaccine development. Trends Microbiol 10, 39-45.

Gentschev, I., Dietrich, G., Spreng, S., Pilgrim, S., Stritzker, J., Kolb-Maurer, A., and Goebel, W. (2002b). Delivery of protein antigens and DNA by attenuated intracellular bacteria. Int J Med Microbiol 291, 577-582.

Gentschev, I., Fensterle, J., Schmidt, A., Potapenko, T., Troppmair, J., Goebel, W., and Rapp, U. R. (2005). Use of a recombinant *Salmonella enterica* serovar *Typhimurium* strain expressing C-Raf for protection against C-Raf induced lung adenoma in mice. BMC Cancer 5, 15.

Gentschev, I., Mollenkopf, H., Sokolovic, Z., Hess, J., Kaufmann, S. H., and Goebel, W. (1996). Development of antigen-delivery systems, based on the *Escherichia coli* hemolysin secretion pathway. Gene 179, 133-140.

Gentschev, I., Dietrich, G., Spreng, S., Neuhaus, B., Maier, E., Benz, R., Goebel, W., Fensterle, J., and Rapp, U R. (2004). Use of the alpha-hemolysin secretion system of *Escherichia coli* for antigen delivery in the *Salmonella typhi* Ty21a vaccine strain. Int J Med Microbiol 294, 363-371.

Gomez-Duarte, O. G., Galen, J., Chatfield, S. N., Rappuoli, R., Eidels, L., and Levine, M. M. (1995). Expression of fragment C of tetanus toxin fused to a carboxyl-terminal fragment of diphtheria toxin in *Salmonella typhi* CVD 908 vaccine strain. Vaccine 13, 1596-1602.

Hajishengallis, G., Harokopakis, E., Hollingshead, S. K., Russell, M. W., and Michalek, S. M. (1996). Construction and oral immunogenicity of a *Salmonella typhimurium* strain expressing a streptococcal adhesin linked to the A2/B subunits of cholera toxin. Vaccine 14, 1545-1548.

Hajishengallis, G., Nawar, H., Tapping, R. I., Russell, M. W., and Connell, T. D. (2004). The Type II heat-labile enterotoxins LT-IIa and LT-IIb and their respective B pentamers differentially induce and regulate cytokine production in human monocytic cells. Infect Immun 72, 6351-6358.

Harokopakis, E., Hajishengallis, G., Greenway, T. E., Russell, M. W., and Michalek, S. M. (1997). Mucosal immunogenicity of a recombinant *Salmonella typhimurium*-cloned heterologous antigen in the absence or presence of coexpressed cholera toxin A2 and B subunits. Infect Immun 65, 1445-1454.

Hess, J., Gentschev, I., Miko, D., Welzel, M., Ladel, C., Goebel, W., and Kaufmann, S. H. (1996). Superior efficacy of secreted over somatic antigen display in recombinant *Salmonella* vaccine induced protection against listeriosis. Proc Natl Acad Sci USA 93, 1458-1463.

Holmgren, J., Adamsson, J., Anjuere, F., Clemens, J., Czerkinsky, C., Eriksson, K., Flach, C. F., George-Chandy, A., Harandi, A. M., Lebens, M., et al. (2005). Mucosal adjuvants and anti-infection and anti-immunopathology vaccines based on cholera toxin, cholera toxin B subunit and CpG DNA. Immunol Lett 97, 181-188.

Holmgren, J., and Czerkinsky, C. (2005). Mucosal immunity and vaccines. Nat Med 11, S45-51.

Holmgren, J., Czerkinsky, C., Eriksson, K., and Mharandi, A. (2003). Mucosal immunisation and adjuvants: a brief overview of recent advances and challenges. Vaccine 21 Suppl 2, S89-95.

Hormozi, K., Parton, R., and Coote, J. (1999). Adjuvant and protective properties of native and recombinant *Bordetella pertussis* adenylate cyclase toxin preparations in mice. FEMS Immunol Med Microbiol 23, 273-282.

Huang, Y., Hajishengallis, G., and Michalek, S. M. (2000). Construction and characterization of a *Salmonella enterica* serovar *typhimurium* clone expressing a salivary adhesin of *Streptococcus mutans* under control of the anaerobically inducible nirB promoter. Infect Immun 68, 1549-1556.

Hunt, P. D., and Hardy, S. J. (1991). Heat-labile enterotoxin can be released from *Escherichia coli* cells by host intestinal factors. Infect Immun 59, 168-171.

Jackson, R. J., Marinaro, M., VanCott, J. L., Yamamoto, M., Okahashi, N., Fujihashi, K., Kiyono, H., Chatfield, S. N., and McGhee, J. R. (1996). Mucosal immunity: regulation by helper T cells and a novel method for detection. J Biotechnol 44, 209-216.

Jagusztyn-Krynicka, E. K., Clark-Curtiss, J. E., and Curtiss, R., 3rd (1993). *Escherichia coli* heat-labile toxin subunit B fusions with *Streptococcus sobrinus* antigens expressed by *Salmonella typhimurium* oral vaccine strains: importance of the linker for antigenicity and biological activities of the hybrid proteins. Infect Immun 61, 1004-1015.

Khan, C. M., Villarreal-Ramos, B., Pierce, R. J., Demarco de Hormaeche, R., McNeill, H., Ali, T., Chatfield, S., Capron, A., Dougan, G., and Hormaeche, C. E. (1994a). Construction, expression, and immunogenicity of multiple tandem copies of the *Schistosoma mansoni* peptide 115-131 of the P28 glutathione S-transferase expressed as C-terminal fusions to tetanus toxin fragment C in a live aro-attenuated vaccine strain of *Salmonella*. J Immunol 153, 5634-5642.

Khan, C. M., Villarreal-Ramos, B., Pierce, R. J., Riveau, G., Demarco de Hormaeche, R., McNeill, H., Ali, T., Fairweather, N., Chatfield, S., Capron, A., and et al. (1994b). Construction, expression, and immunogenicity of the *Schistosoma mansoni* P28 glutathione 5-transferase as a genetic fusion to tetanus toxin fragment C in a live Aro attenuated vaccine strain of *Salmonella*. Proc Nal Acad Sci USA 91, 11261-11265.

Konieczny, M. P., Suhr, M., Noll, A., Autenrieth, I. B., and Alexander Schmidt, M. (2000). Cell surface presentation of recombinant (poly-) peptides including functional T-cell epitopes by the AIDA autotransporter system. FEMS Immunol Med Microbiol 27, 321-332.

Koprowski, H., 2nd, Levine, M. M., Anderson, R. J., Losonsky, G., Pizza, M., and Barry, E. M. (2000). Attenuated *Shigella flexneri* 2a vaccine strain CVD 1204 expressing colonization factor antigen I and mutant heat-labile enterotoxin of enterotoxigenic *Escherichia coli*. Infect Immun 68, 4884-4892.

Kweon, M. N., Yamamoto, M., Watanabe, F., Tamura, S., Van Ginkel, F. W., Miyauchi, A., Takagi, H., Takeda, Y., Hamabata, T., Fujihashi, K., et al. (2002). A nontoxic chimeric enterotoxin adjuvant induces protective immunity in both mucosal and systemic compartments with reduced IgE antibodies. J Infect Dis 186, 1261-1269.

Laemmli, U. K. (1970). Cleavage of structural proteins during the assembly of the head of bacteriophage T4. Nature 227, 680-685.

Lahiri, S. S. (2000). Bacterial toxins—an overview. J Nat Toxins 9, 381-408.

Lavelle, E. C., McGuirk, P., and Mills, K. H. (2004). Molecules of infectious agents as immunomodulatory drugs. Curr Top Med Chem 4, 499-508.

Lee, J. J., Sinha, K. A., Harrison, J. A., de Hormaeche, R. D., Riveau, G., Pierce, R. J., Capron, A., Wilson, R. A., and Khan, C. M. (2000). Tetanus toxin fragment C expressed in live *Salmonella* vaccines enhances antibody responses to its fusion partner *Schistosoma haematobium* glutathione 5-transferase. Infect Immun 68, 2503-2512.

Loeffler, D. I., Schoen, C. U., Goebel, W., and Pilgrim, S. (2006). Comparison of different live vaccine strategies in vivo for delivery of protein antigen or antigen-encoding DNA and mRNA by virulence-attenuated *Listeria monocytogenes*. Infect Immun 74, 3946-3957.

Loessner, M. J., Wendlinger, G., and Scherer, S. (1995). Heterogeneous endolysins in *Listeria monocytogenes* bacteriophages: a new class of enzymes and evidence for conserved holin genes within the siphoviral lysis cassettes. Mol Microbiol 16, 1231-1241.

Lycke, N. (2005). From toxin to adjuvant: basic mechanisms for the control of mucosal IgA immunity and tolerance. Immunol Lett 97, 193-198.

Lycke, N., Tsuji, T., and Holmgren, J. (1992). The adjuvant effect of *Vibrio cholerae* and *Escherichia coli* heat-labile enterotoxins is linked to their ADP-ribosyltransferase activity. Eur J Immunol 22, 2277-2281.

McSorley, S. J., Rask, C., Pichot, R., Julia, V., Czerkinsky, C., and Glaichenhaus, N. (1998). Selective tolerization of Th1-like cells after nasal administration of a cholera toxoid-LACK conjugate. Eur J Immunol 28, 424-432.

Mendelson, I., Gat, O., Aloni-Grinstein, R., Altboum, Z., Inbar, I., Kronman, C., Bar-Haim, E., Cohen, S., Velan, B., and Shafferman, A. (2005). Efficacious, nontoxigenic *Bacillus anthracis* spore vaccines based on strains expressing mutant variants of lethal toxin components. Vaccine 23, 5688-5697.

Mesnage, S., Weber-Levy, M., Haustant, M., Mock, M., and Fouet, A. (1999). Cell surface-exposed tetanus toxin fragment C produced by recombinant *Bacillus anthracis* protects against tetanus toxin. Infect Immun 67, 4847-4850.

Michalkiewicz, J., Stachowski, J., Barth, C., Patzer, J., Dzierzanowska, D., and Madalinski, K. (1999). Effect of *Pseudomonas aeruginosa* exotoxin A on IFN-gamma synthesis: expression of costimulatory molecules on monocytes and activity of NK cells. Immunol Lett 69, 359-366.

Michl, P., and Gress, T. M. (2004). Bacteria and bacterial toxins as therapeutic agents for solid tumors. Curr Cancer Drug Targets 4, 689-702.

Morona, R., Manning, P. A., and Reeves, P. (1983). Identification and characterization of the TolC protein, an outer membrane protein from *Escherichia coli*. J Bacteriol 153, 693-699.

Muhlen, K. A., Schumann, J., Wittke, F., Stenger, S., Van Rooijen, N., Van Kaer, L., and Tiegs, G. (2004). NK cells, but not NKT cells, are involved in *Pseudomonas aeruginosa* exotoxin A-induced hepatotoxicity in mice. J Immunol 172, 3034-3041.

Mutsch, M., Zhou, W., Rhodes, P., Bopp, M., Chen, R. T., Linder, T., Spyr, C., and Steffen, R. (2004). Use of the inactivated intranasal influenza vaccine and the risk of Bell's palsy in Switzerland. N Engl J Med 350, 896-903.

Orr, N., Galen, J. E., and Levine, M. M. (1999). Expression and immunogenicity of a mutant diphtheria toxin molecule, CRM(197), and its fragments in *Salmonella typhi* vaccine strain CVD 908-htrA. Infect Immun 67, 4290-4294.

Poggi, A., Spada, F., Costa, P., Tomasello, E., Revello, V., Pella, N., Zocchi, M. R., and Moretta, L. (1996). Dissection of lymphocyte function-associated antigen 1-dependent adhesion and signal transduction in human natural killer cells shown by the use of cholera or *pertussis* toxin. Eur J Immunol 26, 967-975.

Pogonka, T., Klotz, C., Kovacs, F., and Lucius, R. (2003). A single dose of recombinant *Salmonella typhimurium* induces specific humoral immune responses against heterologous *Eimeria tenella* antigens in chicken. Int J Parasitol 33, 81-88.

Ramirez, R., Carracedo, J., Zamzami, N., Castedo, M., and Kroemer, G. (1994). *Pertussis* toxin inhibits activation-induced cell death of human thymocytes, pre-B leukemia cells and monocytes. J Exp Med 180, 1147-1152.

Ranallo, R. T., Fonseka, C. P., Cassels, F., Srinivasan, J., and Venkatesan, M. M. (2005). Construction and characterization of bivalent *Shigella flexneri* 2a vaccine strains SC608

(pCFAI) and SC608(pCFAI/LTB) that express antigens from enterotoxigenic *Escherichia coli*. Infect Immun 73, 258-267.

Reveneau, N., Geoffroy, M. C., Locht, C., Chagnaud, P., and Mercenier, A. (2002). Comparison of the immune responses induced by local immunizations with recombinant *Lactobacillus plantarum* producing tetanus toxin fragment C in different cellular locations. Vaccine 20, 1769-1777.

Roland, K. L., Tinge, S. A., Killeen, K. P., and Kochi, S. K. (2005). Recent advances in the development of live, attenuated bacterial vectors. Curr Opin Mol Ther 7, 62-72.

Rosenberg, S. A. (2001). Progress in human tumour immunology and immunotherapy. Nature 411, 380-384.

Ryan, E. T., Butterton, J. R., Smith, R. N., Carroll, P. A., Crean, T. I., and Calderwood, S. B. (1997a). Protective immunity against *Clostridium difficile* toxin A induced by oral immunization with a live, attenuated *Vibrio cholerae* vector strain. Infect Immun 65, 2941-2949.

Ryan, E. T., Butterton, J. R., Zhang, T., Baker, M. A., Stanley, S. L., Jr., and Calderwood, S. B. (1997b). Oral immunization with attenuated vaccine strains of *Vibrio cholerae* expressing a dodecapeptide repeat of the serine-rich *Entamoeba histolytica* protein fused to the cholera toxin B subunit induces systemic and mucosal antiamebic and anti-*V. cholerae* antibody responses in mice. Infect Immun 65, 3118-3125.

Sanchez, J., Wallerstrom, G., Fredriksson, M., Angstrom, J., and Holmgren, J. (2002). Detoxification of cholera toxin without removal of its immunoadjuvanticity by the addition of (STa-related) peptides to the catalytic subunit. A potential new strategy to generate immunostimulants for vaccination. J Biol Chem 277, 33369-33377.

Sanchez, A E., Aquino, G., Ostoa-Saloma, P., Laclette, J P., and Rocha-Zavaleta, L. (2004). Cholera toxin B-subunit gene enhances mucosal Immunoglobulin A, Th1-type and CD8+ cytotoxic responses when co-administered intradermally with a DNA vaccine. Clinic Diagnost Laborat Immun 11, 711-719.

Schmid-Grendelmeier, P., and Crameri, R. (2001). Recombinant allergens for skin testing. Int Arch Allergy Immunol 125, 96-111.

Schodel, F., Enders, G., Jung, M. C., and Will, H. (1990). Recognition of a hepatitis B virus nucleocapsid T-cell epitope expressed as a fusion protein with the subunit B of *Escherichia coli* heat labile enterotoxin in attenuated salmonellae. Vaccine 8, 569-572.

Shaw, C. A., and Starnbach, M. N. (2003). Using Modified Bacterial Toxins to Deliver Vaccine Antigens. ASM News 69, 384-389.

Silva, A. J., Mohan, A., and Benitez, J. A. (2003). Cholera vaccine candidate 638: intranasal immunogenicity and expression of a foreign antigen from the pulmonary pathogen *Coccidioides immitis*. Vaccine 21, 4715-4721.

Smerdou, C., Anton, I. M., Plana, J., Curtiss, R., 3rd, and Enjuanes, L. (1996). A continuous epitope from transmissible gastroenteritis virus S protein fused to *E. coli* heat-labile toxin B subunit expressed by attenuated *Salmonella* induces serum and secretory immunity. Virus Res 41, 1-9.

Somner, E. A., Ogun, S. A., Sinha, K. A., Spencer Valero, L. M., Lee, J. J., Harrison, J. A., Holder, A. A., Hormaeche, C. E., and Khan, C. M. (1999). Expression of disulphide-bridge-dependent conformational epitopes and immunogenicity of the carboxy-terminal 19 kDa domain of *Plasmodium yoelii* merozoite surface protein-1 in live attenuated *Salmonella* vaccine strains Microbiology 145 (Pt 1) 221-229.

Sory, M. P., and Cornelis, G. R. (1990). Delivery of the cholera toxin B subunit by using a recombinant *Yersinia enterocolitica* strain as a live oral carrier. Res Microbiol 141, 921-929.

Spangrude, G. J., Sacchi, F., Hill, H. R., Van Epps, D. E., and Daynes, R. A. (1985). Inhibition of lymphocyte and neutrophil chemotaxis by *pertussis* toxin. J Immunol 135, 4135-4143.

Su, G. F., Brahmbhatt, H. N., de Lorenzo, V., Wehland, J., and Timmis, K. N. (1992). Extracellular export of Shiga toxin B-subunit/haemolysin A (C-terminus) fusion protein expressed in *Salmonella typhimurium* aroA-mutant and stimulation of B-subunit specific antibody responses in mice. Microb Pathog 13, 465-476.

Thungapathra, M., Sharma, C., Gupta, N., Ghosh, R. K., Mukhopadhyay, A., Koley, H., Nair, G. B., and Ghosh, A. (1999). Construction of a recombinant live oral vaccine from a non-toxigenic strain of *Vibrio cholerae* O1 serotype inaba biotype E1 Tor and assessment of its reactogenicity and immunogenicity in the rabbit model. Immunol Lett 68, 219-227.

Todar, K. (2002). Mechanism of bacterial pathogenicity: protein toxins. Todar's Online Textbook of Bacteriology.: http://textbookofbacteriology.net/proteintoxins.html.

Tzschaschel, B. D., Guzman, C. A., Timmis, K. N., and de Lorenzo, V. (1996a). An *Escherichia coli* hemolysin transport system-based vector for the export of polypeptides: export of Shiga-like toxin IIeB subunit by *Salmonella typhimurium* aroA. Nat Biotechnol 14, 765-769.

Tzschaschel, B. D., Klee, S. R., de Lorenzo, V., Timmis, K. N., and Guzman, C. A. (1996b). Towards a vaccine candidate against *Shigella dysenteriae* 1: expression of the Shiga toxin B-subunit in an attenuated *Shigella flexneri* aroD carrier strain. Microb Pathog 21, 277-288.

van Ginkel, F. W., Jackson, R. J., Yuki, Y., and McGhee, J. R. (2000). Cutting edge: the mucosal adjuvant cholera toxin redirects vaccine proteins into olfactory tissues. J Immunol 165, 4778-4782.

Vertiev, Y. V., Zdanovsky, A. G., Shevelev, A. B., Bonnskaya, S. A., Gening, E. L., Martin, T., Ivanov, P. A., and Yankovsky, N. K. (2001). Recombinant *Listeria* strains producing the nontoxic L-chain of *botulinum* neurotoxin A in a soluble form. Res Microbiol 152, 563-567, Walker, M. J., Rohde, M., Timmis, K. N., and Guzman, C. A. (1992). Specific lung mucosal and systemic immune responses after oral immunization of mice with *Salmonella typhimurium* aroA, *Salmonella typhi* Ty21a, and invasive *Escherichia coli* expressing recombinant *pertussis* toxin S1 subunit. Infect Immun 60, 4260-4268.

Ward, S. J., Douce, G., Figueiredo, D., Dougan, G., and Wren, B. W. (1999). Immunogenicity of a *Salmonella typhimurium* aroA aroD vaccine expressing a nontoxic domain of *Clostridium difficile* toxin A. Infect Immun 67, 2145-2152.

Wiener, M. C. (2000). Bacterial export takes its Tol. Structure 8, R171-175.

Wu, S., Beier, M., Sztein, M. B., Galen, J., Pickett, T., Holder, A. A., Gomez-Duarte, O. G., and Levine, M. M. (2000). Construction and immunogenicity in mice of attenuated *Salmonella typhi* expressing *Plasmodium falciparum* merozoite surface protein 1 (MSP-1) fused to tetanus toxin fragment C. J Biotechnol 83, 125-135.

Zheng, J. P., Zhang, Z. S., Li, S. Q., Liu, X. X., Yuan, S. L., Wang, P., Zhan, D. W., Wang, L. C., and Huang, C. F. (2005). Construction of a novel *Shigella* live-vector strain co-expressing CS3 and LTB/STm of enterotoxigenic *E. coli*. World J Gastroenterol 11, 3411-3418.

Zhu, C., Ruiz-Perez, F., Yang, Z., Mao, Y., Hackethal, V. L., Greco, K. M., Choy, W., Davis, K., Butterton, J. R., and Boedeker, E. C. (2006). Delivery of heterologous protein antigens via hemolysin or autotransporter systems by an attenuated ler mutant of rabbit enteropathogenic *Escherichia coli*. Vaccine 24, 3821-3831.

The invention claimed is:

1. A bacterium comprising the following components:
   (I) at least one polynucleotide encoding a heterologous antigenic determinant that induces a CTL response against a tumor cell;
   (II) at least one polynucleotide encoding a heterologous protein toxin or protein toxin subunit; and
   (III) (a) at least one polynucleotide encoding a transport system that expresses the products of (I) and (II) on the outer surface of the bacterium or that secretes products of (I) and (II) from the bacterium; and
   optionally, (b) at least one polynucleotide that encodes a protein that lyses the bacterium when it is inside of the cytosol of a mammalian cell thereby releasing plasmids or expression vectors contained in the lysed bacterium; and
   (IV) at least one polynucleotide that activates the expression of one or more of (I), (II) and/or (III) in the bacterium;
   wherein said bacterium is selected from the group consisting of Escherichia, Salmonella, Yersinia, Vibrio, Listeria, Shigella, Yersinia, and Pseudomonas, with the proviso that it is not Vibrio cholera; and
   wherein polynucleotides (I), (II), (III) and (IV) are different from each other and polynucleotides (I), (II) and (III) encode proteins that are different from each other.

2. The bacterium according to claim 1, wherein polynucleotide(s) (I) encodes a heterologous antigenic determinant selected from the group consisting of a receptor; extracellular, transmembranic or intracellular part of a receptor; adhesion molecule; extracellular, transmembranic or intracellular part of an adhesion molecule; signal-transducing protein; cell-cycle protein; transcription factor; differentiation protein; embryonic protein; viral protein; allergen; protein of microbial pathogen; protein of eukaryotic pathogen; cancer testis antigen protein; tumor antigen protein; and tissue-cell specific protein, wherein the tissue cell is selected from the group consisting of glandula thyroidea, glandula mammaria, glandula salivaria, nodus lymphoideus, glandula mammaria, tunica mucosa gastris, kidney, ovarium, prostate, cervix, tunica serosa vesicae urinariae, and nevus; or combinations thereof.

3. The bacterium according to claim 2, wherein polynucleotide(s) (I) encodes a heterologous antigenic determinant selected from the group consisting of the following wild-type proteins and their known mutants: Her-2/neu, androgen receptor, estrogen receptor, midkine receptor, EGF receptor, ERBB2, ERBB4, TRAIL receptor, FAS, TNF-alpha receptor, TGF-beta receptor, lactoferrin receptor, basic myelin, alpha-lactalbumin, GFAP, fibrillary acid protein, tyrosinase, EGR-1, MUC1, c-Raf (Raf-1), A-Raf, B-Raf, B-Raf V599E, B-Raf V600E, B-Raf KD, B-Raf V600E kinase domain, B-Raf V600E KD, B-Raf V600E kinase domain KD, B-Raf kinase domain, B-Raf kinase domain KD, N-Ras, K-Ras, H-Ras, Bcl-2, Bcl-X, Bcl-W, Bfl-1, Brag-1, Mcl-1, A1, Bax, BAD, Bak, Bcl-Xs, Bid, Bik, Hrk, Bcr/abl, Myb, C-Met, IAP1, IAO2, XIAP, ML-IAP LIVIN, survivin, APAF-1, cyclin D(1-3), cyclin E, cyclin A, cyclin B, cyclin H, Cdk-1, Cdk-2, Cdk-4, Cdk-6, Cdk-7, Cdc25C, p16, p15, p21, p27, p18, pRb, p107, p130, E2F(1-5), GAAD45, MDM2, PCNA, ARF, PTEN, APC, BRCA, Akt, P13K, mTOR, p53 and homologues, C-Myc, NFkB, c-Jun, ATF-2, Sp1, prostate specific antigen (PSA), carcinoembryonic antigen, alpha-fetoprotein, PAP; PSMA; STEAP; MAGE, MAGE-1, MAGE-3, NY-ESO-1, PSCA, MART, Gp100, tyrosinase, GRP, TCF-4, viral antigens of the viruses HIV, HPV, HCV, HPV, EBV, CMV, HSV, influenza virus, influenza virus type A, influenza virus type A (H5N1) and (H3N2), influenza virus type B, influenza virus type C; hemagglutinins, hemagglutinin H1, hemagglutinin H5, hemagglutinin H7, hemagglutinin HA1, hemagglutinin HA12, hemagglutinin HA12C, neuramidase, p60, LLO, urease, CSP, calflagin and/or CPB; or
   wherein polynucleotide(s) (I) encodes a heterologous antigenic determinant that is at least one complete or partial antigen of at least one wild-type or mutated protein selected from the group of kinases consisting of the following wild-type proteins and their known mutants (accession numbers in parentheses): AAK1 (NM 014911), AATK (NM 004920), ABL1 (NM 005157), ABL2 (NM 005158), ACK1 (NM 005781), ACVR1 (NM 001105), ACVR1B (NM 020328), ACVR2 (NM 001616), ACVR2B (NM 001106), ACVRL1 (NM 000020), ADCK1 (NM 020421), ADCK2 (NM 052853), ADCK4 (NM 024876), ADCK5 (NM 174922), ADRBK1 (NM 001619), ADRBK2 (NM 005160), AKT1 (NM 005163), AKT2 (NM 001626), AKT3 (NM 005465), ALK (NM 004304), ALK7 (NM 145259), ALS2CR2 (NM 018571), ALS2CR7 (NM 139158), AMHR2 (NM 020547), ANKK1 (NM 178510), ANKRD3 (NM 020639), APEG1 (NM 005876), ARAF (NM 001654), ARK5 (NM 014840), ATM (NM 000051), ATR (NM 001184), AURKA (NM 003600), AURKB (NM 004217), AURKC (NM 003160), AXL (NM 001699), BCKDK (NM 005881), BCR (NM 004327), BIKE (NM 017593), BLK (NM 001715), BMPR1A (NM 004329), BMPR1B (NM 001203), BMPR2 (NM 001204), BMX (NM 001721), BRAF (NM 004333), BRD2 (NM 005104), BRD3 (NM 007371), BRD4 (NM 014299), BRDT (NM 001726), BRSK1 (NM 032430), BRSK2 (NM 003957), BTK (NM 000061), BUB1 (NM 004336), BUB1B (NM 001211), CABC1 (NM 020247), CAMK1 (NM 003656), CaMK1b (NM 198452), CAMK1D (NM 020397), CAMK1G (NM 020439), CAMK2A (NM 015981), CAMK2B (NM 001220), CAMK2D (NM 001221), CAMK2G (NM 001222), CAMK4 (NM 001744), CAMKK1 (NM 032294), CAMKK2 (NM 006549), CASK (NM 003688), CCRK (NM 012119), CDC2 (NM 001786), CDC2L1 (NM 001787), CDC2L5 (NM 003718), CDC42BPA (NM 014826), CDC42BPB (NM 006035), CDC7L1 (NM 003503), CDK10 (NM 003674), CDK11 (NM 015076), CDK2 (NM 001798), CDK3 (NM 001258), CDK4 (NM 000075), CDK5 (NM 004935), CDK6 (NM 001259), CDK7 (NM 001799), CDK8 (NM 001260), CDK9 (NM 001261), CDKL1 (NM 004196), CDKL2 (NM 003948), CDKL3 (NM 016508), CDKL4 (NM 001009565), CDKL5 (NM 003159), CHEK1 (NM 001274), CHUK (NM 001278), CIT (NM 007174), CLK1 (NM 004071), CLK2 (NM 003993), CLK3 (NM 003992), CLK4 (NM 020666), CRK7 (NM 016507), CSF1R (NM 005211), CSK (NM 004383), CSNK1A1 (NM 001892), CSNK1D (NM 001893), CSNK1E (NM 001894), CSNK1G1 (NM 022048), CSNK1G2 (NM 001319), CSNK1G3 (NM 004384), CSNK2A1 (NM 001895), CSNK2A2 (NM 001896), DAPK1 (NM 004938), DAPK2 (NM 014326), DAPK3 (NM 001348), DCAMKL1 (NM 004734), DCAMKL2 (NM 152619), DCAMKL3 (XM 047355), DDR1 (NM 013993), DDR2 (NM 006182), DMPK (NM 004409), DMPK2 (NM 017525.1), DYRK1A (NM 001396), DYRK1B (NM 006484), DYRK2 (NM 006482), DYRK3 (NM 003582), DYRK4 (NM 003845), EEF2K (NM 013302), EGFR (NM 005228), EIF2AK3 (NM 004836), EIF2AK4 (NM_001013703), EPHA1 (NM 005232), EPHA10 (NM 001004338), EPHA2 (NM 004431), EPHA3 (NM 005233), EPHA4 (NM 004438), EPHA5 (NM 004439), EPHA6 (XM 114973), EPHA7 (NM 004440), EPHA8 (NM 020526), EPHB1 (NM 004441), EPHB2 (NM 017449), EPHB3 (NM 004443), EPHB4 (NM 004444), EPHB6 (NM 004445), ERBB2 (NM 004448), ERBB3 (NM 001982), ERBB4 (NM 005235), ERK8 (NM 139021), ERN1 (NM 001433), ERN2 (NM 033266), FASTK (NM 025096), FER (NM 005246), FES (NM 002005), FGFR1 (NM 000604), FGFR2 (NM 022970), FGFR3 (NM 000142), FGFR4 (NM 022963), FGR (NM 005248), FLJ23074 (NM 025052), FLJ23119 (NM 024652), FLJ23356 (NM 032237), FLT1 (NM 002019), FLT3 (NM 004119), FLT4 (NM 002020), FRAP1 (NM 004958), FRK (NM 002031), FYN (NM 002037), GAK (NM 005255), GPRK5 (NM 005308), GPRK6 (NM 002082), GPRK7 (NM 139209), GRK4 (NM 005307), GSG2 (NM 031965), GSK3A (NM 019884), GSK3B (NM 002093), GUCY2C (NM 004963), GUCY2D (NM 000180), GUCY2F (NM 001522), H11 (NM 014365), HAK (NM 052947), HCK (NM 002110), HIPK1 (NM 152696), HIPK2 (NM 022740), HIPK3 (NM 005734), HIPK4 (NM 144685), HRI (NM 014413), HUNK (NM 014586), ICK (NM 016513), IGF1R (NM 000875), IKBKB (NM 001556), IKBKE (NM 014002), ILK (NM 004517), INSR (NM 000208), INSRR (NM 014215), IRAK1 (NM 001569), IRAK2 (NM 001570), IRAK3 (NM 007199), IRAK4 (NM 016123), ITK (NM 005546), JAK1 (NM 002227), JAK2 (NM 004972), JAK3 (NM 000215), KDR (NM 002253), KIS (NM 144624), KIT (NM 000222), KSR (XM 290793), KSR2 (NM 173598), LAK (NM 025144), LATS1 (NM 004690), LATS2 (NM 014572), LCK (NM 005356), LIMK1 (NM 016735), LIMK2 (NM 005569), LMR3 (XM 055866), LMTK2 (NM 014916), LOC149420 (NM 152835), LOC51086 (NM 015978), LRRK2 (XM 058513), LTK (NM 002344), LYN (NM 002350), MAK (NM 005906), MAP2K1 (NM 002755), MAP2K2 (NM 030662), MAP2K3 (NM 002756), MAP2K4 (NM 003010), MAP2K5 (NM 002757), MAP2K6 (NM 002758), MAP2K7 (NM 005043), MAP3K1 (XM 042066), MAP3K10 (NM 002446), MAP3K11 (NM 002419), MAP3K12 (NM 006301), MAP3K13 (NM 004721), MAP3K14 (NM 003954), MAP3K2 (NM 006609), MAP3K3 (NM 002401), MAP3K4 (NM 005922), MAP3K5 (NM 005923), MAP3K6 (NM 004672), MAP3K7 (NM 003188), MAP3K8 (NM 005204), MAP3K9 (NM 033141), MAP4K1 (NM 007181), MAP4K2 (NM 004579), MAP4K3 (NM 003618), MAP4K4 (NM 145686), MAP4K5 (NM 006575), MAPK1 (NM 002745), MAPK10 (NM 002753), MAPK11 (NM 002751), MAPK12 (NM 002969), MAPK13 (NM 002754), MAPK14 (NM 001315), MAPK3 (NM 002746), MAPK4 (NM 002747), MAPK6 (NM 002748), MAPK7 (NM 002749), MAPK8 (NM 002750), MAPK9 (NM 002752), MAPKAPK2 (NM 032960), MAPKAPK3 (NM 004635), MAPKAPK5 (NM 003668), MARK (NM 018650), MARK2 (NM 017490), MARK3 (NM 002376), MARK4 (NM 031417), MAST1 (NM 014975), MAST205 (NM 015112), MAST3 (XM 038150), MAST4 (XM 291141), MASTL (NM 032844), MATK (NM 139355), MELK (NM 014791), MERTK (NM 006343), MET (NM 000245), MGC33182 (NM 145203), MGC42105 (NM 153361), MGC43306 (C9orf96), MGC8407 (NM 024046), MIDORI (NM 020778), MINK (NM 015716), MKNK1 (NM 003684), MKNK2 (NM 017572), MLCK (NM 182493), MLK4 (NM 032435), MLKL (NM 152649), MOS (NM 005372), MST1R (NM 002447), MST4 (NM 016542), MUSK (NM 005592), MYLK (NM 053025), MYLK2 (NM 033118), MYO3A (NM 017433), MYO3B (NM 138995), NEK1 (NM 012224), NEK10 (NM 152534), NEK11 (NM 024800), NEK2 (NM 002497), NEK3 (NM 002498), NEK4 (NM 003157), NEK5 (MGC75495), NEK6 (NM 014397), NEK7 (NM 133494), NEK8 (NM 178170), NEK9 (NM 033116), NLK (NM 016231), NPR1 (NM 000906), NPR2 (NM 003995), NRBP (NM 013392), NRBP2 (NM 178564), NRK (NM 198465), NTRK1 (NM 002529), NTRK2 (NM 006180), NTRK3 (NM 002530), OBSCN (NM 052843), OSR1 (NM 005109), PACE-1 (NM 020423), PAK1 (NM 002576), PAK2 (NM 002577), PAK3 (NM 002578), PAK4 (NM 005884), PAK6 (NM 020168), PAK7 (NM 020341), PASK (NM 015148), PCTK1 (NM 006201), PCTK2 (NM 002595), PCTK3 (NM 212503), PDGFRA (NM 006206), PDGFRB (NM 002609), PDK1 (NM 002610), PDK2 (NM 002611), PDK3 (NM 005391), PDK4 (NM 002612), PDPK1 (NM 002613), PFTK1 (NM 012395), PHKG1 (NM 006213), PHKG2 (NM 000294), PIK3R4 (NM 014602), PIM1 (NM 002648), PIM2 (NM 006875), PIM3 (NM 001001852), PINK1 (NM 032409), PKE (NM 173575), PKMYT1 (NM 004203), pknbeta (NM 013355), PLK (NM 005030), PLK3 (NM 004073), PRKAA1 (NM 006251), PRKAA2 (NM 006252), PRKACA (NM 002730), PRKACB (NM 002731), PRKACG (NM 002732), PRKCA (NM 002737), PRKCB1 (NM 002738), PRKCD (NM 006254), PRKCE (NM 005400), PRKCG (NM 002739), PRKCH (NM 006255), PRKCI (NM 002740), PRKCL1 (NM 002741), PRKCL2 (NM 006256), PRKCM (NM 002742), PRKCN (NM 005813), PRKCQ (NM 006257), PRKCZ (NM 002744), PRKD2 (NM 016457), PRKDC (NM 006904), PRKG1 (NM 006258), PRKG2 (NM 006259), PRKR (NM 002759), PRKWNK1 (NM 018979), PRKWNK2 (NM 006648), PRKWNK3 (NM 020922), PRKWNK4 (NM 032387), PRKX (NM 005044), PRKY (NM 002760), PRPF4B (NM 003913), PSKH1 (NM 006742), PSKH2 (NM 033126), PTK2 (NM 005607), PTK2B (NM 004103), PTK6 (NM 005975), PTK7 (NM 002821), PTK9 (NM 002822), PTK9L (NM 007284), PXK (NM 017771), QSK (NM 025164), RAD53 (NM 007194), RAF1 (NM 002880), RAGE (NM 014226), RET (NM 020975), RHOK (NM 002929), RIOK1 (NM 031480), RIOK2 (NM 018343), RIPK1 (NM 003804), RIPK2 (NM 003821), RIPK3 (NM 006871), RIPK5 (NM 015375), RNASEL (NM 021133), ROCK1 (NM 005406), ROCK2 (NM 004850), ROR1 (NM 005012), ROR2 (NM 004560), ROS1 (NM 002944), RPS6KA1 (NM 002953), RPS6KA2 (NM 021135), RPS6KA3 (NM 004586), RPS6KA4 (NM 003942), RPS6KA5 (NM 004755), RPS6KA6 (NM 014496), RPS6KB1 (NM 003161), RPS6KB2 (NM 003952), RPS6KC1 (NM 012424), RPS6KL1 (NM 031464), RYK (NM 002958), SBK (XM 370948), SCYL1 (NM 020680), SCYL2 (NM 017988), SGK (NM 005627), SgK069 (SU SgK069), SgK085 (XM 373109), SgK110 (SU SgK110), SGK2 (NM 016276), SgK223 (XM 291277), SgK269 (XM 370878), SgK424 (CGP SgK424), SgK493 (SU_SgK493), SgK494 (NM 144610), SgK495 (NM 032017), SGKL (NM 013257), SK681 (NM 001001671), SLK (NM 014720), SMG1 (NM 015092), SNARK (NM 030952), SNF1LK (NM 173354), SNF1LK2 (NM 015191), SNK (NM 006622), SNRK (NM 017719), SRC (NM 005417), SRMS (NM 080823), SRPK1 (NM 003137), SRPK2 (NM 003138), SSTK (NM 032037), STK10 (NM 005990), STK11 (NM 000455), STK16 (NM 003691), STK17A (NM 004760), STK17B (NM 004226), STK18 (NM 014264), STK19 (NM 032454), STK22B (NM 053006), STK22C (NM 052841), STK22D (NM 032028), STK23 (NM 014370), STK24 (NM 003576), STK25 (NM 006374), STK3 (NM 006281), STK31 (NM 031414), STK32B (NM 018401), STK33 (NM 030906), STK35 (NM 080836), STK36 (NM 015690), STK38 (NM 007271), STK38L (NM 015000), STK39 (NM 013233), STK4 (NM 006282), STLK5 (NM 001003787), STYK1 (NM 018423), SUDD (NM 003831), SYK (NM 003177), TAF1 (NM 138923), TAF1L (NM 153809), TAO1 (NM 004783), TAOK1 (NM 020791), TAOK3 (NM 016281), TBCK (NM 033115), TBK1 (NM 013254), TEC (NM 003215), TEK (NM 000459), TESK1 (NM 006285), TESK2 (NM 007170), TEX14 (NM 031272), TGFBR1 (NM 004612), TGFBR2 (NM 003242), TIE (NM 005424), TIF1 (NM 003852), TLK1 (NM 012290), TLK2 (NM 006852), TNIK (NM 015028), TNK1 (NM 003985), TOPK (NM 018492), TP53RK (NM 033550), TRAD (NM 007064), TRIB1 (NM 025195), TRIB2 (NM 021643), TRIB3 (NM 021158), TRIM28 (NM 005762), TRIM33 (NM 015906), TRIO (NM 007118), TRPM6 (NM 017662), TRPM7 (NM 017672), TRRAP (NM 003496), TSSK4 (NM 174944), TTBK1 (NM 032538), TTBK2 (NM 173500), TTK (NM 003318), TTN (NM 003319), TXK (NM 003328), TYK2 (NM 003331), TYRO3 (NM 006293), ULK1 (NM 003565), ULK2 (NM 014683), ULK3 (NM 015518), ULK4 (NM 017886), VRK1 (NM 003384), VRK2 (NM 006296), VRK3 (NM 016440), WEE1 (NM 003390), Wee1B (NM 173677), YANK1 (NM 145001), YES1 (NM 005433), ZAK (NM 016653), and ZAP70 (NM 001079); or combinations thereof.

4. The bacterium according to claim 1, which expresses polynucleotide (II) selected from the group consisting of a bacterial toxin, enterotoxin, exotoxin, type I toxin, type II toxin, type III toxin, type IV toxin, type V toxin, RTX toxin, AB toxin, A-B toxin, A/B toxin, A+B toxin, A-5B toxin and AB5 toxin; or combinations thereof.

5. The bacterium according to claim 4, wherein polynucleotide(s) (II) encodes a heterologous protein toxin or protein toxin subunit selected from the group consisting of Adenylate cyclase toxin, Anthrax toxin, Anthrax toxin (EF), Anthrax toxin (LF), *Botulinum* toxin, Cholera toxin (CT, Ctx), Cholera toxin subunit B (CTB, CtxB), Diphtheria toxin (DT, Dtx), *E. coli* LT toxin, *E. coli* heat labile enterotoxin (LT), *E. coli* heat labile enterotoxin subunit B (LTB), *E. coli* ST toxin, *E. coli* heat stabile enterotoxin (ST), Erythrogenic toxin, Exfoliatin toxin, Exotoxin A, *Perfringens* enterotoxin, *Pertussis* toxin (PT, Ptx), Shiga toxin (ST, Stx), Shiga toxin subunit B (STB, StxB), Shiga-like toxin, *Staphylococcus* enterotoxins, Tetanus toxin (TT), Toxic shock syndrome toxin (TSST-1), Vero toxin (VT), Toxin A (TA) and Toxin B (TB) of *Clostridium difficile*, Lethal Toxin (LT) and Hemorrhagic Toxin (HT) of *Clostridium sordellii*, and alpha Toxin (AT) of *Clostridium novyi*; or combinations thereof.

6. The bacterium according to claim 1, wherein polynucleotides (I) and (II) are linked together to enable the expression and/or secretion of a fusion protein encoded by both polynucleotides.

7. The bacterium according to claim 6, which expresses a fusion protein selected from the group consisting of CtxB-PSA, CtxB-B-Raf V600E KD, CtxB-B-Raf V600E kinase domain, CtxB-B-Raf V600E kinase domain KD, CtxB-B-Raf, CtxB-B-Raf KD, CtxB B-Raf kinase domain KD, CtxB-HA1, and CtxB-HA12C; or combinations thereof.

8. The bacterium according to claim 1, which expresses a polynucleotide(s) (III) a) selected from the group consisting of type I secretion system, type II secretion system, type III secretion system, type IV secretion system, type V secretion system, hemolysin transport system (signal) of *Escherichia coli* (nucleotide sequences containing HlyA, HlyB and HlyD under the control of the hly-specific promoter), hemolysin transport system (signal) of *Escherichia coli* (nucleotide sequences containing HlyA, HlyB and HlyD under the control of a not hly-specific bacterial promoter), transport signal for the S-layer (Rsa A) protein of *Caulobacter crescentus*, transport signal for the TolC protein of *Escherichia coli*, secretion signal Vtgss and/or secretion signals derived from listeriolysin, p60 and/or ActA and wherein component (III) b) is selected from the group consisting of endolysins, lytic protein of gram-positive bacteria, lytic protein of *Listeria monocytogenes*, PLY551 of *Listeria monocytogenes*, and holin of *Listeria Monocytogenes*; or combinations thereof.

9. The bacterium according to claim 8, wherein polynucleotide(s) (III) a) is at least one nucleotide sequence coding for only one transport system, which enables the concomitant expression of the expression products of polynucleotides (I) and II) on the outer surface of the microorganism and/or enables the concomitant secretion of the expression products of polynucleotides (I) and (II), wherein such polynucleotide(s) (III) a) is at least one nucleotide sequence coding for the hemolysin transport system (signal) of *Escherichia coli* (nucleotide sequences containing HlyA, HlyB and HlyD under the control of the hly-specific promoter) or the hemolysin transport system (signal) of *Escherichia coli* (nucleotide sequences containing HlyA, HlyB and HlyD under the control of a not hly-specific bacterial promoter).

10. The bacterium according to claim 1, which expresses polynucleotide(s) (III) a) where the expression products of polynucleotides (I) and (II) are secreted.

11. The bacterium according to claim 1, wherein
polynucleotide(s) (I) is selected from the group consisting of B-Raf V600E, B-Raf V600E kinase domain, B-Raf V600E KD, B-Raf V600E kinase domain KD, B-Raf KD, B-Raf kinase domain, B-Raf kinase domain KD, prostate specific antigen (PSA), hemagglutinin HA1 hemagglutinin HA12, and hemagglutinin HA12C;

polynucleotide(s) (II) is selected from the group consisting of Cholera toxin subunit B (CTB, CtxB), *E. coli* heat-labile enterotoxin subunit B (LTB), and tetanus toxin (TT);

polynucleotide(s) (III) a) is an HlyA hemolysin transport signal of *Escherichia coli* together with component(s) of the Hly secretion system (nucleotide sequences containing HlyA, HlyB and HlyD under the control of the hly-specific promoter);

polynucleotide (IV) is an endogenous promoter of the *E. coli* hly locus;

wherein polynucleotides (I) and (II) are linked together to enable the expression of a fusion protein encoded by both polynucleotide sequences and wherein the fusion protein is secreted.

12. A pharmaceutical composition comprising at least one bacterium according to claim 1, and a pharmaceutically acceptable carrier, diluent, or excipient.

13. The pharmaceutical composition of claim 12 that has been lyophilized.

14. A method for inducing an antigen-specific immune response comprising administering treating a disease or disorder, comprising administering to a subject in need thereof an effective amount of the bacterium of claim 1.

15. The method of claim 14, comprising inducing an antigen-specific immune response to treat a disease or disorder selected from the group consisting of uncontrolled cell division, malignant tumors, benign tumors, solid tumors, sarcomas, carcinomas, hyperproliferative disorders, carcinoids, Ewing sarcomas, Kaposi sarcomas, brain tumors, tumors originating from the brain and/or the nervous system and/or the meninges, gliomas, neuroblastomas, stomach cancer, kidney cancer, kidney cell carcinomas, prostate cancer, prostate carcinomas, connective tissue tumors, soft tissue sarcomas, pancreas tumors, liver tumors, head tumors, neck tumors, oesophageal cancer, thyroid cancer, osteosarcomas, retinoblastomas, thymoma, testicular cancer, lung cancer, bronchial carcinomas, breast cancer, mamma carcinomas, intestinal cancer, colorectal tumors, colon carcinomas, rectum carcinomas, gynecological tumors, ovary tumors/ovarian tumors, uterine cancer, cervical cancer, cervix carcinomas, cancer of body of uterus, corpus carcinomas, endometrial carcinomas, urinary bladder cancer, bladder cancer, skin cancer, basaliomas, spinaliomas, melanomas, intraocular melanomas, leukemia, chronic leukemia, acute leukemia, lymphomas, infection, viral or bacterial infection, influenza, chronic inflammation, organ rejection, and autoimmune diseases.

16. A plasmid or expression vector comprising polynucleotides (I) to (IV) according to claim 1 or a combination of plasmids and/or expression vectors that together comprise polynucleotides (I) to (IV).

17. A process for the production of a bacterium according to claim 1, comprising transforming a bacterium with the plasmid(s) or expression vector(s) of claim 16.

18. The bacterium of claim 1 that induces an antigen-specific $CD8^+$ cellular immune response against the heterologous antigenic determinant (I) when administered to a subject in need thereof.

19. A method for inducing an antigen-specific $CD8^+$ cellular immune response comprising administering the bacterium according to claim 1 to a subject in need thereof.

20. A bacterium comprising one or more polynucleotides that encode at least one heterologous cellular antigenic determinant of a mammalian tumor cell, a heterologous protein toxin or protein toxin subunit, and a transport system that transports the heterologous cellular antigenic determinant and heterologous protein toxin or protein toxin subunit to the outer surface of the bacterium or that secretes them from the bacterium;

wherein said bacterium is selected from the group consisting of *Escherichia, Salmonella, Yersinia, Vibrio, Listeria, Shigella, Yersinia*, and *Pseudomonas*, with the proviso that it is not *Vibrio cholera*.

21. The bacterium of claim 20, further comprising at least one heterologous nucleotide sequence that activates the expression of one or more of components (I), (II) and/or (III) in the bacterium.

22. The bacterium of claim 20, further comprising at least one heterologous nucleotide sequence that encodes a protein that lyses the recombinant bacterium when it is inside of the cytosol of a mammalian cell thereby releasing plasmids or expression vectors contained in the lysed bacterium.

23. The bacterium of claim 20 that comprises one or more heterologous polynucleotides that encode a cellular antigenic determinant of prostate specific antigen (PSA), a protein toxin or protein toxin subunit comprising cholera toxin B (CTB) and a transport system comprising HlyA, HlyB and HlyD.

24. A vaccine comprising a live bacterium according to claim 20 and one or more pharmaceutically acceptable excipients or carriers.

* * * * *

SEQUENCE LISTING

```
<160> NUMBER OF SEQ ID NOS: 40

<210> SEQ ID NO 1
<211> LENGTH: 61
<212> TYPE: DNA
<213> ORGANISM: artificial
<220> FEATURE:
<223> OTHER INFORMATION: synthetic DNA

<400> SEQUENCE: 1
gagtattcaa catttccgtg tcgcccttat tccctttttt ggtgtaggct ggagctgctt    60
c                                                                    61

<210> SEQ ID NO 2
<211> LENGTH: 60
<212> TYPE: DNA
<213> ORGANISM: artificial
<220> FEATURE:
<223> OTHER INFORMATION: synthetic DNA

<400> SEQUENCE: 2
gcgatctgtc tatttcgttc atccatagtt gcctgactcc ccatatgaat atcctcctta    60

<210> SEQ ID NO 3
<211> LENGTH: 21
<212> TYPE: DNA
<213> ORGANISM: artificial
<220> FEATURE:
<223> OTHER INFORMATION: synthetic DNA

<400> SEQUENCE: 3
gattggtgat gcatccctca t                                              21

<210> SEQ ID NO 4
<211> LENGTH: 21
<212> TYPE: DNA
<213> ORGANISM: artificial
<220> FEATURE:
<223> OTHER INFORMATION: synthetic DNA

<400> SEQUENCE: 4
ggtgctcatg cattggccac g                                              21

<210> SEQ ID NO 5
<211> LENGTH: 37
<212> TYPE: DNA
<213> ORGANISM: artificial
<220> FEATURE:
<223> OTHER INFORMATION: synthetic DNA

<400> SEQUENCE: 5
aaaaaagtcg acggctgtgc aggtcgtaaa tcactgc                             37

<210> SEQ ID NO 6
<211> LENGTH: 39
<212> TYPE: DNA
<213> ORGANISM: artificial
<220> FEATURE:
<223> OTHER INFORMATION: synthetic DNA

<400> SEQUENCE: 6
```

```
aaaaaagcgg ccgcgaaatt gttatccgct cacaattcc                    39
```

<210> SEQ ID NO 7
<211> LENGTH: 46
<212> TYPE: DNA
<213> ORGANISM: artificial
<220> FEATURE:
<223> OTHER INFORMATION: synthetic DNA

<400> SEQUENCE: 7

```
aaaaaagcgg ccgctaagga tgaattatga ttaaattaaa atttgg             46
```

<210> SEQ ID NO 8
<211> LENGTH: 42
<212> TYPE: DNA
<213> ORGANISM: artificial
<220> FEATURE:
<223> OTHER INFORMATION: synthetic DNA

<400> SEQUENCE: 8

```
tttatagtcg acttaatttg ccatactaat tgcggcaatc gc                 42
```

<210> SEQ ID NO 9
<211> LENGTH: 36
<212> TYPE: DNA
<213> ORGANISM: artificial
<220> FEATURE:
<223> OTHER INFORMATION: synthetic DNA

<400> SEQUENCE: 9

```
gcatatgcac atgcatcacc tcaaaatatt actgat                        36
```

<210> SEQ ID NO 10
<211> LENGTH: 44
<212> TYPE: DNA
<213> ORGANISM: artificial
<220> FEATURE:
<223> OTHER INFORMATION: synthetic DNA

<400> SEQUENCE: 10

```
ggcttttta tatcttatgc atgcccgggc attgcggcaa tcgc                44
```

<210> SEQ ID NO 11
<211> LENGTH: 18
<212> TYPE: DNA
<213> ORGANISM: artificial
<220> FEATURE:
<223> OTHER INFORMATION: synthetic DNA

<400> SEQUENCE: 11

```
gtgggaggct gggagtgc                                            18
```

<210> SEQ ID NO 12
<211> LENGTH: 18
<212> TYPE: DNA
<213> ORGANISM: artificial
<220> FEATURE:
<223> OTHER INFORMATION: synthetic DNA

<400> SEQUENCE: 12

```
ggggttggcc acgatggt                                            18
```

<210> SEQ ID NO 13
<211> LENGTH: 29
<212> TYPE: DNA
<213> ORGANISM: artificial

```
<220> FEATURE:
<223> OTHER INFORMATION: synthetic DNA

<400> SEQUENCE: 13
catgtatgca ttagccatgg tatacctgg                                              29

<210> SEQ ID NO 14
<211> LENGTH: 33
<212> TYPE: DNA
<213> ORGANISM: artificial
<220> FEATURE:
<223> OTHER INFORMATION: synthetic DNA

<400> SEQUENCE: 14 tttttttatgc ataagggaaa caccacatct gcc                                        33

<210> SEQ ID NO 15
<211> LENGTH: 18
<212> TYPE: DNA
<213> ORGANISM: artificial
<220> FEATURE:
<223> OTHER INFORMATION: synthetic DNA

<400> SEQUENCE: 15
gccatcatgt cagctcta                                                          18

<210> SEQ ID NO 16
<211> LENGTH: 18
<212> TYPE: DNA
<213> ORGANISM: artificial
<220> FEATURE:
<223> OTHER INFORMATION: synthetic DNA

<400> SEQUENCE: 16
aggggaaaca catctgcc                                                          18

<210> SEQ ID NO 17
<211> LENGTH: 18
<212> TYPE: DNA
<213> ORGANISM: artificial
<220> FEATURE:
<223> OTHER INFORMATION: synthetic DNA

<400> SEQUENCE: 17
atctgtcaaa tggagaaa                                                          18

<210> SEQ ID NO 18
<211> LENGTH: 21
<212> TYPE: DNA
<213> ORGANISM: artificial
<220> FEATURE:
<223> OTHER INFORMATION: synthetic DNA

<400> SEQUENCE: 18
tactccactt atttcctctc t                                                      21

<210> SEQ ID NO 19
<211> LENGTH: 87
<212> TYPE: DNA
<213> ORGANISM: artificial
<220> FEATURE:
<223> OTHER INFORMATION: synthetic DNA

<400> SEQUENCE: 19
ctgaattcat gaaatatca tcatttattt ctacatcact gccccctgccg gcatcagtgt            60 caaataaagt aaaatgttat gttttat                                                87
```

```
<210> SEQ ID NO 20
<211> LENGTH: 32
<212> TYPE: DNA
<213> ORGANISM: artificial
<220> FEATURE:
<223> OTHER INFORMATION: synthetic DNA

<400> SEQUENCE: 20
gttttccata ctgattgccg caattgaatt gg                              32

<210> SEQ ID NO 21
<211> LENGTH: 21
<212> TYPE: DNA
<213> ORGANISM: artificial
<220> FEATURE:
<223> OTHER INFORMATION: synthetic DNA

<400> SEQUENCE: 21
gtgggaggct gggagtgcga g                                          21

<210> SEQ ID NO 22
<211> LENGTH: 32
<212> TYPE: DNA
<213> ORGANISM: artificial
<220> FEATURE:
<223> OTHER INFORMATION: synthetic DNA

<400> SEQUENCE: 22
cctgaattct tagacgtgat accttgaagc ac                              32

<210> SEQ ID NO 23
<211> LENGTH: 23
<212> TYPE: DNA
<213> ORGANISM: artificial
<220> FEATURE:
<223> OTHER INFORMATION: synthetic DNA

<400> SEQUENCE: 23
taaaaatctg gattgttggg ttg                                        23

<210> SEQ ID NO 24
<211> LENGTH: 23
<212> TYPE: DNA
<213> ORGANISM: artificial
<220> FEATURE:
<223> OTHER INFORMATION: synthetic DNA

<400> SEQUENCE: 24
atcatttgtc catccttcat ctg                                        23

<210> SEQ ID NO 25
<211> LENGTH: 19
<212> TYPE: DNA
<213> ORGANISM: artificial
<220> FEATURE:
<223> OTHER INFORMATION: synthetic DNA

<400> SEQUENCE: 25
gattgggaga ttcctgatg                                             19

<210> SEQ ID NO 26
<211> LENGTH: 21
<212> TYPE: DNA
<213> ORGANISM: artificial
<220> FEATURE:
<223> OTHER INFORMATION: synthetic DNA
```

```
<400> SEQUENCE: 26
cccgtggaca ggaaacgcac c                                              21

<210> SEQ ID NO 27
<211> LENGTH: 33
<212> TYPE: DNA
<213> ORGANISM: artificial
<220> FEATURE:
<223> OTHER INFORMATION: synthetic DNA

<400> SEQUENCE: 27
atcggatcct caaaatatta ctgatttgtg tgc                                 33

<210> SEQ ID NO 28
<211> LENGTH: 36
<212> TYPE: DNA
<213> ORGANISM: artificial
<220> FEATURE:
<223> OTHER INFORMATION: synthetic DNA

<400> SEQUENCE: 28
tagggatcct tagtggacag gaaacgcacc atatcc                              36

<210> SEQ ID NO 29
<211> LENGTH: 285
<212> TYPE: DNA
<213> ORGANISM: artificial
<220> FEATURE:
<223> OTHER INFORMATION: synthetic DNA

<400> SEQUENCE: 29
atgccaacaa taaccactgc acaaattaaa agcacactgc agtctgcaaa gcaatccgct    60
gcaaataaat tgcactcagc aggacaaagc acgaaagatg cattagccta tggaagtcag   120
ggtgatctta atccattaat taatgaaatc agcaaaatca tttcagctgc aggtagcttc   180
gatgttaaag aggaaagaac tgcagcttct ttattgcagt tgtccggtaa tgccagtgat   240
ttttcatatg gacggaactc aataaccctg accacatcag cataa                  285

<210> SEQ ID NO 30
<211> LENGTH: 2124
<212> TYPE: DNA
<213> ORGANISM: artificial
<220> FEATURE:
<223> OTHER INFORMATION: synthetic DNA

<400> SEQUENCE: 30
atggattctt gtcataaaat tgattatggg ttatacgccc tggagatttt agcccaatac    60
cataacgtct ctgttaaccc ggaagaaatt aaacatagat tgatacaga cgggacaggt   120 ctgggattaa cgtcatggtt gcttgctgcg aaatctttag aactaaaggt aaaacaggta   180
aaaaaaacaa ttgatcgatt aaactttatt tttctgcccg cattagtctg gagagaggat   240
ggacgtcatt ttattctgac taaaatcagc aaagaagtaa acagatatct tattttttgat   300 ttggagcagc gaaatcccg tgttctcgaa cagtctgagt tgaggcgtt atatcagggg   360 catattattc ttattacttc ccgttcttct gttaccggga actggcaaa atttgacttt   420 acctggttta ttcctgccat tataaaatac aggagaatat ttattgaaac ccttgttgta   480
tctgtttttt tacaattatt tgcattaata accccccttt tttttcaggt ggttatggac   540
aaagtattag tgcacagggg gttttcaacc cttaatgtta ttactgttgc cttatctgtt   600
gtagtggtgt ttgagattat actcagcggt ttaagaactt acattttgtc acatagtaca   660
```

```
agtcggattg atgttgagtt gggtgccaaa ctcttccggc atttactggc gctaccgatc      720
tcttattttg agagtcgtcg tgttggtgat actgttgcga gggtaagaga attagaccag      780
atccgtaatt ttctgacagg acaggcatta acatctgttt tggacttatt attttcactc      840
atattttttg cggtaatgtg gtattacagc ccaaagctta ctctggtgat cttattttcg      900
ctgccttgtt atgctgcatg gtctgttttt attagcccca ttttgcgacg tcgccttgat      960
gataagtttt cacggaatgc ggataatcaa tctttcctgg tggaatcagt aacggcgatt     1020
aacactataa agctatggc agtctcacct cagatgacga acatatggga caaacaattg     1080
gcaggatatg ttgctgcagg ctttaaagtg acagtattag caaccattgg tcaacaagga     1140
atacagttaa tacaaaagac tgttatgatc atcaacctat ggttgggagc acacctggtt     1200
atttccgggg atttaagtat tggtcagtta attgctttta atatgcttgc tggtcagatt     1260
gttgcaccgg ttattcgcct tgcacaaatc tggcaggatt ccagcaggt tggtatatca     1320 gttacccgcc ttggtgatgt gcttaactct ccaactgaaa gttatcatgg gaaactgaca     1380
ttgccggaaa ttaatggtga tatcactttt cgtaatatcc ggtttcgcta taaacctgat     1440
tctccggtta ttttggacaa tatcaatctt agtattaagc aggggaggt tattggtatt     1500 gtcggacgtt ctggttcagg aaaaagcaca ttaactaaat taattcaacg ttttatatt     1560 cctgaaaatg ccaggtatt aattgatgga catgatcttg cgttggccga tcctaactgg     1620
ttacgtcgtc aggtgggggt tgtgttgcag acaatgtgc tgcttaatcg cagtattatt     1680
gataatattt cactggctaa tcctggcatg tccgtcgaaa aagttattta tgcagcgaaa     1740
ttagcaggtg ctcatgattt tatttctgaa ttgcgtgagg ggtataacac cattgtcggg     1800
gaacaggggg caggattatc cggaggtcaa cgtcaacgca tcgcaattgc aagggcgctg     1860
gtgaacaacc ctaaaatact catttttgat gaagcaacca gtgctctgga ttatgagtcg     1920
gagcatgtca tcatgcgcaa tatgcacaaa atatgtaagg gcagaacggt tataatcatt     1980
gctcatcgtc tgtctacagt aaaaaatgca gaccgcatta ttgtcatgga aaagggaaa     2040 attgttgaac agggtaaaca taaggagctg ctttctgaac cggaaagttt atacagttac     2100
ttatatcagt tacagtcaga ctaa                                             2124
```

<210> SEQ ID NO 31
<211> LENGTH: 1437
<212> TYPE: DNA
<213> ORGANISM: artificial
<220> FEATURE:
<223> OTHER INFORMATION: synthetic DNA

<400> SEQUENCE: 31

```
atgaaaacat ggttaatggg gttcagcgag ttcctgttgc gctataaact tgtctggagt       60
gaaacatgga aaatccggaa gcaattagat actccggtac gtgaaaagga cgaaaatgaa      120
ttcttacccg ctcatctgga attaattgaa acgccagtat ccagacggcc gcgtctggtt      180
gcttatttta ttatgggggtt tctggttatt gcttttattt tatctgtttt aggccaagtg      240
gaaattgttg ccactgcaaa tgggaaatta acacacagtg ggcgtagtaa agaaattaaa      300
cctattgaaa actcaatagt taagaaaatt atcgtaaaag aaggagagtc agtccggaaa      360
ggggatgtgt tattaaagct tacagcactg ggagctgaag ctgatacgtt aaaaacacag      420
tcatcactgt tacaggccag gctggaacaa actcggtatc aaattctgag caggtcaatt      480
gaattaaata aactacctga actaaagctt cctgatgagc cttattttca gaatgtatct      540
gaagaggaag tactgcgttt aacttctttg ataaaagaac agttttccac atggcaaaat      600
```

```
cagaagtatc aaaaagaact gaatttggat aagaaaagag cagagcgatt aacagtactt      660
gcccgtataa accgttatga aaatttatca agggttgaaa aaagccgtct ggatgatttc      720
agtagtttat tgcataaaca ggcaattgca aaacatgctg tacttgagca ggagaataaa      780
tatgtcgaag cagtaaatga attacgagtt tataaatcac aactggagca aattgagagt      840
gagatattgt ctgcaaaaga agaatatcag cttgttacgc agcttttaa aaatgaaatt       900 ttagataagc taagacaaac cacagacaac attgggttat taactctgga attagcgaaa      960
aatgaagagc gtcaacaggc ttcagtaatc agggccccag tttcggtaaa agttcagcaa     1020
ctgaaggttc atactgaagg tggggttgtt acaacagcgg aaacactgat ggtcatcgtt     1080
ccggaagatg acacgctgga ggttactgct ctggtacaaa ataaagatat tggttttatt     1140
aacgtcgggc agaatgccat cattaaagtg gaggcatttc cttatacacg atatggttat     1200
ctggtgggta aggtgaaaaa tataaattta gatgcaatag aagaccagag actgggactt     1260 gttttaatg ttattattc tattgaagag aattgtttgt caaccggaaa taaaaacatt       1320
ccattaagct cgggtatggc agtcactgca gaaataaaga caggtatgcg aagtgtaatc     1380
agttatcttc ttagtccttt agaagagtca gtaacagaaa gtttacgtga gcgttaa       1437

<210> SEQ ID NO 32
<211> LENGTH: 708
<212> TYPE: DNA
<213> ORGANISM: artificial
<220> FEATURE:
<223> OTHER INFORMATION: synthetic DNA

<400> SEQUENCE: 32
gtgggaggct gggagtgcga gaagcattcc caaccctggc aggtgcttgt ggcctctcgt       60
ggcagggcag tctgcggcgg tgttctggtg caccccagt gggtcctcac agctgcccac      120
tgcatcagga acaaaagcgt gatcttgctg ggtcggcaca gcctgtttca tcctgaagac      180
acaggccagg tatttcaggt cagccacagc ttcccacacc cgctctacga tatgagcctc      240
ctgaagaatc gattcctcag gccaggtgat gactccagcc acgacctcat gctgctccgc      300
ctgtcagagc ctgccgagct cacggatgct gtgaaggtca tggacctgcc cacccaggag      360
ccagcactgg ggaccacctg ctacgcctca ggctggggca gcattgaacc agaggagttc      420 ttgacccaa agaaacttca gtgtgtggac ctccatgtta tttccaatga cgtgtgtgcg       480
caagttcacc ctcagaaggt gaccaagttc atgctgtgtg ctggacgctg acagggggc       540 aaaagcacct gctcgggtga ttctgggggc ccacttgtct gtaatggtgt gcttcaaggt      600
atcacgtcat ggggcagtga accatgtgcc ctgcccgaaa ggccttccct gtacaccaag      660
gtggtgcatt accggaagtg gatcaaggac accatcgtgg ccaacccc                    708

<210> SEQ ID NO 33
<211> LENGTH: 291
<212> TYPE: DNA
<213> ORGANISM: artificial
<220> FEATURE:
<223> OTHER INFORMATION: synthetic DNA

<400> SEQUENCE: 33
cctcaaaata ttactgattt gtgtgcagaa taccacaaca cacaaatata tacgctaaat        60
gataagatat tttcgtatac agaatctcta gctggaaaaa gagagatggc tatcattact      120
tttaagaatg tgcaatttt tcaagtagaa gtaccaggta gtcaacatat agattcacaa       180 aaaaagcga ttgaaaggat gaaggatacc ctgaggattg catatcttac tgaagctaaa     240
```
gtcgaaaagt tatgtgtatg gaataataaa acgcctcatg cgattgccgc a            291

<210> SEQ ID NO 34
<211> LENGTH: 927
<212> TYPE: DNA
<213> ORGANISM: artificial
<220> FEATURE:
<223> OTHER INFORMATION: synthetic DNA

<400> SEQUENCE: 34
gatgattggg agattcctga tgggcagatt acagtgggac aaagaaaggg aaagtggcat     60
ggtgatgtgg cagtgaaaat gttgaatgtg acagcaccta cacctcagca gttacaagcc   120
ttcaaaaatg aagtaggagt actcaggaaa cacgacatg tgaatatcct actcttcatg    180
ggctattcca caaagccaca actggctatt gttacccagt ggtgtgaggg ctccagcttg   240
tatcaccatc tccatatcat tgagaccaaa tttgagatga tcaaacttat agatattgca   300
cgacagactg cacagggcat ggattactta cacgccaagt caatcatcca cagagacctc   360
aagagtaata atatatttct tcatgaagac ctcacagtaa aaataggtga ttttggtcta   420
gctacagaga atctcgatg gagtgggtcc catcagtttg aacagttgtc tggatccatt    480
ttgtggatgg caccagaagt catcagaatg caagataaaa atccatacag ctttcagtca   540
gatgtatatg catttgggat tgttctgtat gaattgatga ctggacagtt accttattca   600
aacatcaaca cagggacca gataattttt atggtgggac gaggataccct gtctccagat   660
ctcagtaagg tacggagtaa ctgtccaaaa gccatgaaga gattaatggc agagtgcctc   720
aaaaagaaaa gagatgagag accactctttt ccccaaattc tcgcctctat tgagctgctg   780
gcccgctcat tgccaaaaat tcaccgcagt gcatcgaaac cctccttgaa tcgggctggt   840
ttccaaacag aggattttag tctatatgct tgtgcttctc caaaaacacc catccaggca   900
ggggggatatg gtgcgtttcc tgtccac                                      927

<210> SEQ ID NO 35
<211> LENGTH: 92
<212> TYPE: DNA
<213> ORGANISM: artificial
<220> FEATURE:
<223> OTHER INFORMATION: synthetic DNA

<400> SEQUENCE: 35
cgattttggc ctggcgaccg aaaaagcggg cgattttggc ctggcgaccg aaaaagcggg     60
cgattttggc ctggcgaccg aaaaagcggg gc                                   92

<210> SEQ ID NO 36
<211> LENGTH: 1302
<212> TYPE: DNA
<213> ORGANISM: artificial
<220> FEATURE:
<223> OTHER INFORMATION: synthetic DNA

<400> SEQUENCE: 36
atgccaacaa taaccactgc acaaattaaa agcacactgc agtctgcaaa gcaatccgct     60
gcaaataaat tgcactcagc aggacaaagc acgaaagatg catcacctca aaatattact   120
gatttgtgtg cagaatacca caacacacaa atatatacgc taaatgataa gatattttcg   180
tatacagaat ctctagctgg aaaaagagag atggctatca ttacttttaa gaatggtgca   240
atttttcaag tagaagtacc aggtagtcaa catatagatt cacaaaaaaa agcgattgaa   300
aggatgaagg ataccctgag gattgcatat cttactgaag ctaaagtcga aaagttatgt   360

```
gtatggaata taaaacgcc tcatgcgatt gccgcaatgc ccgtgggagg ctgggagtgc      420
gagaagcatt cccaaccctg gcaggtgctt gtggcctctc gtggcagggc agtctgcggc      480
ggtgttctgg tgcaccccca gtgggtcctc acagctgccc actgcatcag gaacaaaagc      540
gtgatcttgc tgggtcggca cagcctgttt catcctgaag acacaggcca ggtatttcag      600
gtcagccaca gcttcccaca cccgctctac gatatgagcc tcctgaagaa tcgattcctc      660
aggccaggtg atgactccag ccacgacctc atgctgctcc gcctgtcaga gcctgccgag      720
ctcacggatg ctgtgaaggt catggacctg cccacccagg agccagcact ggggaccacc      780
tgctacgcct caggctgggg cagcattgaa ccagaggagt tcttgacccc aaagaaactt      840
cagtgtgtgg acctccatgt tatttccaat gacgtgtgtg cgcaagttca ccctcagaag      900
gtgaccaagt tcatgctgtg tgctggacgc tggacagggg gcaaaagcac ctgctcgggt      960
gattctgggg gcccacttgt ctgtaatggt gtgcttcaag gtatcacgtc atggggcagt     1020
gaaccatgtg ccctgcccga aaggccttcc ctgtacacca aggtggtgca ttaccggaag     1080
tggatcaagg acaccatcgt ggccaacccc gggcatgcat tagcctatgg aagtcagggt     1140
gatcttaatc cattaattaa tgaaatcagc aaaatcattt cagctgcagg tagcttcgat     1200
gttaaagagg aaagaactgc agcttcttta ttgcagttgt ccggtaatgc cagtgatttt     1260
tcatatggac ggaactcaat aaccctgacc acatcagcat aa                        1302
```

<210> SEQ ID NO 37
<211> LENGTH: 684
<212> TYPE: DNA
<213> ORGANISM: artificial
<220> FEATURE:
<223> OTHER INFORMATION: synthetic DNA

<400> SEQUENCE: 37

```
atgacaacaa taaccactgc acaaattaaa agcacactgc agtctgcaaa gcaatccgct       60
gcaaataaat tgcactcagc aggacaaagc acgaaagatg catcacctca aaatattact      120
gatttgtgtg cagaatacca caacacacaa atacatacgc taaatgataa gatattttcg      180
tatacagaat ctctagctgg aaaaagagag atggctatca ttacttttaa gaatggtgca      240
acttttcaag tagaagtacc aggtagtcaa catatagatt cacaaaaaaa agcgattgaa      300
aggatgaagg ataccctgag gattgcatat cttactgaag ctaaagtcga aagttatgt       360 gtatggaata taaaacgcc tcatgcgatt gccgcaatgc ccggcgattt tggcctggcg      420
accgaaaaag cgggcgattt tggcctggcg accgaaaaag cgggcgattt tggcctggcg      480
accgaaaaag cggggcatgc attagcctat ggaagtcagg gtgatcttaa tccattaatt      540
aatgaaatca gcaaaatcat ttcagctgca ggtagcttcg atgttaaaga ggaaagaact      600
gcagcttctt tattgcagtt gtccggtaat gccagtgatt tttcatatgg acggaactca      660
ataaccctga ccacatcagc ataa                                            684
```

<210> SEQ ID NO 38
<211> LENGTH: 1521
<212> TYPE: DNA
<213> ORGANISM: artificial
<220> FEATURE:
<223> OTHER INFORMATION: synthetic DNA

<400> SEQUENCE: 38

```
atgccaacaa taaccactgc acaaattaaa agcacactgc agtctgcaaa gcaatccgct       60
gcaaataaat tgcactcagc aggacaaagc acgaaagatg catcacctca aaatattact      120
```

```
gatttgtgtg cagaatacca caacacacaa atatatacgc taaatgataa gatattttcg    180
tatacagaat ctctagctgg aaaaagagag atggctatca ttacttttaa gaatggtgca    240
attttttcaag tagaagtacc aggtagtcaa catatagatt cacaaaaaaa agcgattgaa   300
aggatgaagg ataccctgag gattgcatat cttactgaag ctaaagtcga aagttatgt    360
gtatggaata ataaaacgcc tcatgcgatt gccgcaatgc ccgatgattg ggagattcct    420
gatgggcaga ttacagtggg acaaagaaag ggaaagtggc atggtgatgt ggcagtgaaa    480
atgttgaatg tgacagcacc tacacctcag cagttacaag ccttcaaaaa tgaagtagga    540
gtactcagga aaacacgaca tgtgaatatc ctactcttca tgggctattc cacaaagcca    600
caactggcta ttgttaccca gtggtgtgag ggctccagct tgtatcacca tctccatatc    660
attgagacca aatttgagat gatcaaactt atagatattg cacgacagac tgcacagggc    720
atggattact tacacgccaa gtcaatcatc cacagagacc tcaagagtaa taatatattt    780
cttcatgaag acctcacagt aaaaataggt gattttggtc tagctacaga gaaatctcga    840
tggagtgggt cccatcagtt tgaacagttg tctggatcca ttttgtggat ggcaccagaa    900
gtcatcagaa tgcaagataa aaatccatac agctttcagt cagatgtata tgcatttggg    960
attgttctgt atgaattgat gactggacag ttaccttatt caaacatcaa caacagggac   1020
cagataattt ttatggtggg acgaggatac ctgtctccag atctcagtaa ggtacggagt   1080
aactgtccaa aagccatgaa gagattaatg gcagagtgcc tcaaaaagaa aagagatgag   1140
agaccactct ttccccaaat tctcgcctct attgagctgc tggcccgctc attgccaaaa   1200
attcaccgca gtgcatcaga accctccttg aatcgggctg gtttccaaac agaggatttt   1260
agtctatatg cttgtgcttc tccaaaaaca cccatccagg caggggata tggtgcgttt    1320
cctgtccacg ggcatgcatt agcctatgga agtcagggtg atcttaatcc attaattaat   1380
gaaatcagca aaatcatttc agctgcaggt agcttcgatg ttaaagagga agaactgca    1440
gcttctttat tgcagttgtc cggtaatgcc agtgattttt catatggacg gaactcaata   1500
accctgacca catcagcata a                                             1521

<210> SEQ ID NO 39
<211> LENGTH: 2169
<212> TYPE: DNA
<213> ORGANISM: artificial
<220> FEATURE:
<223> OTHER INFORMATION: synthetic DNA

<400> SEQUENCE: 39
atgacaacaa taaccactgc acaaattaaa agcacactgc agtctgcaaa gcaatccgct     60
gcaaataaat tgcactcagc aggacaaagc acgaaagatg catcacctca aaatattact    120
gatttgtgtg cagaatacca caacacacaa atacatacgc taaatgataa gatattttcg    180
tatacagaat ctctagctgg aaaaagagag atggctatca ttacttttaa gaatggtgca    240
acttttcaag tagaagtacc aggtagtcaa catatagatt cacaaaaaaa agcgattgaa    300
aggatgaagg ataccctgag gattgcatat cttactgaag ctaaagtcga aagttatgt    360
gtatggaata ataaaacgcc tcatgcgatt gccgcaatgc ccatctgtca aatggagaaa    420
atagtgcttc ttttttgcaat agtcagtctt gttaaaagtg atcagatttg cattggttac    480
catgcaaaca actcgacaga gcaggttgac acaataatgg aaaagaacgt tactgttaca    540
catgcccaag acatactgga aaagacacac aacgggaagc tctgcgatct agatggagtg    600
aagcctctaa ttttgagaga ttgtagtgta gctggatggc tcctcggaaa cccaatgtgt    660
```

```
gacgaattca tcaatgtgcc ggaatggtcc tacatagtgg agaaggccaa tccagtcaat    720
gacctctgtt acccagggga tttcaatgac tatgaagaat tgaaacacct attgagcaga    780
ataaaccatt ttgagaaaat tcagatcatc cccaaaagtt cttggtccag tcatgaagcc    840
tcattagggg tgagctcagc atgtccatac cagagaaagt cctccttttt cagaaatgtg    900
gtatggctta tcaaaagaa cagtacatac ccaacaataa agaggagcta caataatacc    960
aaccaagaag atcttttggt actgtggggg attcaccatc ctaatgatgc ggcagagcag    1020
acaaagctct atcaaaaccc aaccacctat atttccgttg gacatcaac actaaaccag    1080 agattggtac caagaatagc tactagatcc aaagtaaacg ggcaaagtgg aaggatggag    1140
ttcttctgga caattttaaa accgaatgat gcaatcaact tcgagagtaa tggaaatttc    1200
attgctccag aatatgcata caaaattgtc aagaaggggg actcaacaat tatgaaaagt    1260
gaattggaat atggtaactg caacaccaag tgtcaaactc caatggggc gataaactct    1320 agtatgccat tccacaatat acaccctctc accatcgggg aatgccccaa atatgtgaaa    1380
tcaaacagat tagtccttgc gactgggctc agaaatagcc ctcaaagaga gagaagaaga    1440 aaaagagag gattatttgg agctatagca ggttttatag agggaggatg gcagggaatg    1500
gtagatggtt ggtatgggta ccaccatagc aatgagcagg gagtgggta cgctgcagac    1560 aaagaatcca ctcaaaaggc aatagatgga gtcaccaata aggtcaactc gatcattgac    1620
aaaatgaaca ctcagtttga ggccgttgga agggaattta caacttaga aaggagaata    1680 gagaatttaa acaagaagat ggaagacggg ttcctagatg tctggactta taatgctgaa    1740
cttctggttc tcatggaaaa tgagagaact ctagactttc atgactcaaa tgtcaagaac    1800
ctttacgaca aggtccgact acagcttagg gataatgcaa aggaactggg taacggttgt    1860
ttcgagttct atcataaatg tgataatgaa tgtatggaaa gtgtaagaaa cggaacgtat    1920
gactacccgc agtattcaga agaagcaaga ctaaaaagag aggaaataag tggagtaggg    1980
catgcattag cctatggaag tcagggtgat cttaatccat taattaatga aatcagcaaa    2040
atcatttcag ctgcaggtag cttcgatgtt aagagggaaa gaactgcagc ttctttattg    2100
cagttgtccg gtaatgccag tgatttttca tatggacgga actcaataac cctgaccaca    2160
tcagcataa                                                            2169
```

<210> SEQ ID NO 40
<211> LENGTH: 12672
<212> TYPE: DNA
<213> ORGANISM: artificial
<220> FEATURE:
<223> OTHER INFORMATION: synthetic DNA

<400> SEQUENCE: 40

```
gaattccaag cgaagtccat cccctcct cttgattaca agggtgataa ttattattcg     60
catttgtgtg gtaatgggat agaaaggaat ggatagaaaa agaacaaaat tagtatagca    120
atagatatgc ccactgcatt gaatacttac agggcattat tttattatgt ttaaattgaa    180
gtggtctctg gtttgattta tttgttattc aaggggctg tttggagatc ggaaaattct    240
gtacgttaag tgtattattt aaccagtttc gatgcgtaac agattgattt tgcgtcagcg    300
gttatcgctt ttaagttgtt gctcttgcgc tatcgcgttt aggttatccg attaaagtca    360
aatttcctga aaatgctgta tagcgcggga gtgcacctta tagctgtagg taagtatgtt    420
caaaaaatag tcttgccgta caataatttt ccatatccaa actcactcct tcaagattct    480
ggtcccggtt tacgggtagt ttccggaagg gcggtagcat gctgattcaa actgcaagat    540
```

```
gaaacattgt cggagttgga tggaattaag tcatggctat agcatttggg cgtgcataac    600
aaaattggtc ctcatatttt agagtatgat tgcatattca ctaatatttt tactttctga    660
tgcgtggtgg catcatgctt tatgagataa acaatcctgg tagactagcc ccctgaatct    720
ccagacaacc aatatcactt atttaagtga tagtcttaat actagttttt agactagtca    780
ttggagaaca atgattgat gtcttaggat cggagaaacg cagacggcgt actacacagg     840
aaaagatcgc tatcgttcag cagagctttg aaccgggaat gacggtctcc cttgttgccc    900
ggcaacatgg tgtggcagcc agccagctat ttctctggcg caagcaatac caggagggaa    960
gtcttactgc tgtggctgcc ggagaacagg tcgttcctgc ctctgaactt gctgccgcca   1020
tgaagcagat taaagagctc cagcgcctgc tcggcaaaaa aacgatggaa aatgaactcc   1080
ttaaagaagc cgttgaatat gggcgagcaa aaaagtggat agcgcacgcg cccttattgc   1140
ccggggatgg ggagtaagct tcgtcagccg ttgtctccgg gtgtcgcgtg cgcagttgca   1200
cgtcattctc agacgaaccg atgactggaa ggacggccgc cgcagccgtc acacggatga   1260
tacggatgtg cttcgccgta tacatcatgt tatcggagag ctgcccacat atggttatcg   1320
tcgggtatgg cgctgcttc gcagacaaac agaacttgat ggtatgcctg cgatcaatgc    1380
caaatgtgtt taccggatca tgtgccagaa tgcgctgttg cttgagcgaa acccgctgt    1440 accgccatcg aaacgggcac ataccggcag agtggctgtg aaagaaagta atcagcgatg   1500
gtgctctgac gggtttgagt tccgctgtga taacggagaa aaactgcggg tcacgttcgc   1560
gctggactgc tgtgatcgtg aggcactgca ctgggcggtc acaacgggtg gcttcaacag   1620
tgaaacagta caggacgtca tgctgggagc agtggaacgc cgctttggca gcgagcttcc   1680
ggcgtctcca gtggagtggc tgacggataa tggttcatgc taccgggcga atgaaacacg   1740
tcagttcgcc aggatgttgg gacttgaacc gaagaacacg gcagtgcgga gtccggagag   1800
taacggaata acagagagct tcgtgaaaac gataaagcgt gattacataa gtatcatgcc   1860
caaaccagac gggttaacgg cagcaaagaa ccttgcagag gcgttcgagc attataacga   1920
atggcatccg catagtgcgc tgggttatcg ctcgccacgg gaatatctgc ggcagcgggc   1980
cagtaatggg ttaagtgata acaggtatct ggaaatatag gggcaaatcc acctggtcat   2040
tatctggaat ttgacgaagt gtgataactg gtatagccag attaatctaa acctttgtct   2100
gacaaaatca gataaagaag agtagttcaa aagacaactc gtggactctc attcagagag   2160
ataggcgtta ccaaaatttg tttggaactg aacaagaaaa ttgtatttgt gtaactataa   2220
tcttaatgta aaataaaaga caccagttct gtagaatatg cttattgaag agagtgtaat   2280
aataatttta tatagatgtt gtacaaagaa caggaatgag taattattta tgcttgatgt   2340
tttttgactc ttgcttttta tagttattat ttttaagtta gtcagcgcaa taaaaacttg   2400
cttttaatat taatgcgagt tatgacatta acggaagaa acataaaggc atattttgc     2460 cacaatattt aatcatataa tttaagttgt agtgagttta ttatgaatat aaacaaacca   2520
ttagagattc ttgggcatgt atcctggcta tgggccagtt ctccactaca cagaaactgg   2580
ccagtatctt tgtttgcaat aaatgtatta cccgcaatac aggctaacca atatgtttta   2640
ttaacccggg atgattaccc tgtcgcgtat tgtagttggg ctaatttaag tttagaaaat   2700
gaaattaaat atcttaatga tgttacctca ttagttgcag aagactggac ttcaggtgat   2760
cgtaaatggt tcattgactg gattgctcct ttcggggata acggtgccct gtacaaatat   2820
atgcgaaaaa aattccctga tgaactattc agagccatca gggtggatcc caaaactcat   2880
gttggtaaag tatcagaatt tcatggaggt aaaattgata aacagttagc gaataaaatt   2940
```

```
tttaaacaat atcaccacga gttaataact gaagtaaaaa gaaagtcaga ttttaatttt    3000
tcattaactg gttaagaggt aattaaatgc caacaataac cactgcacaa attaaaagca    3060
cactgcagtc tgcaaagcaa tccgctgcaa ataaattgca ctcagcagga caaagcacga    3120
aagatgcatt agcctatgga agtcagggtg atcttaatcc attaattaat gaaatcagca    3180
aaatcatttc agctgcaggt agcttcgatg ttaaagagga agaactgca gcttcttttat    3240 tgcagttgtc cggtaatgcc agtgattttt catatggacg gaactcaata accctgacca    3300
catcagcata atatattaat ttaaatgata gcaatcttac tgggctgtgc cacataagat    3360
tgctattttt tttggagtca taatggattc ttgtcataaa attgattatg ggttatacgc    3420
cctggagatt ttagcccaat accataacgt ctctgttaac ccggaagaaa ttaaacatag    3480
atttgataca gacgggacag gtctgggatt aacgtcatgg ttgcttgctg cgaaatcttt    3540
agaactaaag gtaaacagg taaaaaaaac aattgatcga ttaaacttta tttttctgcc    3600
cgcattagtc tggagagagg atggacgtca ttttattctg actaaaatca gcaaagaagt    3660
aaacagatat cttattttg atttggagca gcgaaatccc cgtgttctcg aacagtctga    3720
gtttgaggcg ttatatcagg ggcatattat tcttattact tcccgttctt ctgttaccgg    3780
gaaactggca aaatttgact ttacctggtt tattcctgcc attataaaat acaggagaat    3840
atttattgaa acccttgttg tatctgtttt tttacaatta tttgcattaa taccccccct    3900
ttttttccag gtggttatgg acaaagtatt agtgcacagg gggttttcaa cccttaatgt    3960
tattactgtt gcattatctg ttgtagtggt gtttgagatt atactcagcg gtttaagaac    4020 ttacatttt gcacatagta caagtcggat tgatgttgag ttgggtgcca aactcttccg    4080
gcatttactg gcgctaccga tctcttattt tgagagtcgt cgtgttggtg atactgttgc    4140
gagggtaaga gaattagacc agatccgtaa ttttctgaca ggacaggcat aacatctgt    4200 tttggactta ttattttcac tcatattttt tgcggtaatg tggtattaca gcccaaagct    4260
tactctggtg atcttatttt cgctgccttg ttatgctgca tggtctgttt ttattagccc    4320 catttttgcga cgtcgccttg atgataagtt ttcacggaat gcggataatc aatctttcct    4380
ggtggaatca gtaacggcga ttaacactat aaaagctatg gcagtctcac ctcagatgac    4440
gaacatatgg gacaaacaat tggcaggata tgttgctgca ggctttaaag tgacagtatt    4500
agcaaccatt ggtcaacaag gaatacagtt aatacaaaag actgttatga tcatcaacct    4560
atggttggga gcacacctgg ttatttccgg ggatttaagt attggtcagt taattgcttt    4620
taatatgctt gctggtcaga ttgttgcacc ggttattcgc cttgcacaaa tctggcagga    4680
tttccagcag gttggtatat cagttacccg ccttggtgat gtgcttaact ctccaactga    4740
aagttatcat gggaaactga cattgccgga aattaatggt gatatcactt ttcgtaatat    4800
ccggtttcgc tataaacctg attctccggt tattttggac aatatcaatc ttagtattaa    4860 gcaggggag gttattggta ttgtcggacg ttctggttca ggaaaaagca cattaactaa    4920
attaattcaa cgttttata ttcctgaaaa tggccaggta ttaattgatg gacatgatct    4980
tgcgttggct gatcctaact ggttacgtcg tcaggtgggg gttgtgttgc aggacaatgt    5040
gctgcttaat cgcagtatta ttgataatat ttcactggct aatcctggca tgtccgtcga    5100
aaagtgtatt tatgcagcga aattagcagg cgctcatgat tttatttctg atttgcgtga    5160
ggggtataac accattgtcg gggaacaggg ggcaggatta tccggaggtc aacgtcaacg    5220
catcgcaatt gcagggcgc tggtgaacaa ccctaaaata ctcattttg atgaagcaac    5280 cagtgctctg gattatgagt cggagcatgt catcatgcgc aatatgcaca aaatatgtaa    5340
```

```
gggcagaacg gttataatca ttgctcatcg tctgtctaca gtaaaaaatg cagaccgcat   5400
tattgtcatg gaaaaaggga aaattgttga acagggtaaa cataaggagc tgctttctga   5460
accggaaagt ttatacagtt acttatatca gttacagtca gactaacaga agaacagaa   5520 gaatatgaaa acatggttaa tggggttcag cgagttcctg ttgcgctata aacttgtctg   5580
gagtgaaaca tggaaaatcc ggaagcaatt agatactccg gtacgtgaaa aggacgaaaa   5640
tgaattctta cccgctcatc tggaattaat tgaaacgcca gtatccagac ggccgcgtct   5700
ggttgcttat tttattatgg ggtttctggt tattgctttt attttatctg ttttaggcca   5760
agtggaaatt gttgccactg caaatgggaa attaacacac agtgggcgta gtaaagaaat   5820
taaacctatt gaaaactcaa tagttaaaga aattatcgta aaagaaggag agtcagtccg   5880
gaaaggggat gtgttattaa agcttacagc actgggagct gaagctgata cgttaaaaac   5940
acagtcatca ctgttacagg ccaggctgga acaaactcgg tatcaaattc tgagcaggtc   6000
aattgaatta aataaactac ctgaactaaa gcttcctgat gagccttatt ttcagaatgt   6060
atctgaagag gaagtactgc gtttaacttc tttgataaaa gaacagtttt ccacatggca   6120 aaaatcagaag tatcaaaaag aactgaattt ggataagaaa agagcagagc gattaacagt   6180
acttgcccgt ataaccgtt atgaaaattt atcaagggtt gaaaaagcc gtctggatga   6240 tttcagtagt ttattgcata acaggcaat tgcaaacat gctgtacttg agcaggagaa   6300
taaatatgtc gaagcagtaa atgaattacg agtttataaa tcacaactgg agcaaattga   6360
gagtgagata ttgtctgcaa aagaagaata tcagcttgtt acgcagcttt ttaaaaatga   6420
aattttagat aagctaagac aaacaacaga caacattggg ttattaactc tggaattagc   6480
gaaaaatgaa gagcgtcaac aggcttcagt aatcagggcc ccagtttcgg gaaaagttca   6540
gcaactgaag gttcatactg aaggtggggt tgttacaaca gcggaaacac tgatggtcat   6600
cgttccggaa gatgacacgc tggaggttac tgctctggta caaaataaag atattggttt   6660
tattaacgtc gggcagaatg ccatcattaa agtggaggca tttccttata cacgatatgg   6720
ttatctggtg ggtaaggtga aaatataaaa tttagatgca atagaagacc agagactggg   6780
acttgttttt aatgttatta tttctattga agagaattgt ttgtcaaccg ggaataaaaa   6840
cattccatta agctcgggta tggcagtcac tgcagaaata aagacaggta tgcgaagtgt   6900
aatcagttat cttcttagtc ctttagaaga gtcagtaaca gaaagtttac gtgagcgtta   6960
agtttcagaa gtccagtatt tgctgctata cgtgctgcgt ggcacttgcc gtctgaacgg   7020
cattgatccg gaagccaagt caaacaacag cgtgatgagc gtcagggcaa acaccaagg   7080 ctctctcgat gacaccagaa caaattgaaa tacgtgagct gaggaaaaag ctaccgagtt   7140
cttgatgttg gactccctga acagttctct gtaatcggga aactcaggac gcgttatcct   7200
gtggtcacac tctgccatgt gtttaggggt catcacagca gctacagata ctggtaaaac   7260
cgtcctgaaa aaccagacgg cagacgggct gtattacgta gtcaggtact tgagctacat   7320
ggcatcagtc acggtttggc cggagcaaga cgtatcacca caatggcaac ccggagaggt   7380
gtcagcgcca gtgatataag acggttaacg gttaaaaatc gtggcgttga caacatccca   7440
gtggactgag gtcacacagg cctggcagca ttcctcttcc ggccggatga cccggatttc   7500
acggggaaag tacgccgata acagtttacg ggctgaagat tggcgtaggg aggatagcag   7560
acgttttgcc gccccatttg tctggagttg ggtgagaagg catcatttca ccaacaccaa   7620
catttcacag ttcacccca cagctacatg aagcgcttcc atgaattatc gctttgattt   7680
atcatgttaa aatagctcta cacggttggt tcaggattgc gcaccgaaac cctctaaaat   7740
```

```
ccactgacgc gcctgcgaat tatccagcac cgcgcctttc gagatcctct acgccggacg    7800
catcgtggcc ggcatcaccg cgccacagg tgcggttgct ggcgcctata tcgccgacat     7860
caccgatggg gaagatcggg ctcgccactt cgggctcatg agcgcttgtt tcggcgtggg    7920
tatggtggca ggccccgtgg ccgggggact gttgggcgcc atctccttgc atgcaccatt    7980
ccttgcggcg gcggtgctca acggcctcaa cctactactg ggctgcttcc taatgcagga    8040
gtcgcataag ggagagcgtc gaccgatgcc cttgagagcc ttcaacccag tcagctcctt    8100
ccggtgggcg cggggcatga ctatcgtcgc cgcacttatg actgtcttct ttatcatgca    8160
actcgtagga caggtgccgg cagcgctctg ggtcattttc ggcgaggacc gctttcgctg    8220
gagcgcgacg atgatcggcc tgtcgcttgc ggtattcgga atcttgcacg ccctcgctca    8280
agccttcgtc actggtcccg ccaccaaacg tttcggcgag aagcaggcca ttatcgccgg    8340
catggcggcc gacgcgctgg gctacgtctt gctggcgttc gcgacgcgag gctggatggc    8400
cttccccatt atgattcttc tcgcttccgg cggcatcggg atgcccgcgt tgcaggccat    8460
gctgtccagg caggtagatg acgaccatca gggacagctt caaggatcgc tcgcggctct    8520
taccagccta acttcgatca ttggaccgct gatcgtcacg gcgatttatg ccgcctcggc    8580
gagcacatgg aacgggttgg catggattgt aggcgccgcc ctataccttg tctgcctccc    8640
cgcgttgcgt cgcggtgcat ggagccgggc cacctcgacc tgaatggaag ccggcggcac    8700
ctcgctaacg gattcaccac tccaagaatt ggagccaatc aattcttgcg gagaactgtg    8760
aatgcgcaaa ccaacccttg gcagaacata tccatcgcgt ccgccatctc cagcagccgc    8820
acgcggcgca tctcgggcag cgttgggtcc tggccacggg tgcgcatgat cgtgctcctg    8880
tcgttgagga cccggctagg ctggcggggt tgccttactg gttagcagaa tgaatcaccg    8940
atacgcgagc gaacgtgaag cgactgctgc tgcaaaacgt ctgcgacctg agcaacaaca    9000
tgaatggtct tcgtttccg tgtttcgtaa agtctggaaa cgcggaagtc agcgccctgc     9060
accattatgt tccggatctg catcgcagga tgctgctggc tacccgtgtgg aacacctaca   9120 tctgtattaa cgaagcgctg gcattgaccc tgagtgattt ttctctggtc ccgccgcatc    9180
cataccgcca gttgtttacc ctcacaacgt tccagtaacc gggcatgttc atcatcagta    9240
acccgtatcg tgagcatcct ctctcgtttc atcggtatca ttaccccccat gaacagaaat   9300 cccccttaca cggaggcatc agtgaccaaa caggaaaaaa ccgcccttaa catggcccgc    9360
tttatcagaa gccagacatt aacgcttctg gagaaactca acgagctgga cgcggatgaa    9420
caggcagaca tctgtgaatc gcttcacgac cacgctgatg agctttaccg cagctgcctc    9480
gcgcgtttcg gtgatgacgg tgaaaacctc tgacacatgc agctcccgga gacggtcaca    9540
gcttgtctgt aagcggatgc cgggagcaga caagcccgtc agggcgcgtc agcgggtgtt    9600
ggcgggtgtc ggggcgcagc catgacccag tcacgtagcg atagcggagt gtatactggc    9660
ttaactatgc ggcatcagag cagattgtac tgagagtgca ccatatgcgg tgtgaaatac    9720
cgcacagatg cgtaaggaga aaataccgca tcaggcgctc ttccgcttcc tcgctcactg    9780
actcgctgcg ctcggtcgtt cggctgcggc gagcggtatc agctcactca aaggcggtaa    9840
tacggttatc cacagaatca ggggataacg caggaaagaa catgtgagca aaaggccagc    9900
aaaaggccag gaaccgtaaa aaggccgcgt tgctggcgtt tttccatagg ctccgccccc    9960
ctgacgagca tcacaaaaat cgacgctcaa gtcagaggtg cgaaacccg acaggactat     10020 aaagatacca ggcgtttccc cctggaagct ccctcgtgcg ctctcctgtt ccgacctgc     10080 cgcttaccgg atacctgtcc gcctttctcc cttcgggaag cgtggcgctt tctcatagct    10140
```

```
cacgctgtag gtatctcagt tcggtgtagg tcgttcgctc caagctgggc tgtgtgcacg    10200
aaccccccgt tcagcccgac cgctgcgcct tatccggtaa ctatcgtctt gagtccaacc    10260
cggtaagaca cgacttatcg ccactggcag cagccactgg taacaggatt agcagagcga    10320
ggtatgtagg cggtgctaca gagttcttga agtggtggcc taactacggc tacactagaa    10380
ggacagtatt tggtatctgc gctctgctga agccagttac cttcggaaaa agagttggta    10440
gctcttgatc cggcaaacaa accaccgctg gtagcggtgg ttttttttgtt tgcaagcagc    10500 agattacgcg cagaaaaaaa ggatctcaag aagatccttt gatcttttct acggggtctg    10560
acgctcagtg gaacgaaaac tcacgttaag ggattttggt catgagatta tcaaaaagga    10620
tcttcaccta gatcctttta aattaaaaat gaagttttaa atcaatctaa agtatatatg    10680
agtaaacttg gtctgacagt taccaatgct taatcagtga ggcacctatc tcagcgatct    10740
gtctatttcg ttcatccata gttgcctgac tccccatatg aatatcctcc ttagttccta    10800
ttccgaagtt cctattctct agaaagtata ggaacttcag agcgcttttg aagctggggt    10860
gggcgaagaa ctccagcatg agatccccgc gctggaggat catccagccg gcgtccgga    10920 aaacgattcc gaagcccaac ctttcataga aggcggcggt ggaatcgaaa tctcgtgatg    10980
gcaggttggg cgtcgcttgg tcggtcattt cgaaccccag agtcccgctc agaagaactc    11040
gtcaagaagg cgatagaagg cgatgcgctg cgaatcggga gcggcgatac cgtaaagcac    11100
gaggaagcgg tcagcccatt cgccgccaag ctcttcagca atatcacggg tagccaacgc    11160
tatgtcctga tagcggtccg ccacacccag ccggccacag tcgatgaatc cagaaaagcg    11220
gccattttcc accatgatat tcggcaagca ggcatcgcca tgggtcacga cgagatcctc    11280
gccgtcgggc atgcgcgcct tgagcctggc gaacagttcg gctggcgcga gccctgatg    11340 ctcttcgtcc agatcatcct gatcgacaag accggcttcc atccgagtac gtgctcgctc    11400
gatgcgatgt ttcgcttggt ggtcgaatgg gcaggtagcc ggatcaagcg tatgcagccg    11460
ccgcattgca tcagccatga tggatacttt ctcggcagga gcaaggtgag atgacaggag    11520
atcctgcccc ggcacttcgc ccaatagcag ccagtccctt cccgcttcag tgacaacgtc    11580
gagcacagct gcgcaaggaa cgcccgtcgt ggccagccac gatagccgcg ctgcctcgtc    11640
ctgcagttca ttcagggcac cggacaggtc ggtcttgaca aaaagaaccg ggcgccctg    11700 cgctgacagc cggaacacgg cggcatcaga gcagccgatt gtctgttgtg cccagtcata    11760
gccgaatagc ctctccaccc aagcggccgg agaacctgcg tgcaatccat cttgttcaat    11820
catgcgaaac gatcctcatc ctgtctcttg atcagatctt gatccctgc gccatcagat    11880 ccttggcggc aagaaagcca tccagtttac tttgcagggc ttcccaacct taccagaggg    11940
cgccccagct ggcaattccg gttcgcttgc tgtccataaa accgcccagt ctagctatcg    12000
ccatgtaagc ccactgcaag ctacctgctt tctctttgcg cttgcgtttt cccttgtcca    12060
gatagcccag tagctgacat tcatccgggg tcagcaccgt ttctgcggac tggctttcta    12120
cgtgttccgc ttccttttagc agcccttgcg ccctgagtgc ttgcggcagc gtggggatc    12180 ttgaagttcc tattccgaag ttcctattct ctagaaagta taggaacttc gaagcagctc    12240
cagcctacac caaaaaaggg aataaggggcg acacggaaat gttgaatact catactcttc    12300 cttttttcaat attattgaag catttatcag ggttattgtc tcatgagcgg atacatattt    12360
gaatgtattt agaaaaataa acaaataggg gttccgcgca catttccccg aaaagtgcca    12420
cctgacgtct aagaaaccat tattatcatg acattaacct ataaaaatag gcgtatcacg    12480
aggccctttc gtcttcaaga attctcatgt ttgacagctt atcatcgatg acattattt    12540
```

```
ttgtggagcc ggaggaaaca gaccagacgg ttcagatgag gcgcttacca ccagaaccgc    12600
tgttgtccca ccattctggc gattcccaaa cgctatttgg ataaaaagta gccttaacgt    12660
ggtttatttt cc                                                        12672
```